US007557206B2

United States Patent
Kumar et al.

(10) Patent No.: US 7,557,206 B2
(45) Date of Patent: Jul. 7, 2009

(54) PHOTOCHROMIC COMPOUNDS

(75) Inventors: Anil Kumar, Murrysville, PA (US); Meng He, Murrysville, PA (US); Terry A. Kellar, II, Monroeville, PA (US); Forrest R. Blackburn, Monroeville, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 28 days.

(21) Appl. No.: 11/924,966

(22) Filed: Oct. 26, 2007

(65) Prior Publication Data

US 2008/0045704 A1 Feb. 21, 2008

Related U.S. Application Data

(62) Division of application No. 10/846,629, filed on May 17, 2004, now Pat. No. 7,342,112.

(60) Provisional application No. 60/484,100, filed on Jul. 1, 2003.

(51) Int. Cl.
*C07D 491/10* (2006.01)
*G02F 1/00* (2006.01)
(52) U.S. Cl. .................. 544/71; 252/383; 359/241; 549/333
(58) Field of Classification Search .......... None
See application file for complete search history.

(56) References Cited

U.S. PATENT DOCUMENTS 6,022,497 A * 2/2000 Kumar ............... 252/586
6,690,495 B1 * 2/2004 Kosa et al. ............... 349/86

* cited by examiner

*Primary Examiner*—Kamal A Saeed
(74) *Attorney, Agent, or Firm*—Linda Pingitore; Frank P. Makak; Deborah M. Altman

(57) ABSTRACT

Various non-limiting embodiments disclosed herein relate generally to photochromic compounds, which may be thermally reversible or non-thermally reversible, and articles made therefrom. Other non-limiting embodiments relate to photochromic-dichroic compounds, which may be thermally reversible or non-thermally reversible, and articles made therefrom. For example, one non-limiting embodiment provides a thermally reversible, photochromic compound adapted to have at least a first state and a second state, wherein the thermally reversible, photochromic compound has an average absorption ratio greater than 2.3 in at least one state as determined according to CELL METHOD. Another non-limiting embodiment provides a photochromic compound comprising: (a) at least one photochromic group chosen from a pyran, an oxazine, and a fulgide; and (b) at least one lengthening agent L attached to the at least one photochromic group and represented by the formula —$[S_1]_c$-$[Q_1$-$[S_2]_d]_{d'}$-$[Q_2$-$[S_3]_e]_{e'}$-$[Q_3$-$[S_4]_f]_{f'}$—$S_5$—P, which is described herein.

3 Claims, 1 Drawing Sheet

PHOTOCHROMIC COMPOUNDS

CROSS-REFERENCE TO RELATED APPLICATIONS

Figure 1:
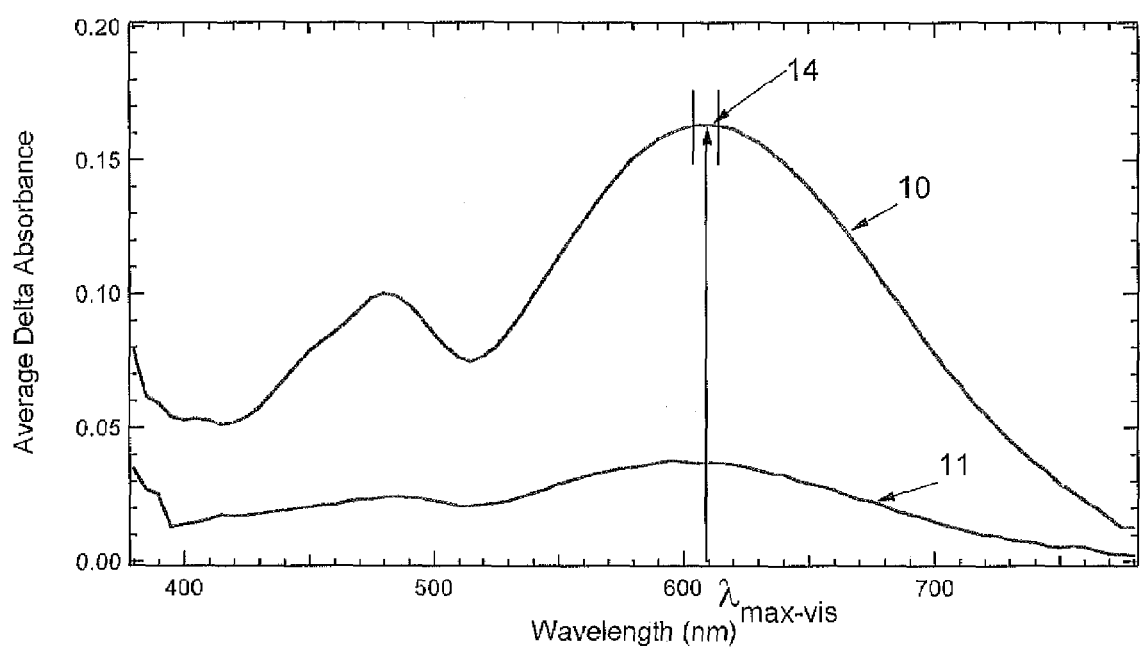

This Application is a divisional of U.S. application Ser. No. 10/846,629 filed on May 17, 2004, now U.S. Pat. No. 7,342,112, which in turn claims benefit of U.S. Provisional Application Ser. No. 60/484,100, filed Jul. 1, 2003, which is hereby specifically incorporated by reference.

STATEMENT REGARDING FEDERALLY SPONSORED RESEARCH OR DEVELOPMENT

Not applicable.

REFERENCE TO A SEQUENCE LISTING

Not applicable.

BACKGROUND

Various non-limiting embodiments disclosed herein relate generally to photochromic compounds. Other non-limiting embodiments relate to devices and elements made using the photochromic compounds disclosed herein.

Conventional photochromic compounds have at least two states, a first state having a first absorption spectrum and a second state having a second absorption spectrum that differs from the first absorption spectrum, and are capable of switching between the two states in response to at least actinic radiation. Further, conventional photochromic compounds can be thermally reversible. That is, conventional photochromic compounds are capable of switching between a first state and a second state in response to at least actinic radiation and reverting back to the first state in response to thermal energy. As used herein "actinic radiation" means electromagnetic radiation, such as but not limited to ultraviolet and visible radiation that is capable of causing a response. More specifically, conventional photochromic compounds can undergo a transformation in response to actinic radiation from one isomer to another, with each isomer having a characteristic absorption spectrum, and can further revert back to the first isomer in response to thermal energy (i.e., be thermally reversible). For example, conventional thermally reversible photochromic compounds are generally capable of switching from a first state, for example a "clear state," to a second state, for example a "colored state," in response to actinic radiation and reverting back to the "clear" state in response to thermal energy.

Dichroic compounds are compounds that are capable of absorbing one of two orthogonal plane polarized components of transmitted radiation more strongly than the other. Thus, dichroic compounds are capable of linearly polarizing transmitted radiation. As used herein, "linearly polarize" means to confine the vibrations of the electric vector of light waves to one direction or plane. However, although dichroic materials are capable of preferentially absorbing one of two orthogonal plane polarized components of transmitted radiation, if the molecules of the dichroic compound are not suitably positioned or arranged, no net linear polarization of transmitted radiation will be achieved. That is, due to the random positioning of the molecules of the dichroic compound, selective absorption by the individual molecules will cancel each other such that no net or overall linear polarizing effect is achieved. Thus, it is generally necessary to suitably position or arrange the molecules of the dichroic compound within another material in order to form a conventional linear polarizing element, such as a linearly polarizing filter or lens for sunglasses.

In contrast to the dichroic compounds, it is generally not necessary to position or arrange the molecules of conventional photochromic compounds to form a conventional photochromic element. Thus, for example, conventional photochromic elements, such as lenses for photochromic eyewear, can be formed, for example, by spin coating a solution containing a conventional photochromic compound and a "host" material onto the surface of the lens, and suitably curing the resultant coating or layer without arranging the photochromic compound in any particular orientation. Further, even if the molecules of the conventional photochromic compound were suitably positioned or arranged as discussed above with respect to the dichroic compounds, because conventional photochromic compounds do not strongly demonstrate dichroism, elements made therefrom are generally not strongly linearly polarizing.

It would be advantageous to provide photochromic compounds, such as but not limited to thermally reversible photochromic compounds, that can exhibit useful photochromic and/or dichroic properties in at least one state, and that can be used in a variety of applications to impart photochromic and/or dichroic properties.

BRIEF DESCRIPTION OF THE SEVERAL VIEWS OF THE DRAWING(S)

Various non-limiting embodiments of the present invention will be better understood when read in conjunction with the drawings, in which:

FIG. 1 shows two average difference absorption spectrum obtained for a photochromic compound according to various non-limiting embodiments disclosed herein using the CELL METHOD.

DETAILED DESCRIPTION

As used in this specification and the appended claims, the articles "a," "an," and "the" include plural referents unless expressly and unequivocally limited to one referent.

Additionally, for the purposes of this specification, unless otherwise indicated, all numbers expressing quantities of ingredients, reaction conditions, and other properties or parameters used in the specification are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

Further, while the numerical ranges and parameters setting forth the broad scope of the invention are approximations as discussed above, the numerical values set forth in the Examples section are reported as precisely as possible. It should be understood, however, that such numerical values inherently contain certain errors resulting from the measurement equipment and/or measurement technique.

Various non-limiting embodiments of the invention will now be described. One non-limiting embodiment provides a thermally reversible, photochromic compound adapted to have at least a first state and a second state, wherein the thermally reversible, photochromic compound has an average absorption ratio greater than 2.3 in at least one state as determined according to the CELL METHOD, which is described in detail below. Further, according various non-limiting embodiments, the thermally reversible, photochromic compound has an average absorption ratio greater than 2.3 in an activated state as determined according to the CELL METHOD. As used herein, the term "photochromic compound" includes both thermally reversible and non-thermally reversible (or photo-reversible) photochromic compounds. As used herein with respect to photochromic compounds, the term "activated state" refers to the photochromic compound when exposed to sufficient actinic radiation to cause the at least a portion of the photochromic compound to switch states. Further, as used herein the term "compound" means a substance formed by the union of two or more elements, components, ingredients, or parts and includes, without limitation, molecules and macromolecules (for example polymers or oligomers) formed by the union of two or more elements, components, ingredients, or parts.

Generally speaking, the CELL METHOD of measuring average absorption ratio of a photochromic compound involves obtaining an absorption spectrum for the photochromic compound, in an activated or an unactivated state, in each of two orthogonal polarization directions while the photochromic compound is at least partially aligned in an aligned liquid crystal medium that is contained within a cell assembly. More specifically, the cell assembly comprises two opposing glass substrates that are spaced apart by 20 microns+/−1 micron. The substrates are sealed along two opposite edges to form the cell. The inner surface of each of the glass substrates is coated with a polyimide coating, the surface of which has been at least partially ordered by rubbing. Alignment of the photochromic compound is achieved by introducing the photochromic compound and a liquid crystal medium into the cell assembly and allowing the liquid crystal medium to align with the rubbed polyimide surface. Because the photochromic compound is contained within the liquid crystal medium, alignment of the liquid crystal medium causes the photochromic compound to be aligned. It will be appreciated by those skilled in the art that the choice of the liquid crystal medium and the temperature used during testing can affect the measured absorption ratio. Accordingly, as set forth in more detail in the Examples, for purposes of the CELL METHOD, absorption ratio measurements are taken at room temperature (73° F.+/−0.5° F. or better) and the liquid crystal medium is Licristal® E7 (which is reported to be a mixture of cyanobiphenyl and cyanoterphenyl liquid crystal compounds).

Once the liquid crystal medium and the photochromic compound are aligned, the cell assembly is placed on an optical bench (which is described in more detail in the Examples). To obtain the average absorption ratio in the activated state, activation of the photochromic compound is achieved by exposing the photochromic compound to UV radiation for a time sufficient to reach a saturated or near saturated state (that is, a state wherein the absorption properties of the photochromic compound do not substantially change over the interval of time during which the measurements are made). Absorption measurements are taken over a period of time (typically 10 to 300 seconds) at 3 second intervals for light that is linearly polarized in a plane perpendicular to the optical bench (referred to as the 0° polarization plane or direction) and light that is linearly polarized in a plane that is parallel to the optical bench (referred to as the 90° polarization plane or direction) in the following sequence: 0°, 90°, 90°, 0° etc. The absorbance of the linearly polarized light by the cell is measured at each time interval for all of the wavelengths tested and the unactivated absorbance (i.e., the absorbance of the cell with the liquid crystal material and the unactivated photochromic compound) over the same range of wavelengths is subtracted to obtain absorption spectra for the photochromic compound in each of the 0° and 90° polarization planes to obtain an average difference absorption spectrum in each polarization plane for the photochromic compound in the saturated or near-saturated state.

For example, with reference to FIG. 1, there is shown the average difference absorption spectrum (generally indicated 10) in one polarization plane that was obtained for a photochromic compound according to one non-limiting embodiment disclosed herein. The average absorption spectrum (generally indicated 11) is the average difference absorption spectrum obtained for the same photochromic compound in the orthogonal polarization plane.

Based on the average difference absorption spectra obtained for the photochromic compound, the average absorption ratio for the photochromic compound is obtained as follows. The absorption ratio of the photochromic compound at each wavelength in a predetermined range of wavelengths corresponding to $\lambda_{max\text{-}vis}+/-5$ nanometers (generally indicated as 14 in FIG. 1), wherein $\lambda_{max\text{-}vis}$ is the wavelength at which the photochromic compound had the highest average absorbance in any plane, is calculated according to the following equation:

$$AR_{\lambda_i} = Ab^1_{\lambda_i}/Ab^2_{\lambda_i} \qquad \text{Eq. 1}$$

wherein, $AR_{\lambda_i}$ is the absorption ratio at wavelength $\lambda_i$, $Ab^1_{\lambda_i}$ is the average absorption at wavelength $\lambda_i$ in the polarization direction (i.e., 0° or 90°) having the higher absorbance, and $Ab^2_{\lambda_i}$ is the average absorption at wavelength $\lambda_i$ in the remaining polarization direction. As previously discussed, the "absorption ratio" refers to the ratio of the absorbance of radiation linearly polarized in a first plane to the absorbance of the same wavelength radiation linearly polarized in a plane orthogonal to the first plane, wherein the first plane is taken as the plane with the highest absorbance.

The average absorption ratio ("AR") for the photochromic compound is then calculated by averaging the individual absorption ratios obtained for the wavelengths within the predetermined range of wavelengths (i.e., $\lambda_{max\text{-}vis}+/-5$ nanometers) according to the following equation:

$$AR = (\Sigma AR_{\lambda_i})/n_i \qquad \text{Eq. 2}$$

wherein, AR is average absorption ratio for the photochromic compound, $AR_{\lambda_i}$ are the individual absorption ratios (as determined above in Eq. 1) for each wavelength within the predetermined the range of wavelengths (i.e., $\lambda_{max\text{-}vis}+/-5$ nanometers), and $n_i$ is the number of individual absorption ratios averaged.

As previously discussed, conventional thermally reversible photochromic compounds are adapted to switch from a first state to a second state in response to actinic radiation, and to revert back to the first state in response to thermal energy. More specifically, conventional thermally reversible, photochromic compounds are capable of transforming from one isomeric form (for example and without limitation, a closed form) to another isomeric form (for example and without limitation, an open form) in response to actinic radiation, and reverting back to the closed form when exposed to thermal energy. However, as previously discussed, generally conventional thermally reversible photochromic compounds do not strongly demonstrate dichroism.

As discussed above, non-limiting embodiments disclosed herein provide a thermally reversible photochromic compound having an average absorption ratio greater than 2.3 in at least one state as determined according to CELL METHOD. Thus, the thermally reversible photochromic compound according to this non-limiting embodiment can display both useful photochromic properties and useful dichroic properties. That is, the thermally reversible, photochromic compound can be a thermally reversible, photochromic-dichroic compound. As used herein with respect to the photochromic compounds described herein, the term "photochromic-dichroic" means displaying both photochromic and dichroic properties under certain conditions, which properties are at least detectable by instrumentation.

According to other non-limiting embodiments, the thermally reversible photochromic compounds can be thermally reversible photochromic-dichroic compounds having an average absorption ratio ranging from 4 to 20, from 3 to 30, or from 2.5 to 50 in at least one state as determined according to CELL METHOD. It will be appreciated by those skilled in the art that the higher the average absorption ratio of the photochromic compound the more linearly polarizing the photochromic compound will be. Therefore, according to various non-limiting embodiments, the thermally reversible photochromic compounds can have any average absorption ratio required to achieve a desired level of linear polarization.

Another non-limiting embodiment provides a thermally reversible, photochromic compound that is free of oxazines and adapted to have at least a first state and a second state, wherein the photochromic compound has an average absorption ratio of at least 1.5 in at least one state as determined according to CELL METHOD. Further, according to this non-limiting embodiment, the average average absorption ratio can range from 1.5 to 50 in at least one state as determined according to CELL METHOD.

Other non-limiting embodiments disclosed herein provide a photochromic compound, which may be a thermally reversible photochromic compound, comprising: (a) at least one photochromic group (PC) chosen from pyrans, oxazines, and fulgides; and (b) at least one lengthening agent attached to the at least one photochromic group, wherein the lengthening agent (L) is represented by the following Formula I (which is described in detail below):

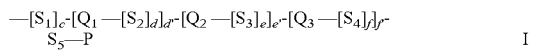
$S_5$—P      I

As used herein, the term "attached" means directly bonded to or indirectly bonded to through another group. Thus, for example, according to various non-limiting embodiments disclosed herein, L can be directly bonded to PC as a substituent on PC, or L can be a substituent on another group (such as a group represented by $R^1$, which is discussed below) that is directly bonded to PC (i.e., L is indirectly bonded to PC). Although not limiting herein, according to various non-limiting embodiments, L can be attached to PC so as to extend or lengthen PC in an activated state such that the absorption ratio of the extended PC (i.e., the photochromic compound) is enhanced as compared to PC alone. Although not limiting herein, according to various non-limiting embodiments, the location of attachment of L on PC can be chosen such that L lengthens PC in at least one of a direction parallel to or a direction perpendicular to a theoretical transitional dipole moment of the activated form of PC. As used herein the term "theoretical transitional dipole moment" refers to transient dipolar polarization created by interaction of electromagnetic radiation with the molecule. See, for example, *IUPAC Compendium of Chemical Technology*, 2$^{nd}$ Ed., International Union of Pure and Applied Chemistry (1997).

With reference to Formula I above, each $Q_1$, $Q_2$, and $Q_3$ can be independently chosen for each occurrence from: a divalent group chosen from an unsubstituted or a substituted aromatic group, an unsubstituted or a substituted alicyclic group, an unsubstituted or a substituted heterocyclic group, and mixtures thereof, wherein substituents are chosen from: a group represented by P (as set forth below), aryl, thiol, amide, liquid crystal mesogens, halogen, $C_1$-$C_{18}$alkoxy, poly($C_1$-$C_{18}$ alkoxy), amino, amino($C_1$-$C_{18}$)alkylene, $C_1$-$C_{18}$alkylamino, di-($C_1$-$C_{18}$)alkylamino, $C_1$-$C_{18}$ alkyl, $C_2$-$C_{18}$ alkene, $C_2$-$C_{18}$ alkyne, $C_1$-$C_{18}$ alkyl($C_1$-$C_{18}$)alkoxy, $C_1$-$C_{18}$ alkoxycarbonyl, $C_1$-$C_{18}$ alkylcarbonyl, $C_1$-$C_{18}$ alkyl carbonate, aryl carbonate, $C_1$-$C_{18}$ acetyl, $C_3$-$C_{10}$ cycloalkyl, $C_3$-$C_{10}$ cycloalkoxy, isocyanato, amido, cyano, nitro, a straight-chain or branched $C_1$-$C_{18}$ alkyl group that is mono-substituted with cyano, halo, or $C_1$-$C_{18}$ alkoxy, or poly-substituted with halo, and a group represented by one of the following formulae: -M(T)$_{(t-1)}$ and -M(OT)$_{(t-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and t is the valence of M. As used herein, the prefix "poly" means at least two.

As discussed above, $Q_1$, $Q_2$, and $Q_3$ can be independently chosen for each occurrence from a divalent group, such as an unsubstituted or a substituted aromatic group, unsubstituted or substituted heterocyclic group, and an unsubstituted or substituted alicylic group. Non-limiting examples of useful aromatic groups include: benzo, naphtho, phenanthro, biphenyl, tetrahydro naphtho, terphenyl, and anthraceno.

As used herein the term "heterocyclic group" means a compound having a ring of atoms, wherein at least one atom forming the ring is different than the other atoms forming the ring. Further, as used herein, the term heterocyclic group specifically excludes fused heterocyclic groups. Non-limiting examples of suitable heterocyclic groups from which $Q_1$, $Q_2$, and $Q_3$ can be chosen include: isosorbitol, dibenzofuro, dibenzothieno, benzofuro, benzothieno, thieno, furo, dioxino, carbazolo, anthranilyl, azepinyl, benzoxazolyl, diazepinyl, dioazlyl, imidazolidinyl, imidazolyl, imidazolinyl, indazolyl, indoleninyl, indolinyl, indolizinyl, indolyl, indoxazinyl, isobenzazolyl, isoindolyl, isooxazolyl, isooxazyl, isopyrroyl, isoquinolyl, isothiazolyl, morpholino, morpholinyl, oxadiazolyl, oxathiazolyl, oxathiazyl, oxathiolyl, oxatriazolyl, oxazolyl, piperazinyl, piperazyl, piperidyl, purinyl, pyranopyrrolyl, pyrazinyl, pyrazolidinyl, pyrazolinyl, pyrazolyl, pyrazyl, pyridazinyl, pyridazyl, pyridyl, pyrimidinyl, pyrimidyl, pyridenyl, pyrrolidinyl, pyrrolinyl, pyrroyl, quinolizinyl, quinuclidinyl, quinolyl, thiazolyl, triazolyl, triazyl, N-arylpiperazino, aziridino, arylpiperidino, thiomorpholino, tetrahydroquinolino, tetrahydroisoquinolino, pyrryl, unsubstituted, mono- or di-substituted $C_4$-$C_{18}$ spirobicyclic amines, and unsubstituted, mono- or di-substituted $C_4$-$C_{18}$ spirotricyclic amines.

As discussed above, according to various non-limiting embodiments $Q_1$, $Q_2$, and $Q_3$ can be chosen from mono- or di-substituted $C_4$-$C_{18}$ spirobicyclic amine and $C_4$-$C_{18}$ spirotricyclic amine. Non-limiting examples of suitable substituents include aryl, $C_1$-$C_6$ alkyl, $C_1$-$C_6$ alkoxy or phenyl($C_1$-$C_6$)alkyl. Specific non-limiting examples of mono- or di-substituted spirobicyclic amines include: 2-azabicyclo [2.2.1]hept-2-yl; 3-azabicyclo[3.2.1]oct-3-yl; 2-azabicyclo [2.2.2]oct-2-yl; and 6-azabicyclo[3.2.2]nonan-6-yl. Specific non-limiting examples of mono- or di-substituted tricyclic amines include: 2-azatricyclo[3.3.1.1(3,7)]decan-2-yl; 4-benzyl-2-azatricyclo[3.3.1.1(3,7)]decan-2-yl; 4-methoxy-6-methyl-2-azatricyclo[3.3.1.1(3,7)]decan-2-yl; 4-azatricyclo[4.3.1.1(3,8)]undecan-4-yl; and 7-methyl-4-azatricyclo [4.3.1.1(3,8)]undecan-4-yl.

Examples of alicyclic groups from which $Q_1$, $Q_2$, and $Q_3$ can be chosen include, without limitation, cyclohexyl, cyclopropyl, norbornenyl, decalinyl, adamantanyl, bicyclooctane, per-hydrofluorene, and cubanyl.

With continued reference to Formula I, and each $S_1$, $S_2$, $S_3$, $S_4$, and $S_5$ is independently chosen for each occurrence from a spacer unit chosen from:

(1) —$(CH_2)_g$—, —$(CF_2)_h$—, —$Si(CH_2)_g$—, —$(Si[(CH_3)_2]O)_h$—, wherein g is independently chosen for each occurrence from 1 to 20; h is chosen from 1 to 16;

(2) —N(Z)-, —C(Z)=C(Z)-, —C(Z)=N—, —C(Z')-C(Z')-, wherein Z is independently chosen for each occurrence from hydrogen, $C_1$-$C_6$ alkyl, cycloalkyl and aryl, and Z' is independently chosen for each occurrence from $C_1$-$C_6$ alkyl, cycloalkyl and aryl; and (3) —O—, —C(O)—, —C≡C—, —N=N—, —S—, —S(O)—, —S(O)(O)—, straight-chain or branched $C_1$-$C_{24}$ alkylene residue, said $C_1$-$C_{24}$ alkylene residue being unsubstituted, mono-substituted by cyano or halo, or poly-substituted by halo;

provided that when two spacer units comprising heteroatoms are linked together the spacer units are linked so that heteroatoms are not directly linked to each other and when $S_1$ and $S_5$ are linked to PC and P, respectively, they are linked so that two heteroatoms are not directly linked to each other. As used herein the term "heteroatom" means atoms other than carbon or hydrogen.

According to various non-limiting embodiments disclosed herein, in Formula I, c, d, e, and f each can be independently chosen from an integer ranging from 1 to 20, inclusive; and d', e' and f' each can be independently chosen from 0, 1, 2, 3, and 4, provided that the sum of d'+e'+f' is at least 1. According to other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f' is at least 2. According to still other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f' is at least 3. According to still other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f' is at least 1.

Further, in Formula I, P can be chosen from: aziridinyl, hydrogen, hydroxy, aryl, alkyl, alkoxy, amino, alkylamino, alkylalkoxy, alkoxyalkoxy, nitro, polyalkyl ether, $(C_1$-$C_6)$ alkyl$(C_1$-$C_6)$alkoxy$(C_1$-$C_6)$alkyl, polyethyleneoxy, polypropyleneoxy, ethylene, acrylate, methacrylate, 2-chloroacrylate, 2-phenylacrylate, acryloylphenylene, acrylamide, methacrylamide, 2-chloroacrylamide, 2-phenylacrylamide, epoxy, isocyanate, thiol, thioisocyanate, itaconic acid ester, vinyl ether, vinyl ester, a styrene derivative, siloxane, main-chain and side-chain liquid crystal polymers, ethyleneimine derivatives, maleic acid derivatives, fumaric acid derivatives, unsubstituted cinnamic acid derivatives, cinnamic acid derivatives that are substituted with at least one of methyl, methoxy, cyano and halogen, and substituted and unsubstituted chiral and non-chiral monovalent or divalent groups chosen from steroid radicals, terpenoid radicals, alkaloid radicals and mixtures thereof, wherein the substituents are independently chosen from alkyl, alkoxy, amino, cycloalkyl, alkylalkoxy, fluoroalkyl, cyanoalkyl, cyanoalkoxy and mixtures thereof.

According to various non-limiting embodiments disclosed herein, when P is a polymerizable group, the polymerizable group can be any functional group adapted to participate in a polymerization reaction. Non-limiting examples of polymerization reactions include those described in the definition of "polymerization" in *Hawley's Condensed Chemical Dictionary Thirteenth Edition*, 1997, John Wiley & Sons, pages 901-902, which disclosure is incorporated herein by reference. For example, although not limiting herein, polymerization reactions include: "addition polymerization," in which free radicals are the initiating agents that react with the double bond of a monomer by adding to it on one side at the same time producing a new free electron on the other side; "condensation polymerization," in which two reacting molecules combine to form a larger molecule with elimination of a small molecule, such as a water molecule; and "oxidative coupling polymerization." Further, non-limiting examples of polymerizable groups include hydroxy, acryloxy, methacryloxy, 2-(acryloxy)ethylcarbamyl, 2-(methacryloxy)ethylcarbamyl, isocyanate, aziridine, allylcarbonate, and epoxy, e.g., oxiranylmethyl.

According to one specific, non-limiting embodiment, P can be chosen from a main-chain or a side-chain liquid crystal polymer and a liquid crystal mesogen. As used herein, the term liquid crystal "mesogen" means rigid rod-like or disc-like liquid crystal molecules. Further, as used herein the term "main-chain liquid crystal polymer" refers to a polymer having liquid crystal mesogens within the backbone (i.e., the main chain) structure of the polymer. As used herein the term "side-chain liquid crystal polymer" refers to a polymer having liquid crystal mesogens attached to the polymer at the side chains. Although not limiting herein, generally, the mesogens are made up of two or more aromatic rings that restrict the movement of a liquid crystal polymer. Examples of suitable rod-like liquid crystal mesogens include without limitation: substituted or unsubstituted aromatic esters, substituted or unsubstituted linear aromatic compounds, and substituted or unsubstituted terphenyls.

According to another specific, non-limiting embodiment, P can be chosen from a steroid radical, for example and without limitation, a cholesterolic compound.

As is discussed above, various non-limiting embodiments disclosed herein provide a photochromic compound comprising (a) a photochromic group (PC) chosen from pyrans, oxazines, and fulgides, and (b) at least one lengthening agent (L) represented by Formula I (above) attached to PC. According to various non-limiting embodiments disclosed herein, PC can be a thermally reversible photochromic group chosen from thermally reversible pyrans, thermally reversible oxazines, and thermally reversible fulgides. According to other non-limiting embodiments, which are discussed herein below in more detail, PC can be a non-thermally reversible, photochromic group. As used herein, the term "non-thermally reversible" means adapted to switch from a first state to a second state in response to actinic radiation, and to revert back to the first state in response to actinic radiation.

Non-limiting examples of thermally reversible photochromic pyrans from which PC can be chosen and that can be used in conjunction with various non-limiting embodiments disclosed herein include benzopyrans, naphthopyrans, e.g., naphtho[1,2-b]pyrans, naphtho[2,1-b]pyrans, indeno-fused naphthopyrans, such as those disclosed in U.S. Pat. No. 5,645,767, and heterocyclic-fused naphthopyrans, such as those disclosed in U.S. Pat. Nos. 5,723,072, 5,698,141, 6,153, 126, and 6,022,497, which are hereby incorporated by reference; spiro-9-fluoreno[1,2-b]pyrans; phenanthropyrans; quinopyrans; fluoroanthenopyrans; spiropyrans, e.g., spiro (benzindoline)naphthopyrans, spiro(indoline)benzopyrans, spiro(indoline)naphthopyrans, spiro(indoline)quinopyrans and spiro(indoline)pyrans. More specific examples of naphthopyrans and the complementary organic photochromic substances are described in U.S. Pat. No. 5,658,501, which are hereby specifically incorporated by reference herein. Spiro (indoline)pyrans are also described in the text, *Techniques in Chemistry*, Volume III, "Photochromism", Chapter 3, Glenn H. Brown, Editor, John Wiley and Sons, Inc., New York, 1971, which is hereby incorporated by reference.

Non-limiting examples of thermally reversible photochromic oxazines from which PC can be chosen and that can be used in conjunction with various non-limiting embodiments disclosed herein include benzoxazines, naphthoxazines, and spiro-oxazines, e.g., spiro(indoline)naphthoxazines, spiro (indoline)pyridobenzoxazines, spiro(benzindoline)pyridobenzoxazines, spiro(benzindoline)naphthoxazines, spiro(indoline)benzoxazines, spiro(indoline)fluoranthenoxazine, and spiro(indoline)quinoxazine.

Non-limiting examples of thermally reversible photochromic fulgides from which PC can be chosen and that can be used in conjunction with various non-limiting embodiments disclosed herein include: fulgimides, and the 3-furyl and 3-thienyl fulgides and fulgimides, which are disclosed in U.S. Pat. No. 4,931,220 (which are hereby specifically incorporated by reference) and mixtures of any of the aforementioned photochromic materials/compounds.

According to one specific, non-limiting embodiment, wherein the photochromic group comprises at least two PCs, the PCs can be linked to one another via linking group substituents on the individual PCs. For example, the PCs can be polymerizable photochromic groups or photochromic groups that are adapted to be compatible with a host material ("compatibilized photochromic group"). Non-limiting examples of polymerizable photochromic groups from which PC can be chosen and that are useful in conjunction with various non-limiting embodiments disclosed herein are disclosed in U.S. Pat. No. 6,113,814, which is hereby specifically incorporated by reference herein. Non-limiting examples of compatibilized photochromic groups from which PC can be chosen and that are useful in conjunction with various non-limiting embodiments disclosed herein are disclosed in U.S. Pat. No. 6,555,028, which is hereby specifically incorporated by reference herein.

Other suitable photochromic groups and complementary photochromic groups are described in U.S. Pat. No. 6,080,338 at column 2, line 21 to column 14, line 43; U.S. Pat. No. 6,136,968 at column 2, line 43 to column 20, line 67; U.S. Pat. No. 6,296,785 at column 2, line 47 to column 31, line 5; U.S. Pat. No. 6,348,604 at column 3, line 26 to column 17, line 15; U.S. Pat. No. 6,353,102 at column 1, line 62 to column 11, line 64; and U.S. Pat. No. 6,630,597 at column 2, line 16 to column 16, line 23; the disclosures of the aforementioned patents are incorporated herein by reference.

Additionally, as previously discussed, according to various non-limiting embodiments disclosed herein, the photochromic compound comprising the at least one photochromic group (PC) and the at least one lengthening agent (L) represented by Formula I (above) and attached to PC, can be a photochromic-dichroic compound. For example, according to various non-limiting embodiments the photochromic compound can be a photochromic-dichroic compound having an average absorption ratio greater than 2.3 in an activated state as determined according to the CELL METHOD (described above). According to other non-limiting embodiments, the photochromic compound can be a photochromic-dichroic compound having an average absorption ratio ranging from 4 to 20, 3 to 30, or 2.5 to 50 in an activated state as determined according to CELL METHOD.

Further, in addition to at least one lengthening agent (L), the photochromic compounds according to various non-limiting embodiments disclosed herein can further comprise at least one group represented by $R^x$ that is directly bonded to PC. Further, although not required, as previously discussed, according to various non-limiting embodiments, the at least one lengthening agent (L) can be indirectly bonded to PC through the at least one group represented by $R^1$. That is, according to various non-limiting embodiments, L can be a substituent on at least one group $R^1$ that is bonded to PC.

According to various non-limiting embodiments disclosed herein, $R^1$ can be independently chosen for each occurrence from:

(i) hydrogen, $C_1$-$C_{12}$ alkyl, $C_2$-$C_{12}$ alkylidene, $C_2$-$C_{12}$ alkylidyne, vinyl, $C_3$-$C_7$ cycloalkyl, $C_1$-$C_{12}$ haloalkyl, allyl, halogen, and benzyl that is unsubstituted or mono-substituted with at least one of $C_1$-$C_{12}$ alkyl and $C_1$-$C_{12}$ alkoxy;

(ii) phenyl that is mono-substituted at the para position with at least one substituent chosen from: $C_1$-$C_7$ alkoxy, linear or branched chain $C_1$-$C_{20}$ alkylene, linear or branched chain $C_1$-$C_4$ polyoxyalkylene, cyclic $C_3$-$C_{20}$ alkylene, phenylene, naphthylene, $C_1$-$C_4$ alkyl substituted phenylene, mono- or poly-urethane($C_1$-$C_{20}$)alkylene, mono- or poly-ester($C_1$-$C_{20}$)alkylene, mono- or poly-carbonate($C_1$-$C_{20}$) alkylene, polysilanylene, polysiloxanylene and mixtures thereof, wherein the at least one substituent is connected to an aryl group of a photochromic material;

(iii) —$CH(CN)_2$ and —$CH(COOX_1)_2$, wherein $X_1$ is chosen from at least one of a lengthening agent L represented by Formula I above, hydrogen, $C_1$-$C_{12}$ alkyl that is unsubstituted or mono-substituted with phenyl, phenyl($C_1$-$C_{12}$) alkyl that is mono-substituted with $C_1$-$C_{12}$ alkyl or $C_1$-$C_{12}$ alkoxy, and an aryl group that is unsubstituted, mono- or di-substituted, wherein each aryl substituent is independently chosen from $C_1$-$C_{12}$ alkyl and $C_1$-$C_{12}$ alkoxy;

(iv) —$CH(X_2)(X_3)$, wherein:

(A) $X_2$ is chosen from at least one of a lengthening agent L represented by Formula I above, hydrogen, $C_1$-$C_{12}$ alkyl and an aryl group that is unsubstituted, mono- or di-substituted, wherein each aryl substituent is independently chosen from $C_1$-$C_{12}$ alkyl and $C_1$-$C_{12}$ alkoxy; and (B) $X_3$ is chosen from at least one of —$COOX_1$, —$COX_1$, —$COX_4$, and —$CH_2OX_5$, wherein:

(1) $X_4$ is chosen from at least one of morpholino, piperidino, amino that is unsubstituted, mono- or di-substituted with $C_1$-$C_{12}$ alkyl, and an unsubstituted, mono or di-substituted group chosen from phenylamino and diphenylamino, wherein each substituent is independently chosen from $C_1$-$C_{12}$ alkyl or $C_1$-$C_{12}$ alkoxy; and (2) $X_5$ is chosen from a lengthening agent L represented by Formula I above, hydrogen, —$C(O)X_2$, $C_1$-$C_{12}$ alkyl that is unsubstituted or mono-substituted with ($C_1$-$C_{12}$)alkoxy or phenyl, phenyl($C_1$-$C_{12}$)alkyl that is mono-substituted with ($C_1$-$C_{12}$)alkoxy, and an aryl group that is unsubstituted, mono- or di-substituted, wherein each aryl substituent is independently chosen from $C_1$-$C_{12}$ alkyl and $C_1$-$C_{12}$ alkoxy;

(v) an unsubstituted, mono-, di-, or tri-substituted aryl group, such as phenyl, naphthyl, phenanthryl, or pyrenyl; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl; wherein the substituents are independently chosen for each occurrence from:

(A) a lengthening agent L represented by Formula I above;

(B) —C(O)$X_6$, wherein $X_6$ is chosen from at least one of: a lengthening agent L represented by Formula I above, hydrogen, $C_1$-$C_{12}$ alkoxy, phenoxy that is unsubstituted, mono- or di-substituted with $C_1$-$C_{12}$ alkyl or $C_1$-$C_{12}$ alkoxy, an aryl group that is unsubstituted, mono- or di-substituted with $C_1$-$C_{12}$ alkyl or $C_1$-$C_{12}$ alkoxy, an amino group that is unsubstituted, mono- or di-substituted with $C_1$-$C_{12}$ alkyl, and a phenylamino group that is unsubstituted, mono- or di-substituted with $C_1$-$C_{12}$ alkyl or $C_1$-$C_{12}$ alkoxy;

(C) aryl, haloaryl, $C_3$-$C_7$ cycloalkylaryl, and an aryl group that is mono- or di-substituted with $C_1$-$C_{12}$ alkyl or $C_1$-$C_{12}$ alkoxy;

(D) $C_1$-$C_{12}$ alkyl, $C_3$-$C_7$ cycloalkyl, $C_3$-$C_7$ cycloalkyloxy($C_1$-$C_{12}$)alkyl, aryl($C_1$-$C_{12}$)alkyl, aryloxy($C_1$-$C_{12}$)alkyl, mono- or di-($C_1$-$C_{12}$)alkylaryl($C_1$-$C_{12}$)alkyl, mono- or di-($C_1$-$C_{12}$)alkoxyaryl($C_1$-$C_{12}$)alkyl, haloalkyl, and mono($C_1$-$C_{12}$)alkoxy($C_1$-$C_{12}$)alkyl;

(E) $C_1$-$C_{12}$ alkoxy, $C_3$-$C_7$ cycloalkoxy, cycloalkyloxy($C_1$-$C_{12}$)alkoxy, aryl($C_1$-$C_{12}$)alkoxy, aryloxy($C_1$-$C_{12}$)alkoxy, mono- or di-($C_1$-$C_{12}$)alkylaryl($C_1$-$C_{12}$)alkoxy, and mono- or di-($C_1$-$C_{12}$)alkoxyaryl($C_1$-$C_{12}$)alkoxy;

(F) amido, amino, mono- or di-alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidyl, hydroxy, acryloxy, methacryloxy, and halogen;

(G) —O$X_7$ and —N($X_7$)$_2$, wherein $X_7$ is chosen from:
(1) a lengthening agent L represented by Formula I above, hydrogen, $C_1$-$C_{12}$ alkyl, $C_1$-$C_{12}$acyl, phenyl($C_1$-$C_{12}$)alkyl, mono($C_1$-$C_{12}$)alkyl substituted phenyl($C_1$-$C_{12}$)alkyl, mono($C_1$-$C_{12}$)alkoxy substituted phenyl($C_1$-$C_{12}$)alkyl; $C_1$-$C_{12}$ alkoxy($C_1$-$C_{12}$)alkyl; $C_3$-$C_7$ cycloalkyl; mono($C_1$-$C_{12}$)alkyl substituted $C_3$-$C_7$ cycloalkyl, $C_1$-$C_{12}$ haloalkyl, allyl, benzoyl, mono-substituted benzoyl, naphthoyl or mono-substituted naphthoyl, wherein each of said benzoyl and naphthoyl substituents are independently chosen from $C_1$-$C_{12}$ alkyl, and $C_1$-$C_{12}$ alkoxy;
(2) —CH($X_8$)$X_9$, wherein $X_8$ is chosen from a lengthening agent L represented by Formula I above, hydrogen or $C_1$-$C_{12}$ alkyl; and $X_9$ is chosen from a lengthening agent L represented by Formula I above, —CN, —CF$_3$, or —COO$X_{10}$, wherein $X_{10}$ is chosen from a lengthening agent L represented by Formula I above, hydrogen or $C_1$-$C_{12}$ alkyl;
(3) —C(O)$X_6$; and
(4) tri($C_1$-$C_{12}$)alkylsilyl, tri($C_1$-$C_{12}$)alkoxysilyl, di($C_1$-$C_{12}$)alkyl($C_1$-$C_{12}$ alkoxy)silyl, or di($C_1$-$C_{12}$)alkoxy($C_1$-$C_{12}$ alkyl)silyl;

(H) —S$X_{11}$, wherein $X_{11}$ is chosen from a lengthening agent L represented by Formula I above, $C_1$-$C_{12}$ alkyl, an aryl group that is unsubstituted, or mono- or di-substituted with $C_1$-$C_{12}$ alkyl, $C_1$-$C_{12}$ alkoxy or halogen;

(I) a nitrogen containing ring represented by Formula i:

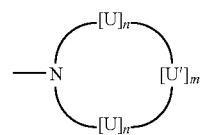

wherein:
(1) n is an integer chosen from 0, 1, 2, and 3, provided that if n is 0, U' is U, and each U is independently chosen for each occurrence from —CH$_2$—, —CH($X_{12}$)—, —C($X_{12}$)$_2$—, —CH($X_{13}$)—, —C($X_{13}$)$_2$—, and —C($X_{12}$)($X_{13}$)—, wherein $X_{12}$ is chosen from a lengthening agent L represented by Formula I above and $C_1$-$C_{12}$ alkyl, and $X_{13}$ is chosen from a lengthening agent L represented by Formula I above, phenyl and naphthyl, and
(2) U' is chosen from U, —O—, —S—, —S(O)—, —NH—, —N($X_{12}$)— or —N($X_{13}$)—, and m is an integer chosen from 1, 2, and 3; and (J) a group represented by one of Formula ii or iii:

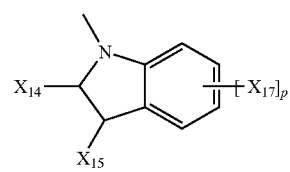

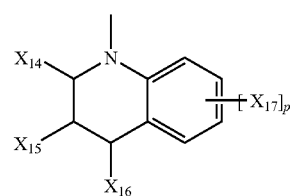

wherein $X_{14}$, $X_{15}$, and $X_{16}$ are independently chosen for each occurrence from a lengthening agent L represented by Formula I above, $C_1$-$C_{12}$ alkyl, phenyl and naphthyl, or $X_{14}$ and $X_{15}$ together form a ring of 5 to 8 carbon atoms; p is an integer chosen from 0, 1, or 2, and $X_{17}$ is independently chosen for each occurrence from a lengthening agent L represented by Formula I above, $C_1$-$C_{12}$ alkyl, $C_1$-$C_{12}$ alkoxy and halogen;

(vi) an unsubstituted or mono-substituted group chosen from pyrazolyl, imidazolyl, pyrazolinyl, imidazolinyl, pyrrolidinyl, phenothiazinyl, phenoxazinyl, phenazinyl and acridinyl, wherein each substituent is independently chosen from a lengthening agent L represented by Formula I above, $C_1$-$C_{12}$ alkyl, $C_1$-$C_{12}$ alkoxy, phenyl, hydroxy, amino and halogen;

(vii) a group represented by one of Formula iv or v:

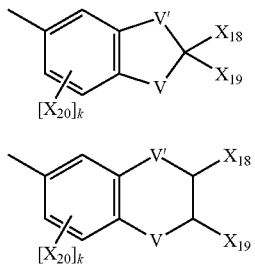

wherein
- (A) V' is independently chosen in each formula from —O—, —CH—, $C_1$-$C_6$ alkylene, and $C_3$-$C_7$ cycloalkylene,
- (B) V is independently chosen in each formula from —O— or —N($X_{21}$)—, wherein $X_{21}$ is from a lengthening agent L represented by Formula I above, hydrogen, $C_1$-$C_{12}$ alkyl, and $C_2$-$C_{12}$ acyl, provided that if V is —N($X_{21}$)—, V' is —$CH_2$—,
- (C) $X_{18}$ and $X_{19}$ are each independently chosen from a lengthening agent L represented by Formula I above, hydrogen and $C_1$-$C_{12}$ alkyl, and
- (D) k is chosen from 0, 1, and 2, and each $X_{20}$ is independently chosen for each occurrence from a lengthening agent L represented by Formula I above, $C_1$-$C_{12}$ alkyl, $C_1$-$C_{12}$ alkoxy, hydroxy and halogen;

(viii) a group represented by Formula vi:

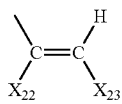

wherein
- (A) $X_{22}$ is chosen from a lengthening agent L represented by Formula I above, hydrogen and $C_1$-$C_{12}$ alkyl, and
- (B) $X_{23}$ is chosen from a lengthening agent L represented by Formula I above or an unsubstituted, mono-, or di-substituted group chosen from naphthyl, phenyl, furanyl and thienyl, wherein each substituent is independently chosen for each occurrence from $C_1$-$C_{12}$ alkyl, $C_1$-$C_{12}$ alkoxy, and halogen;

(ix) —C(O)$X_{24}$, wherein $X_{24}$ is chosen from a lengthening agent L represented by Formula I above, hydroxy, $C_1$-$C_{12}$ alkyl, $C_1$-$C_{12}$ alkoxy, phenyl that is unsubstituted or monosubstituted with $C_1$-$C_{12}$ alkyl or $C_1$-$C_{12}$ alkoxy, amino that is unsubstituted, mono- or di-substituted with at least one of $C_1$-$C_{12}$ alkyl, phenyl, benzyl, and naphthyl;

(x) —$OX_7$ and —N($X_7$)$_2$, wherein $X_7$ is asset forth above;

(xi) —$SX_{11}$, wherein $X_{11}$ is as set forth above;

(xii) the nitrogen containing ring represented by Formula iv, which is set forth above;

(xiii) the group represented by one of Formula v or vi, which are set forth above; and (xiv) immediately adjacent $R^1$ groups together a group represented by one of Formula vii, viii, and ix:

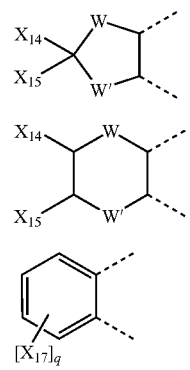

wherein
- (A) W and W' are independently chosen for each occurrence from —O—, —N($X_7$)—, —C($X_{14}$)—, —C($X_{17}$)—, (wherein $X_7$, $X_{14}$, and $X_{17}$ are as set forth above),
- (B) $X_{14}$, $X_{15}$ and $X_{17}$ are as set forth above, and
- (C) q is an integer chosen from 0, 1, 2, 3, and 4.

Another non-limiting embodiment provides a photochromic compound comprising:
- (a) at least one photochromic group chosen from a pyran, an oxazine, and a fulgide; and
- (b) at least one lengthening agent (L) attached to the at least one photochromic group, wherein the at least one lengthening agent is chosen from one of the following compounds listed (and graphically represented) below in Table I.

TABLE I (1) 4-[4-(4-butyl-cyclohexyl)-phenyl]-cyclohexyloxy

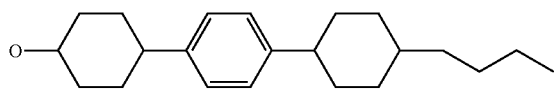

(2) 4''-butyl-[1,1';4',1'']tercyclohexan-4-yloxy

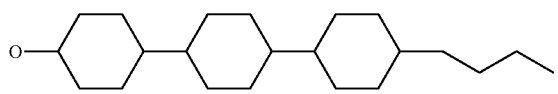

TABLE I-continued (3) 4-[4-(4-butyl-phenyl)-cyclohexyloxycarbonyl]-phenoxy

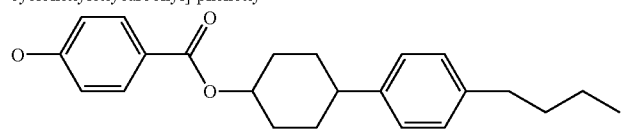

(4) 4'-(4-butyl-benzoyloxy)-biphenyl-4-carbonyloxy

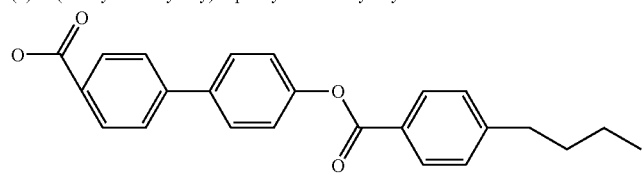

(5) 4-(4-pentyl-phenylazo)-phenylcarbamoyl

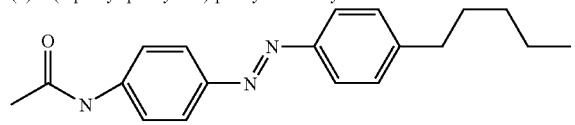

(6) 4-(4-dimethylamino-phenylazo)-phenylcarbamoyl

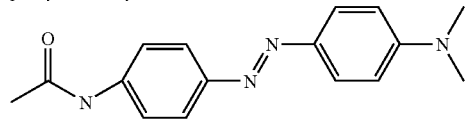

(7) {4-[5-(4-propyl-benzoyloxy)-pyrimidin-2-yl]-phenyl} ester

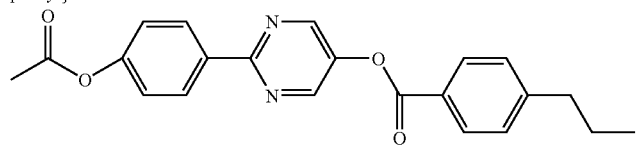

(8) {4-[2-(4'-methyl-biphenyl-4-carbonyloxy)-1,2-diphenyl-ethoxycarbonyl]-phenyl} ester

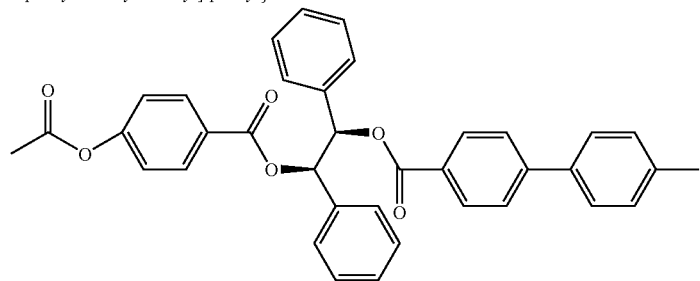

(9) [4-(1,2-diphenyl-2-{3-[4-(4-propyl-benzoyloxy)-phenyl]-acryloyloxy}-ethoxycarbonyl)-phenyl] ester

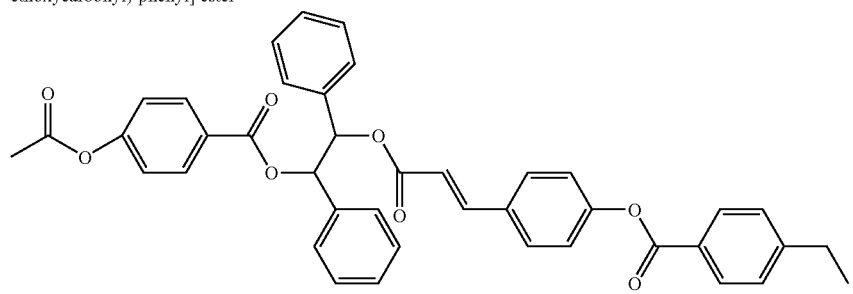

TABLE I-continued
(10) 4-[4-(4-{4-[3-(6-{4-[4-(4-nonyl-benzoyloxy)-
phenoxycarbonyl]-phenoxy}-hexyloxycarbonyl)-
propionyloxy]-benzoyloxy}-benzoyloxy)-phenyl]-
piperazin-1-yl
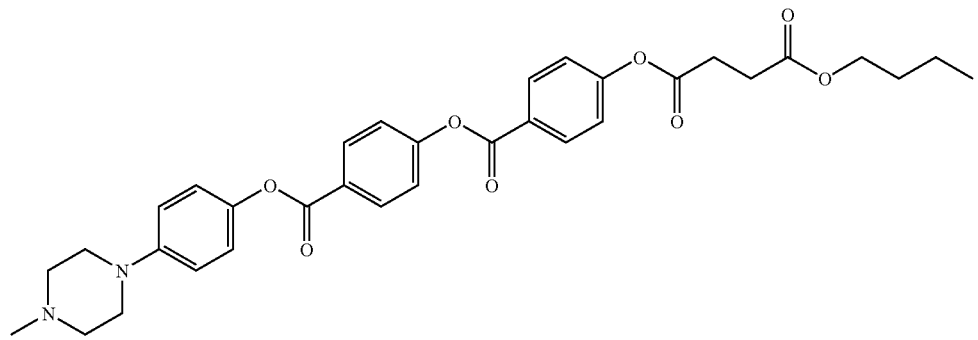
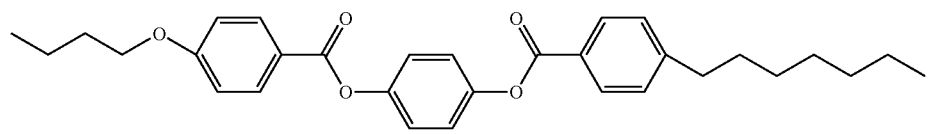
(11) {4-[4-(4-{4-[4-(4-nonyl-benzoyloxy)-
benzoyloxy]-benzoyloxy}-benzoyloxy)-phenyl]-
piperazin-1-yl}
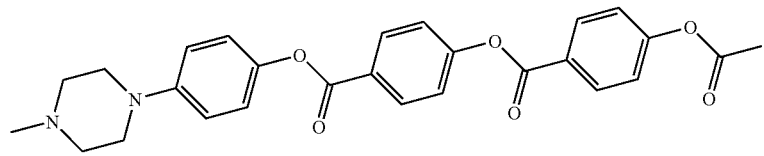
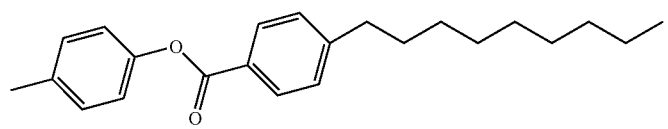
(12) 4-(4'-propyl-biphenyl-4-ylethynyl)-phenyl
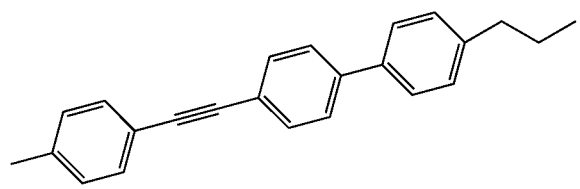
(13) 4-(4-fluoro-phenoxycarbonyloxy)-piperidin-
1-yl
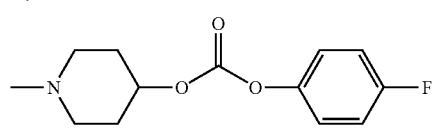

TABLE I-continued

(14) 2-[17-(1,5-dimethyl-hexyl)-10,13-dimethyl-
2,3,4,7,8,9,10,11,12,13,14,15,16,17-
tetradecahydro-1H-cyclopenta[a]phenanthren-3-
yloxy]-indan-5-yl

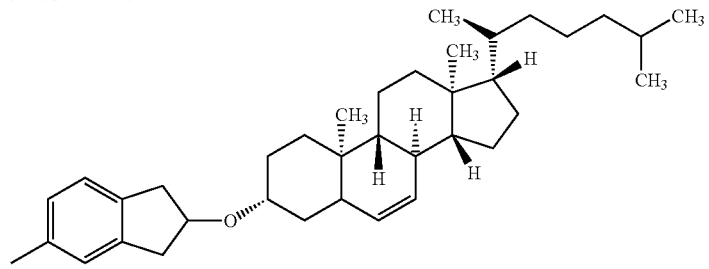

(15) 4-[17-(1,5-dimethyl-hexyl)-10,13-dimethyl-
2,3,4,7,8,9,10,11,12,13,14,15,16,17-
tetradecahydro-1H-cyclopenta[a]phenanthren-3-
yloxycarbonyloxy]-piperidin-1-yl

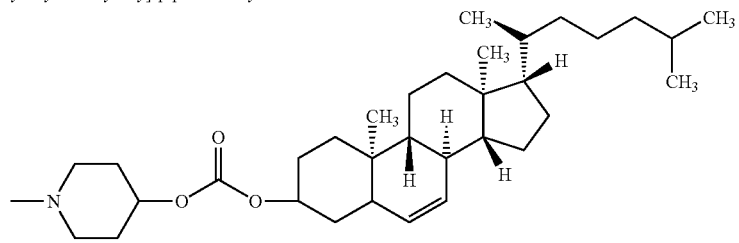

(16) 4-(biphenyl-4-carbonyloxy)-piperidin-1-yl

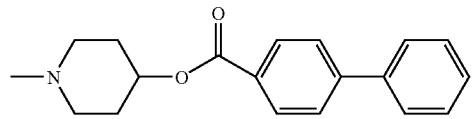

(17) 4-(naphthalene-2-carbonyloxy)-piperidin-1-
yl

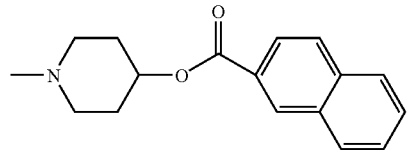

(18) 4-hydroxy-piperidin-1-yl

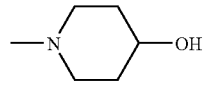

(19) 4-(4-phenylcarbamoyl-phenylcarbamoyl)-
piperidin-1-yl

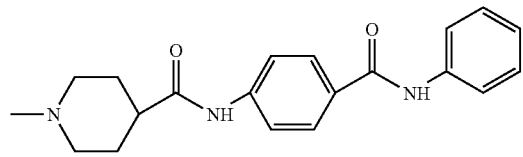

(20) 4-(4-(4-phenylpiperidin-1-yl)-benzoyloxy)-
piperidin-1-yl

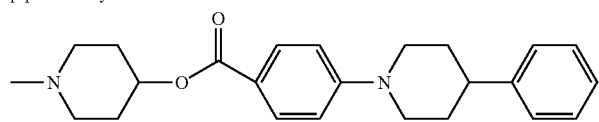

TABLE I-continued

(21) 4-butyl-[1,1';4',1'']terphenyl-4-yl

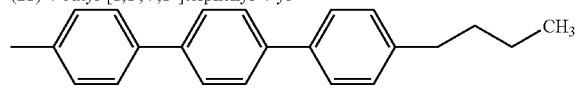

(22) 4-(4-pentadecafluoroheptyloxy-phenylcarbamoyl)-benzyloxy

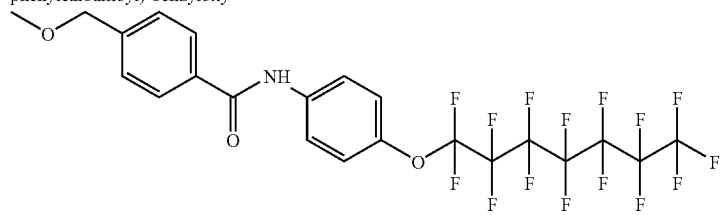

(23) 4-(3-piperidin-4-yl-propyl)-piperidin-1-yl

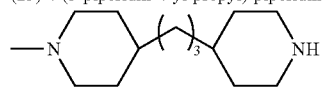

(24) 4-(4-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-benzoyloxy}-phenoxycarbonyl)-phenoxymethyl

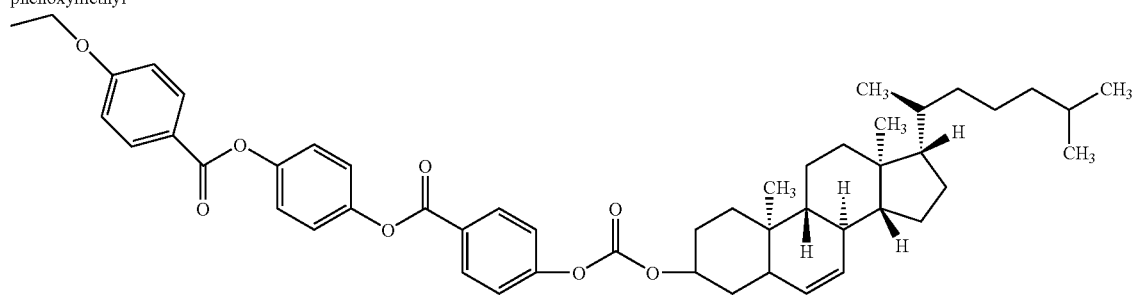

(25) 4-[4-(4-cyclohexyl-phenylcarbamoyl)-benzyloxy]-piperidin-1-yl

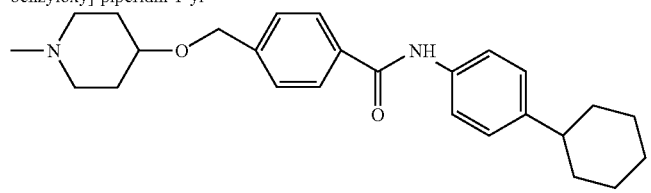

(26) 4-[4-(4-cyclohexyl-phenylcarbamoyl)-benzoyloxy]-piperidin-1-yl

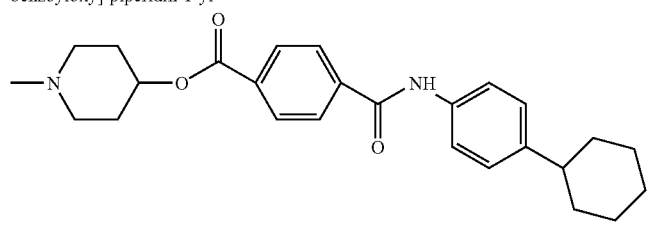

(27) N-{4-[(4-pentyl-benzylidene)-amino]-phenyl}-acetamidyl

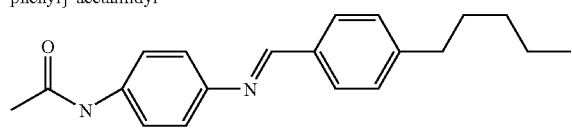

TABLE I-continued

(28) 4-(3-piperidin-4-yl-propyl)-piperidin-1-yl

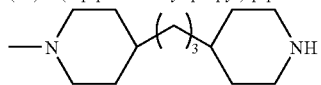

(29) 4-(4-hexyloxy-benzoyloxy)-piperidin-1-yl]

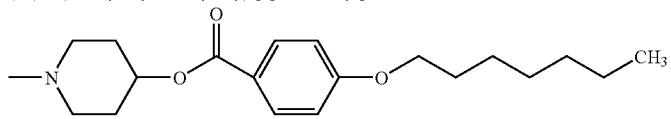

(30) 4-(4'-hexyloxy-biphenyl-4-carbonyloxy)-piperidin-1-yl

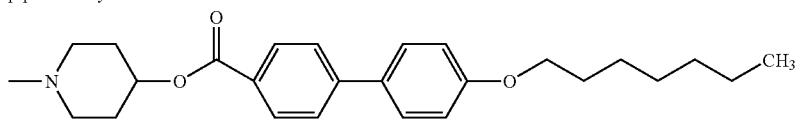

(31) 4-(4-butyl-phenylcarbamoyl)-piperidin-1-yl

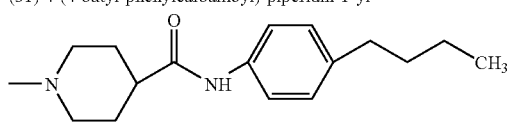

(32) biphenyl-4,4'-dicarboxylic acid bis-[1-Name of PC Group]-piperidin-4-yl] ester

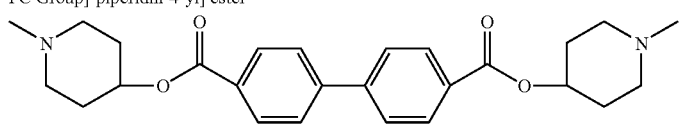

(33) 4-(4-(9-(4-butylphenyl)-2,4,8,10-tetraoxaspiro[5.5]undec-3-yl)phenyl)piperazin-1-yl

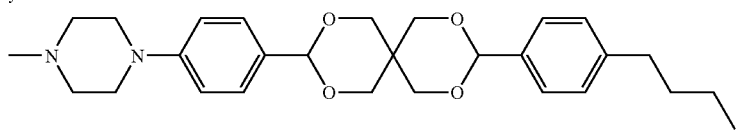

(34) 4-(6-(4-butylphenyl)carbonyloxy-(4,8-dioxabicyclo[3.3.0]oct-2-yl))oxycarbonyl)pheny

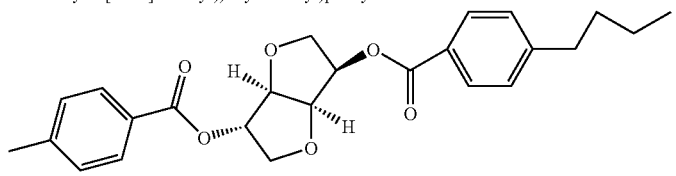

(35) 1-{4-[5-(4-butyl-phenyl)-[1,3]dioxan-2-yl]-phenyl}-4-methyl-piperazin-1-yl

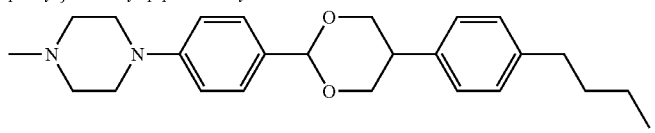

(36) 4-(7-(4-propylphenylcarbonyloxy)bicyclo[3.3.0]oct-2-yl)oxycarbonyl)phenyl

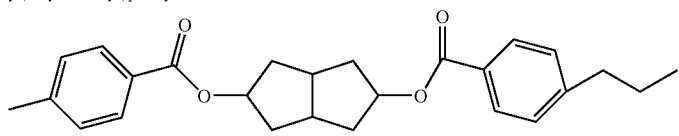

TABLE I-continued

(37) 4-[17-(1,5-dimethyl-hexyl)-10,13-dimethyl-
2,3,4,7,8,9,10,11,12,13,14,15,16,17-
tetradecahydro-1H-cyclopenta[a]phenanthren-3-
yloxycarbonyloxy

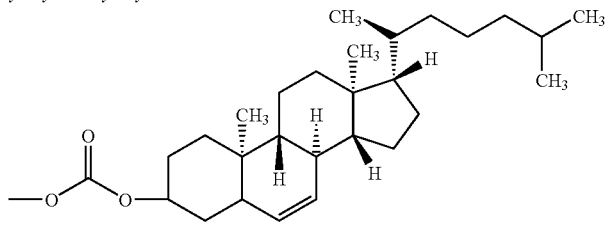

Another non-limiting embodiment disclosed herein provided a photochromic compound represented by Formula II:

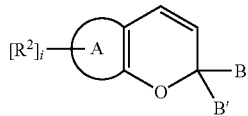

With reference to Formula II, A is an aromatic ring or a fused aromatic ring chosen from: naphthol benzo, phenanthro, fluorantheno, antheno, quinolino, thieno, furo, indolo, indolino, indeno, benzofuro, benzothieno, thiopheno, indeno-fused naphthol heterocyclic-fused naphthol and heterocyclic-fused benzo. Further, according to various non-limiting embodiments, B and B' each can be independently chosen from:

(i) hydrogen, $C_1$-$C_{12}$ alkyl, $C_2$-$C_{12}$ alkylidene, $C_2$-$C_{12}$ alkylidyne, vinyl, $C_3$-$C_7$ cycloalkyl, $C_1$-$C_{12}$ haloalkyl, allyl, halogen, and benzyl that is unsubstituted or mono-substituted with at least one of $C_1$-$C_{12}$ alkyl and $C_1$-$C_{12}$ alkoxy;
(ii) phenyl that is mono-substituted at the para position with at least one substituent chosen from: $C_1$-$C_7$ alkoxy, linear or branched chain $C_1$-$C_{20}$ alkylene, linear or branched chain $C_1$-$C_4$ polyoxyalkylene, cyclic $C_3$-$C_{20}$ alkylene, phenylene, naphthylene, $C_1$-$C_4$ alkyl substituted phenylene, mono- or poly-urethane($C_1$-$C_{20}$)alkylene, mono- or poly-ester($C_1$-$C_{20}$)alkylene, mono- or poly-carbonate($C_1$-$C_{20}$) alkylene, polysilanylene, polysiloxanylene and mixtures thereof, wherein the at least one substituent is connected to an aryl group of a photochromic material;
(iii) —CH(CN)$_2$ and —CH(COOX$_1$)$_2$, wherein $X_1$ is as set forth above;
(iv) —CH(X$_2$)(X$_3$), wherein $X_2$ and $X_3$ are as set forth above;
(v) an unsubstituted, mono-, di-, or tri-substituted aryl group, such as phenyl, naphthyl, phenanthryl, or pyrenyl; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl; wherein the substituents are independently chosen for each occurrence from:
(A) a lengthening agent L represented by Formula I above;
(B) —C(O)X$_6$, wherein $X_6$ is as set forth above;
(C) aryl, haloaryl, $C_3$-$C_7$ cycloalkylaryl, and an aryl group that is mono- or di-substituted with $C_1$-$C_{12}$ alkyl or $C_1$-$C_{12}$ alkoxy;
(D) $C_1$-$C_{12}$ alkyl, $C_3$-$C_7$ cycloalkyl, $C_3$-$C_7$ cycloalkyloxy ($C_1$-$C_{12}$)alkyl, aryl($C_1$-$C_{12}$)alkyl, aryloxy($C_1$-$C_{12}$) alkyl, mono- or di-($C_1$-$C_{12}$)alkylaryl($C_1$-$C_{12}$)alkyl, mono- or di-($C_1$-$C_{12}$)alkoxyaryl($C_1$-$C_{12}$)alkyl, haloalkyl, and mono($C_1$-$C_{12}$)alkoxy($C_1$-$C_{12}$)alkyl;
(E) $C_1$-$C_{12}$ alkoxy, $C_3$-$C_7$ cycloalkoxy, cycloalkyloxy($C_1$-$C_{12}$)alkoxy, aryl($C_1$-$C_{12}$)alkoxy, aryloxy($C_1$-$C_{12}$) alkoxy, mono- or di-($C_1$-$C_{12}$)alkylaryl($C_1$-$C_{12}$)alkoxy, and mono- or di-($C_1$-$C_{12}$)alkoxyaryl($C_1$-$C_{12}$)alkoxy;
(F) amido, amino, mono- or di-alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidyl, hydroxy, acryloxy, methacryloxy, and halogen;
(G) —OX$_7$ and —N(X$_7$)$_2$, wherein X$_7$ is as set forth above;
(H) —SX$_{11}$, wherein X is as set forth above;
(I) the nitrogen containing ring represented by Formula i, which is set forth above; and
(J) the group represented by one of Formula ii or iii, which are set forth above;
(vi) an unsubstituted or mono-substituted group chosen from pyrazolyl, imidazolyl, pyrazolinyl, imidazolinyl, pyrrodlinyl, phenothiazinyl, phenoxazinyl, phenazinyl, and acridinyl, wherein each substituent is independently chosen from a lengthening agent L, $C_1$-$C_{12}$ alkyl, $C_1$-$C_{12}$ alkoxy, phenyl, hydroxy, amino or halogen;
(vii) the group represented by one of Formula iv or v, which are set forth above; and
(viii) the group represented by Formula vi, which is set forth above.

Alternatively, according to various non-limiting embodiments disclosed herein, B and B' together can form: (a) an unsubstituted, mono- or di-substituted fluoren-9-ylidene, wherein each of said fluoren-9-ylidene substituents are chosen from $C_1$-$C_4$ alkyl, $C_1$-$C_4$ alkoxy, fluoro and chloro; (b) a saturated $C_3$-$C_{12}$ spiro-monocyclic hydrocarbon ring, e.g., cyclopropylidene, cyclobutylidene, cyclopentylidene, cyclohexylidene, cycloheptylidene, cyclooctylidene, cyclononylidene, cyclodecylidene cycloundecylidene, cyclododecylidene; (c) a saturated $C_7$-$C_{12}$ spiro-bicyclic hydrocarbon rings, e.g., bicyclo[2.2.1]heptylidene, i.e., norbornylidene, 1,7,7-trimethyl bicyclo[2.2.1]heptylidene, i.e., bornylidene, bicyclo[3.2.1]octylidene, bicyclo[3.3.1]nonan-9-ylidene, bicyclo[4.3.2]undecane; or (d) a saturated $C_7$-$C_{12}$ spiro-tricyclic hydrocarbon rings, e.g., tricyclo[2.2.1.0$^{2,6}$] heptylidene, tricyclo[3.3.1.1$^{3,7}$]decylidene, i.e., adamantylidene, and tricyclo[5.3.1.1$^{2,6}$]dodecylidene. Further according to various non-limiting embodiments discussed in more detail below, B and B' together can form indolino or benzoindolino that is unsubstituted or substituted with at least one group represented by $R^2$.

Referring again to Formula II, according to various non-limiting embodiments, "i" can be an integer chosen from 0 to the total available positions on A, and each $R^2$ can be independently chosen for each occurrence from:
(i) a group represented by B as set forth above;
(ii) —C(O)$X_{24}$, wherein $X_{24}$ is as set forth above;
(iii) —O$X_7$ and —N($X_7$)$_2$, wherein $X_7$ is as set forth above;
(iv) —S$X_{11}$, wherein $X_{11}$ is as set forth above;
(v) the nitrogen containing ring represented by Formula i (above);
(vi) the group represented by one of Formula ii or iii (above);
(vii) immediately adjacent $R^2$ groups together form at a group represented by one of Formula vii, viii, or ix, which are set forth above; and
(viii) a lengthening agent L represented by Formula I (above).

Additionally, according to various non-limiting embodiments disclosed herein, the photochromic compound represented by Formula II comprises at least one lengthening agent (L) represented by Formula I above. As previously discussed, in Formula I, c, d, e, and f each can be independently chosen from an integer ranging from 1 to 20, inclusive; and d', e' and f' each can be independently chosen from 0, 1, 2, 3, and 4, provided that the sum of d'+e'+f' is at least 1. According to other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f' is at least 2. According to still other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f' is at least 3. According to still other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f' is at least 1.

Thus, for example, in Formula II, "i" can be at least 1 and at least one of the $R^2$ groups can be a lengthening agent L. Additionally or alternatively, the photochromic compound can comprise at least one $R^2$ group, at least one B group, or at least one B' group that is substituted with a lengthening agent L. For example, although not limiting herein, in one non-limiting embodiment the photochromic compound represented by Formula II can comprise a B group comprising a phenyl group that is mono-substituted with a lengthening agent L.

Moreover, although not limiting herein, according to various non-limiting embodiments disclosed herein, the lengthening agent (L) can be attached to a photochromic group (e.g., the pyran group of Formula II) at any available position such that L extends or lengthens the photochromic group in an activated state such that the absorption ratio of the extended photochromic group (i.e., the photochromic compound) is enhanced as compared to the unextended photochromic group. Thus, for example and without limitation, according to various non-limiting embodiments wherein the photochromic compound is represented by Formula II, L can be directly bonded to the pyran group, for example, wherein i is at least 1 and $R^2$ is L, or it can be indirectly bonded to the pyran group, for example, as a substituent on an $R^2$ group, B, or B' group such that L extends the pyran group in an activated state such that the absorption ratio of the photochromic compound is enhanced as compared to the unextended pyran group.

Although not limiting herein, in one non-limiting embodiment wherein A is naphtho, the photochromic compound can be a naphtho[1,2-b]pyran as generally shown in Formula III:

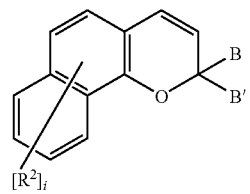

III wherein at least one $R^2$ comprises L and/or at least one B or B' group is substituted with L. For example, according to this non-limiting embodiment, at least one $R^2$ group can be L, and/or at least one B, B', or $R^2$ group can be substituted with L as discussed above.

Although not limiting herein, for example the naphtho[1,2-b]pyran shown in Formula III can be extended, at the 8-position by selecting the $R^2$ substituent in the 8-position (which is indicated below in Formula IV) to L or a group that is substituted with L. Further, it is contemplated that a similar effect to lengthening the naphtho[1,2-b]pyran at the 8-position can be achieved by, for example and without limitation, selecting the $R^2$ substituent in the 7-position to be L or a group substituted with L, provided that substitution lengthens the naphtho[1,2-b]pyran in a direction that is generally parallel to the direction of the 8-position extension. Still further, it is contemplated that the naphtho[1,2-b]pyran can be extended in the general direction of the 8-position extension by selecting two or more of the $R^2$ substituents to be L or a group substituted with L, provided that substitution lengthens the naphtho[1,2-b]pyran in a direction that is generally parallel to the direction of the 8-position extension. However, those skilled in the art will appreciate that the photochromic compounds disclosed herein can be extended at any available position by substitution with a lengthening agent L and/or an $R^2$ group substituted with a lengthening agent L, and/or in any desired direction by numerous combinations of substitutions of available positions with a lengthening agent L or $R^2$ groups substituted with a lengthening agent L.

For example, although not limiting herein, according to various non-limiting embodiments, the photochromic compound can be a naphtho[1,2-b]pyran represented by Formula IV:

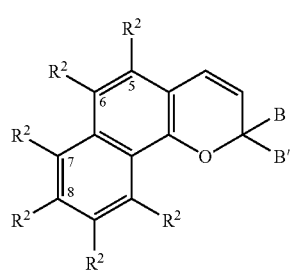

IV wherein:
(a) at least one of: the $R^2$ substituent in the 6-position, the $R^2$ substituent in the 8-position, B and B' comprises a lengthening agent L;

(b) the R² substituent in the 6-position together with the R² substituent in the 5-position forms a group represented by one of Formula x to Formula xiv:

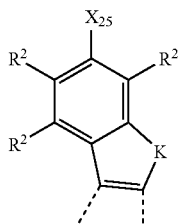

x

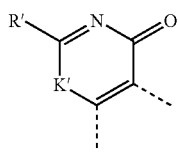

xi

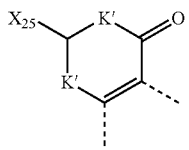

xii

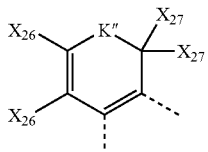

xiii

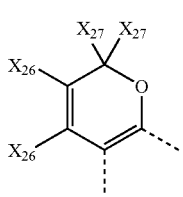

xiv wherein K is chosen from —O—, —S—, —N(X₇)—; and an unsubstituted C or a C substituted with alkyl, hydroxy, alkoxy, oxo, or aryl; K' is —C—, —O—, or —N(X₇)—; K" is chosen from —O— or —N(X₇)—; X₂₅ is a group represented by R² (which is set forth above in detail); X₂₆ can be chosen from hydrogen, alkyl, aryl, or together form benzo or naphtho; and each X₂₇ is chosen from alkyl and aryl or together are oxo; provided that at least one of: the R² substituent in the 8-position, X₂₅, K, K', K", B or B' comprises a lengthening agent L; or (c) the R² substituent in the 6-position together with the R² substituent in the 7-position from an aromatic group chosen from benzeno and naphtho, provided that at least one of: the R² substituent in the 8-position, B and B' comprises a lengthening agent L.

Further, according to one, specific non-limiting embodiment, wherein the R² substituent in the 5-position and the R² substituent in the 6-position (which are shown above in Formula IV) together form an indeno group, and the photochromic compound can be an indeno-fused naphtho[1,2-b]pyran represented by Formula V:

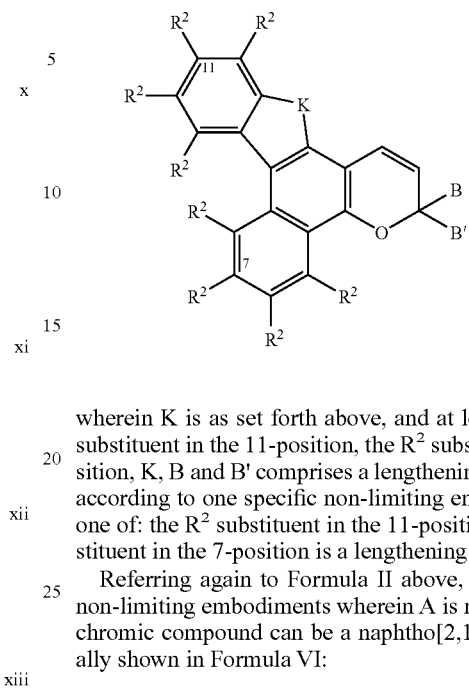

V wherein K is as set forth above, and at least one of: the R² substituent in the 11-position, the R² substituent in the 7-position, K, B and B' comprises a lengthening agent L. Further, according to one specific non-limiting embodiment, at least one of: the R² substituent in the 11-position and the R² substituent in the 7-position is a lengthening agent L.

Referring again to Formula II above, according to other non-limiting embodiments wherein A is naphtho, the photochromic compound can be a naphtho[2,1-b]pyran as generally shown in Formula VI:

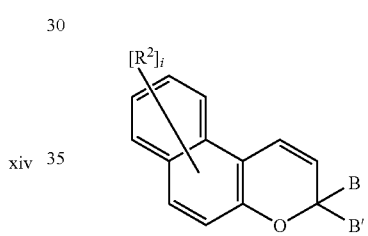

VI wherein at least one of: B, B', or at least one R² comprises a lengthening agent L. Further, as discussed above with respect to naphtho[1,2-b]pyrans, the naphtho[2,1-b]pyrans disclosed herein can be extended at any available position by substitution with L or an R² group substituted L, and/or in any desired direction by numerous combinations of substitutions of available positions with L or R² groups substituted with L.

For example, although not limiting herein, according to various non-limiting embodiments, the photochromic compound can be a naphtho[2,1-b]pyran represented by Formula VII:

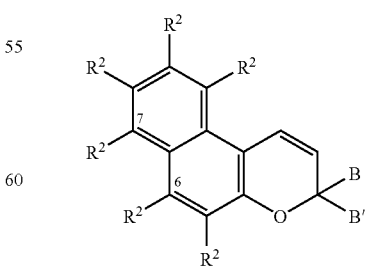

VII wherein at least one of: the R² substituent in the 6-position, the R² substituent in the 7-position, B, and B' comprises a lengthening agent L. More specifically, according to one non-limiting embodiment, at least one of: the $R^2$ substituent in the 6-position and the $R^2$ substituent in the 7-position is a lengthening agent L.

Referring again to Formula II above, according to still other non-limiting embodiments, A can be benzo, the photochromic compound can be a benzopyran represented by Formula VIII:

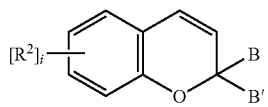

VIII wherein at least one of: B, B', or at least one $R^2$ comprises a lengthening agent L. Further, as discussed above with respect to the naphthopyrans, the benzopyrans disclosed herein can be extended at any available position by substitution with L or an $R^2$ group substituted with L, and/or in any desired direction by numerous combinations of substitutions of available positions with L or R groups substituted with L.

For example, although not limiting herein, according to various non-limiting embodiments, the photochromic compound can be a benzopyran represented by Formula IX:

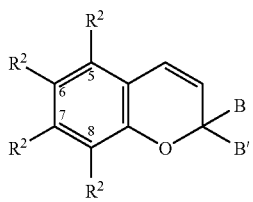

IX wherein:

(a) at least one of: the $R^2$ substituent in the 5-position, the $R^2$ substituent in the 7-position, B or B' comprises a lengthening agent L; or (b) at least one of: the R substituent in the 5-position and the $R^2$ substituent in the 7-position, together with an immediately adjacent $R^2$ substituent, (i.e., the $R^2$ substituent in the 7-position together with an $R^2$ substituent in the 6- or 8-positions, or the $R^2$ substituent in the 5-position together with an R substituent in the 6-position) forms a group represented by Formula x to xiv (set forth above), provided that only one of the $R^2$ substituent in the 5-position and the $R^2$ substituent in the 7-position join together with the $R^2$ substituent in the 6-position, and provided that at least one of: the $R^2$ substituent in the 5-position, the $R^2$ substituent in the 7-position, $X_{25}$, K, K', K", B or B' comprises a lengthening agent L.

Further, the photochromic compound according to various non-limiting embodiments disclosed herein and generally represented by Formula II (above) can have an average absorption ratio of at least 1.5 in an activated state as determined according to CELL METHOD. According to other non-limiting embodiments, the photochromic pyrans can have an average absorption ratio ranging from 4 to 20, 3 to 30, or 2.5 to 50 in an activated state as determined according to CELL METHOD. According to still other non-limiting embodiments, the photochromic pyrans can have an average absorption ratio ranging from 1.5 to 50 in an activated state as determined according to CELL METHOD.

A general reaction sequence for forming a photochromic compound according to various non-limiting embodiments disclosed herein and generally represented by Formula II above, wherein B is an L substituted phenyl group and B' is an unsubstituted phenyl group, is depicted below in Reaction Sequence A.

Reaction Sequence A

Part 1:

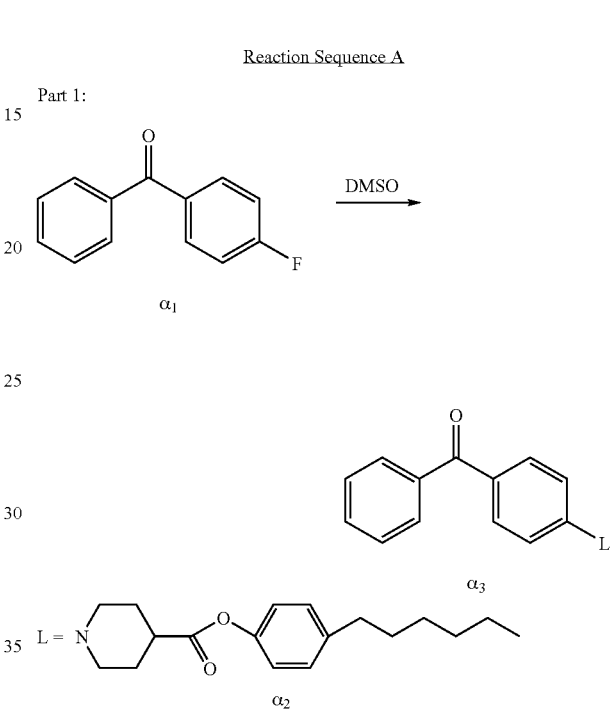

In Reaction Sequence A, Part 1,4-fluorobenzophenone, which is represented by Formula $\alpha_1$, can be reacted under nitrogen in the anhydrous solvent dimethyl sulfoxide (DMSO) with a lengthening agent L represented by Formula $\alpha_2$, to form an L substituted ketone represented by Formula $\alpha_3$. It will be appreciated by those skilled in the art that 4-fluorobenzophenone can either be purchased or prepared by Friedel-Crafts methods known in the art. For example, see the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

Part 2:

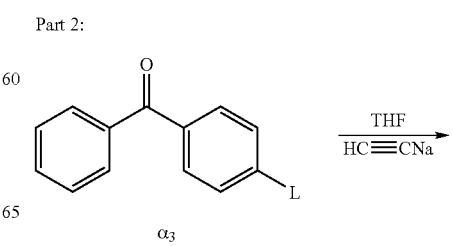

-continued

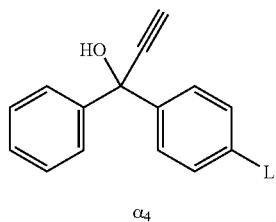

α₄

As depicted in Part 2 of Reaction Sequence A, the L substituted ketone represented by Formula α₃ can be reacted with sodium acetylide in a suitable solvent, such as but not limited to anhydrous tetrahydrofuran (THF), to form the corresponding propargyl alcohol (represented by Formula α₄).

Part 3:

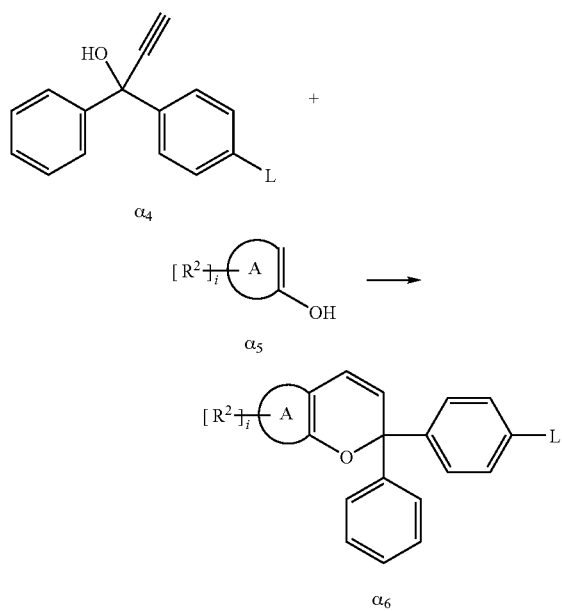

In Part 3 of Reaction Sequence A, the propargyl alcohol represented by Formula α₄ can be coupled with a hydroxy substituted A group (represented by Formula α₅) to form the photochromic pyran represented by Formula α₆ according to one non-limiting embodiment disclosed herein. Optionally, the A group can be substituted with one or more $R^2$ groups, each of which may comprise a lengthening agent L that is the same or different from the remaining L substituents. Non-limiting examples of A and $R^2$ groups that are suitable for use in conjunction with various non-limiting embodiments disclosed herein are set forth above in detail. Non-limiting examples of general reaction sequences for forming hydroxylated A groups that are substituted with at least one lengthening agent L, are shown below in Reaction Sequences B, C, and D.

Although Reaction Sequence A depicts a general reaction sequence for forming a photochromic compound represented by Formula II and having B and B' groups selected from L substituted phenyl and phenyl, it will be appreciated by those skilled in the art that photochromic compounds generally represented by Formula II and having B and B' groups other than those shown in Formula α₆ above and which optionally can be substituted with one or more L groups or one or more $R^2$ groups comprising L, can be prepared from commercially available ketones, or by reaction of an acyl halide with a substituted or unsubstituted material such as naphthalene or a heteroaromatic compound. Non-limiting examples of B and B' substituent groups that are suitable for use in conjunction with various non-limiting embodiments disclosed herein are set forth above in detail.

Reaction Sequences B, C and D depict three different general reaction sequences for forming hydroxylated A groups that are substituted with at least one lengthening agent L, that can be used in the formation of photochromic pyrans according to various non-limiting embodiments disclosed herein. For example, although not limiting herein, as discussed above in Reaction Sequence A, the resulting L substituted hydroxylated A group can be coupled with propargyl alcohol to form a photochromic pyran according to various non-limiting embodiments disclosed herein. Further, as discussed above, optionally, the A group can also be substituted with one or more additional $R^2$ groups, each of which may comprise a lengthening agent L that is the same or different from the remaining Ls.

Reaction Sequence B

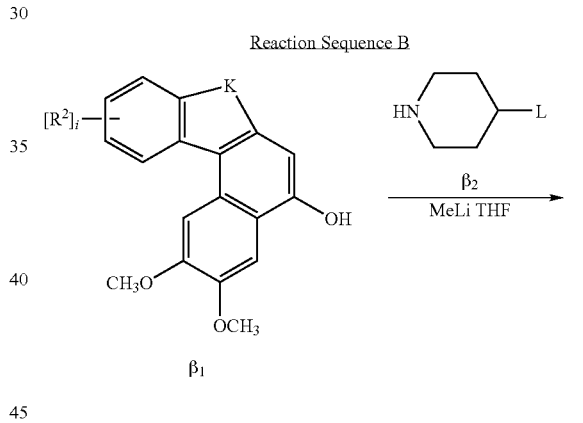

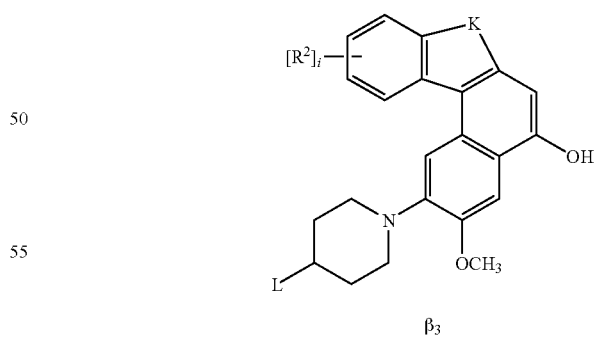

In Reaction Sequence B, the hydroxlylated A group represented by Formula β₁ is reacted with the L substituted piperidine represented by Formula β₂ in the presence of an alkyl lithium, such as but not limited to methyllithium (MeLi), in anhydrous tetrahydrofuran to produce the L substituted $R^2$ group attached to the hydroxylated A group represented by Formula β₃. Further, as indicated above, the A group may also be substituted with one or more additional R² groups, each of which may also comprise a lengthening agent L that is the same or different from the remaining Ls. Further, K can be chosen from —O—, —S—, —N(X₇)— or carbon that is substituted or unsubstituted. For example, K can be a carbon that is di-substituted with methyl or can be substituted with an ethyl group and a hydroxyl group.

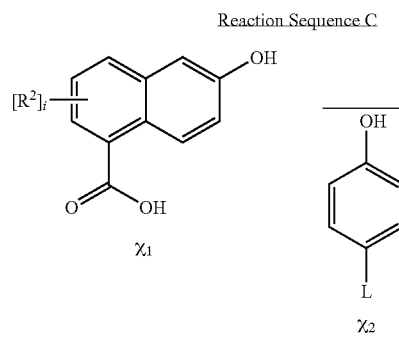

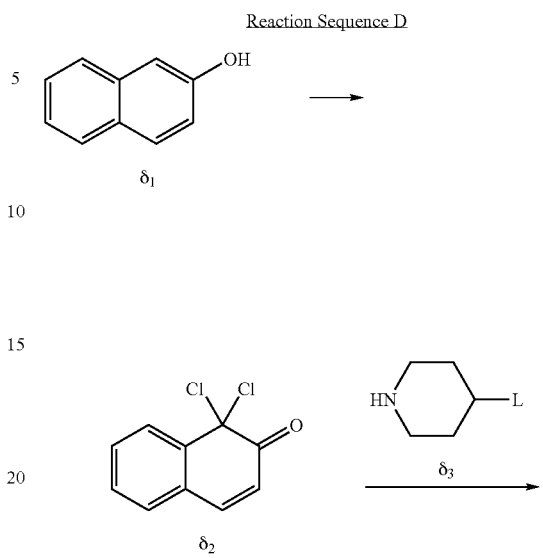

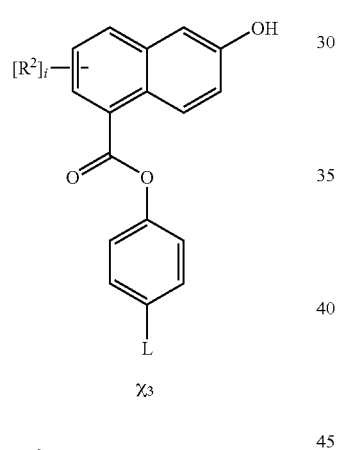

In Reaction Sequence C, the R² substituted hydroxylated A group represented by Formula χ₁ is reacted with the L substituted phenol represented by Formula χ₂ in an esterification reaction in the presence of dicyclohexylcarbodiimide in methylene chloride to produce the L substituted R² group attached to the hydroxylated A group represented by Formula χ₃. Further, as indicated in Reaction Sequence C, the group represented by Formula χ₃ optionally can be substituted with one or more additional R² groups, each of which may also comprise a lengthening agent L that is the same or different from the remaining Ls.

In Reaction Sequence D (below), the hydroxy substituted naphthol represented by Formula δ₁ is reacted with chlorine to form the compound represented by Formula δ₂. The compound represented by Formula δ₂ is reacted with the L substituted piperidine represented by Formula δ₃ to form the material represented by Formula δ₄. The material represented by Formula δ₄ is reduced in a hydrogen atmosphere over a palladium on carbon catalyst to form the L substituted R² group attached to the hydroxylated A group represented by Formula δ₅.

Reaction Sequences E and F demonstrate two different methods of forming a naphthopyran substituted with a lengthening agent L to form a photochromic naphthopyran according to various non-limiting embodiments disclosed herein.

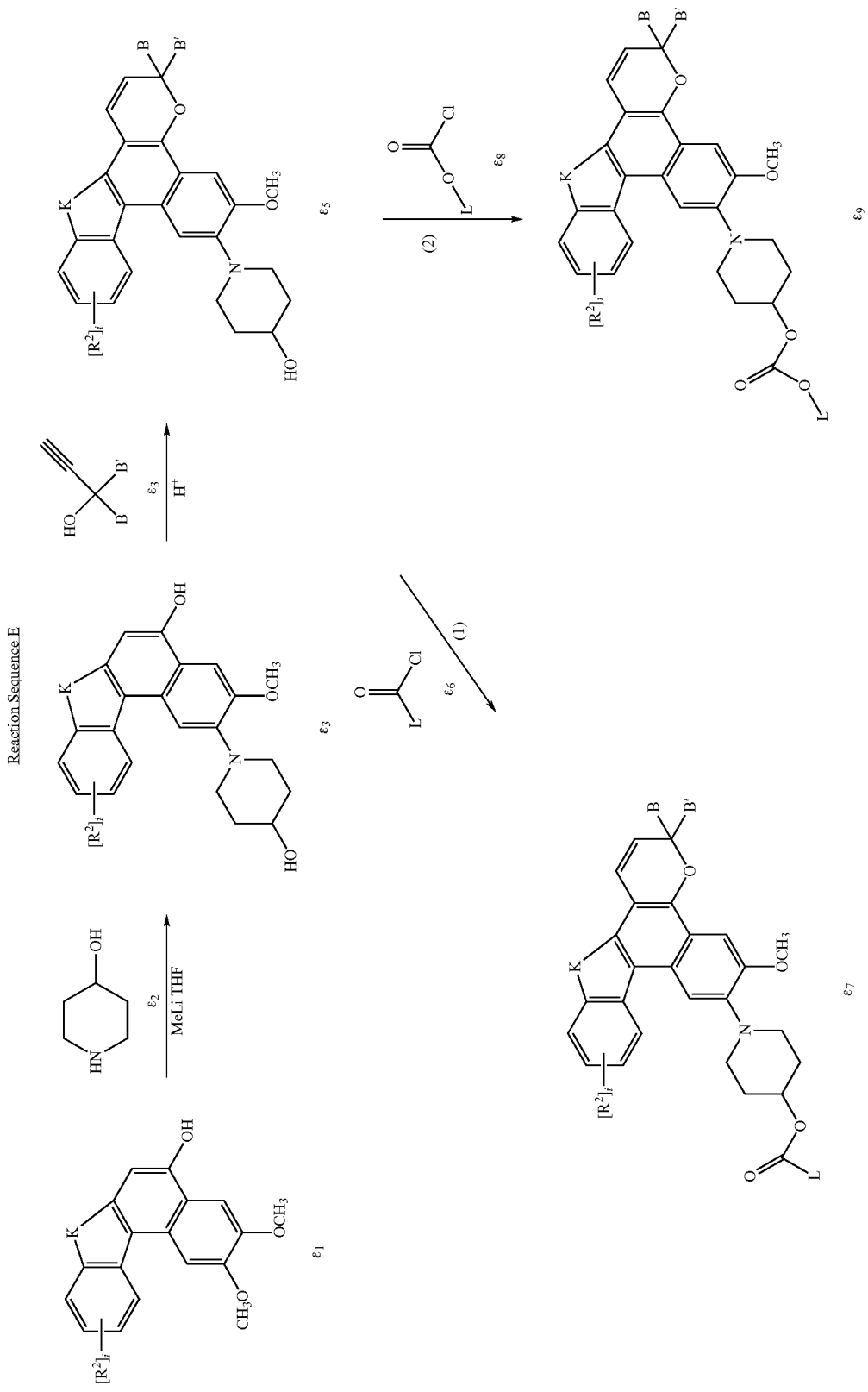

In Reaction Sequence E, the hydroxy substituted A group represented by Formula $\epsilon_1$, which is optionally substituted with at least one $R^2$ group, is reacted with the hydroxy substituted piperidine represented by Formula $\epsilon_2$ in the presence of an alkyl lithium, such as but not limited to methyllithium (MeLi), in anhydrous tetrahydrofuran to produce the 4-hydroxy piperidinyl attached to the hydroxylated A group represented by Formula $\epsilon_3$. The compound represented by Formula $\epsilon_3$ is then coupled with the propargyl alcohol represented by Formula $\epsilon_4$ to form the 4-hydroxy piperidinyl attached to the indeno-fused naphthopyran represented by Formula $\epsilon_5$. The naphthopyran represented by Formula $\epsilon_5$ can be further reacted, as indicated by path (1) Reaction Sequence E, in an acetylation reaction using a tertiary amine, such as but not limited to triethylamine, in a solvent, such as but not limited to methylene chloride, with the L substituted compound represented by Formula $\epsilon_6$ to produce the L substituted piperidinyl attached to the indeno-fused naphthopyran according to one non-limiting embodiment disclosed herein and represented by Formula $\epsilon_7$. Alternatively, as indicated by path (2), the naphthopyran represented by Formula $\epsilon_5$ can be reacted with the L substituted compound represented by Formula $\epsilon_8$ to produce the L substituted piperidinyl attached to the indeno-fused naphthopyran according to one non-limiting embodiment disclosed herein and represented by Formula $\epsilon_9$. Further, as indicated in Reaction Sequence E, the L substituted piperidinyl attached to the indeno-fused naphthopyrans represented by Formula $\epsilon_7$ and Formula $\epsilon_9$ can optionally be substituted with one or more additional $R^2$ groups, each of which may comprise lengthening agent L that is the same or different from the remaining Ls.

In Reaction Sequence F (below), the hydroxylated A group represented by Formula $\phi_1$ is coupled with the propargyl alcohol represented by Formula $\phi_2$ to produce the naphthopyran represented by Formula $\phi_3$. The naphthopyran by Formula $\phi_3$ is then reacted with the L substituted phenylamine of Formula $\phi_4$ to produce the L substituted phenylamine attached to the naphthopyran represented by Formula $\phi_5$ according to various non-limiting embodiments disclosed herein. Non-limiting examples of suitable B and B' substituent groups are set forth above in detail.

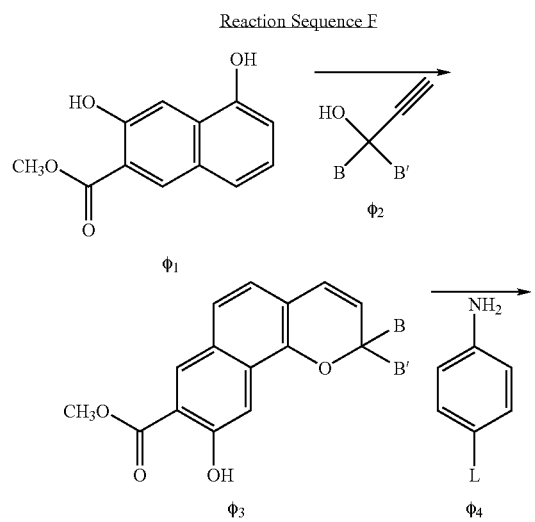

-continued

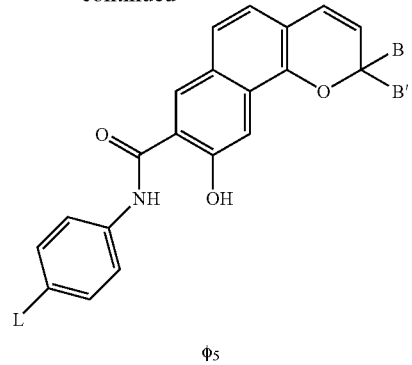

$\phi_5$

Although not limiting herein, in the hydroxy substituted A group represented by Formulae $\beta_1$ and $\epsilon_1$ (which are set forth in Reaction Sequences B and E, respectively), K can be a carbon that is di-substituted with methyl to form 2,3-dimethoxy-7,7-dimethyl-7H-benzo[c]fluoren-5-ol. Those skilled in the art will recognize numerous methods of making such a hydroxy substituted A group. For example, and without limitation, one method of forming 2,3-dimethoxy-7,7-dimethyl-7H-benzo[c]fluoren-5-ol is set forth in step 2 of Example 9 of U.S. Pat. No. 6,296,785, which is hereby specifically incorporated by reference. More specifically, as set forth in step 2 of Example 9 of U.S. Pat. No. 6,296,785, one non-limiting method of forming 2,3-dimethoxy-7,7-dimethyl-7H-benzo[c]fluoren-5-ol is as follows:

Step 1: 1,2-Dimethoxybenzene (92.5 grams) and a solution of benzoyl chloride (84.3 grams) in 500 milliliters (mL) of methylene chloride are added to a reaction flask fitted with a solid addition funnel under a nitrogen atmosphere. Solid anhydrous aluminum chloride (89.7 grams) is added to the reaction mixture with occasional cooling of the reaction mixture in an ice/water bath. The reaction mixture is stirred at room temperature for 3 hours. The resulting mixture is poured into 300 mL of a 1:1 mixture of ice and 1N hydrochloric acid and stirred vigorously for 15 minutes. The mixture is extracted twice with 100 mL methylene chloride. The organic layers are combined and washed with 50 mL of 10 weight percent sodium hydroxide followed by 50 mL of water. The methylene chloride solvent is removed by rotary evaporation to give a yellow solid. Recrystallization from 95 percent ethanol yields 147 grams of beige needles having a melting point of 103-105° C. The product is believed to have a structure consistent with 3,4,-dimethoxybenzophenone.

Step 2: Potassium t-butoxide (62 grams) and 90 grams of the product from preceding Step 1, is added to a reaction flask containing 300 mL of toluene under a nitrogen atmosphere. The mixture is heated to reflux and dimethyl succinate (144.8 grams) is added dropwise over 1 hour. The mixture is refluxed for 5 hours and cooled to room temperature. 300 mL of water is added to the reaction mixture and vigorously stirred for 20 minutes. The aqueous and organic phases separate and the organic phase is extracted with 100 mL portions of water three times. The combined aqueous layers are washed with 50 mL portions of chloroform three times. The aqueous layer is acidified to pH 2 with 6N hydrochloric acid and a precipitate forms and is removed by filtration.

The aqueous layer is extracted with three 100 mL portions of chloroform. The organic extracts are combined and concentrated by rotary evaporation. The resulting oil is believed to have a structure consistent with a mixture of (E and Z) 4-(3,4-dimethoxyphenyl)-4-phenyl-3-methoxycarbonyl-3-butenoic acids.

Step 3: The product from preceding Step 2 (8.6 grams), 5 mL of acetic anhydride, and 50 mL of toluene are added to a reaction flask under a nitrogen atmosphere. The reaction mixture is heated to 110° C. for 6 hours and cooled to room temperature, and the solvents (toluene and acetic anhydride) are removed by rotary evaporation. The residue is dissolved in 300 mL of methylene chloride and 200 mL of water. Solid sodium carbonate is added to the biphasic mixture until bubbling ceases. The layers separate and the aqueous layer is extracted with two 50 mL portions of methylene chloride. The organic layers are combined and the solvent (methylene chloride) is removed by rotary evaporation to yield a thick red oil. The oil is dissolved in warm methanol and chilled at 0° C. for 2 hours. The resulting crystals are collected by vacuum filtration and washed with cold methanol to produce 5 grams of a product having a melting point of 176-177° C. The recovered solid product is believed to have structures consistent with a mixture of 1-(3,4-dimethoxyphenyl)-2-methoxycarbonyl-4-acetoxynaphthalene and 1-phenyl-2-methoxycarbonyl-4-acetoxy-6,7-dimethoxynaphthalene.

Step 4: Five (5) grams of the product mixture from preceding Step 3, 5 mL of 12M hydrochloric acid, and 30 mL of methanol are combined in a reaction flask and heated to reflux for 1 hour. The reaction mixture is cooled and the resulting precipitate is collected by vacuum filtration and washed with cold methanol. The product is purified by filtering through a plug of silica gel using a 2:1 mixture of hexane and ethyl acetate as the elutant. Concentration of the filtrate by rotary evaporation yields 3 grams of a beige solid that is believed to have a structure consistent with 1-phenyl-2-methoxycarbonyl-6,7-dimethoxynaphth-4-ol.

Step 5: A reaction flask is charged with 2.8 grams of the product of preceding Step 4 under a nitrogen atmosphere. Anhydrous tetrahydrofuran (40 mL) is added to the flask. The reaction mixture is cooled in a dry ice/acetone bath and 41 mL of a methyl magnesium chloride solution (1M in tetrahydrofuran) is added dropwise over 15 minutes. The resulting yellow reaction mixture is stirred at 0° C. for 2 hours and slowly warmed to room temperature. The reaction mixture is poured into 50 mL of an ice/water mixture. Ether (20 mL) is added, and the layers separate. The aqueous layer is extracted with two 20 mL portions of ether, and the organic portions are combined and washed with 30 mL of water. The organic layer is dried over anhydrous magnesium sulfate and concentrated by rotary evaporation. The resulting oil is transferred into a reaction vessel (fitted with a Dean-Stark trap) containing 50 mL of toluene to which two drops of dodecylbenzene sulfonic acid are added. The reaction mixture is heated to reflux for 2 hours and cooled. The toluene is removed via rotary evaporation to yield 2 grams of the desired compound.

Further, it will be appreciated by those skilled in the art that essentially the same procedure as described above can be followed to form 7,7-dimethyl-7H-benzo[c]fluoren-5-ol, except in Step 1, benzene can be used in place of 1,2-dimethoxybenzene to form benzophenone, which is used in place of the 3,4-dimethoxybenzophenone in the remainder of the reaction. One such procedure is set forth in Example 9 of U.S. Pat. No. 6,296,785 B1, which is hereby incorporated by reference.

Further, while not limiting herein, in the hydroxy substituted A group represented by Formulae $\beta_1$ and $\epsilon_1$ (which are set forth in Reaction Sequences B and E, respectively), K can be a carbon that is substituted with an ethyl group and a hydroxy group to form 7-ethyl-2,3-dimethoxy-7H-benzo[c]fluoren-5,7-diol. Those skilled in the art will recognize numerous methods of making such a hydroxy substituted A group. For example, and without limitation, one method of forming 7-ethyl-2,3-dimethoxy-7H-benzo[c]fluoren-5,7-diol as follows:

Step 1: 1-phenyl-2-methoxycarbonyl-6,7-dimethoxynaphth-4-ol (which can be produced as indicated in Steps 1-4 above) (20.0 grams) is added to a reaction flask containing 150 mL of a 10 weight percent aqueous sodium hydroxide solution and 15 mL of methanol. The mixture is refluxed for 3 hours and cooled. The aqueous layer is washed twice with methylene chloride, 50 mL each, and the combined organic layers were extracted with 100 mL of water. The aqueous layers are combined and acidified to pH 2 with an aqueous solution of 6N hydrochloric acid. The aqueous layer is extracted four times with 50 mL portions of methylene chloride. The methylene chloride layers are combined and concentrated by rotary evaporation. The resulting oil is crystallized from ethanol (95%) to yield 12.0 grams of a beige solid that is believed to have a structure consistent with 1-phenyl-4-hydroxy-6,7-dimethoxy-2-naphthoic acid.

Step 2: The product from the preceding Step 1 (6.0 grams), 100 mL of toluene and 20 milligrams of dodecylbenzene sulfonic acid are added to a reaction flask fitted with a Dean-Stark trap. The resulting mixture is heated to reflux for 5 hours. A deep red solid precipitate is formed. Two more portions of dodecylbenzene sulfonic acid (50 milligrams and 500 milligrams) are added to the refluxing mixture at 3 hour intervals. The mixture is cooled and the solid is collected by vacuum filtration. Any unreacted starting material is removed via digestion in boiling acetonitrile. The mixture is vacuum filtered to yield 4.45 grams of a product that is believed to have a structure consistent with 2,3-dimethoxy-5-hydroxy-7H-benzo[C]fluoren-7-one.

Step 3: The product from preceding Step 2 (3.0 grams) is added to a dry reaction flask under a nitrogen atmosphere. Anhydrous tetrahydrofuran (50 mL) is added and the reaction mixture is cooled in a dry ice/acetone bath. Ethyl magnesium chloride (7.2 mL of a 2M tetrahydrofuran solution) is added dropwise over one hour, and the reaction is slowly warmed to room temperature. The reaction mixture is poured into a flask containing 100 grams of ice, and this mixture is acidified to pH 3 with a 6N solution of hydrochloric acid. The layers are separated and the aqueous layer is extracted four times with 50 mL portions of diethyl ether. The organic layers are combined and the solvents (ether and tetrahydrofuran) are removed by rotary evaporation. The residue is chromatographed on silica gel using a 3:1 v/v mixture of hexane and ethyl acetate as the eluent. The fractions containing product are collected, concentrated by rotary evaporation and recrystallized from ethanol (95%) yielding 1.5 grams of the desired product.

As previously discussed, according to various non-limiting embodiments disclosed herein, the photochromic compounds can be non-thermally reversible photochromic compounds.

For example, one non-limiting embodiment provides a non-thermally reversible photochromic compound represented by one of Formula X and Formula XI:

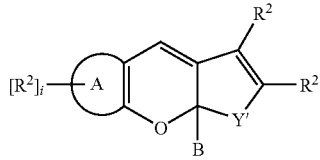

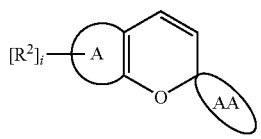

wherein:

(a) A is chosen from naphthol benzo, phenanthro, fluorantheno, antheno, quinolino, thieno, furo, indolo, indolino, indeno, benzofuro, benzothieno, thiopheno, indeno-fused naphthol heterocyclic-fused naphthol and heterocyclic-fused benzo;

(b) AA is a group represented by one of Formula xv and xvi:

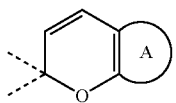

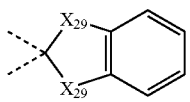

wherein $X_{29}$ is independently chosen from each occurrence form —C(R")(R")—, —O—, —S—, and —N(R''')—, wherein R" is independently chosen for each occurrence from hydrogen, a substituted or unsubstituted alkyl, cycloalkyl, arylalkyl, or together form cycloalkyl that is substituted or unsubstituted; R''' is independently chosen for each occurrence from an alkyl, aryl or arylalkyl group that is unsubstituted or substituted with at least one of:

(i) —CH(CN)$_2$ or —CH(COOX$_1$)$_2$ wherein $X_1$ is as set forth above;

(ii) —CH(X$_2$)(X$_3$), wherein $X_2$ and $X_3$ are as set forth above;

(iii) —C(O)X$_{24}$, wherein $X_{24}$ is as set forth above; and (iv) halogen, hydroxy, ester, or amine;

(c) Y' is chosen from: —(Y$_1$)C=C(Y$_2$)—, —O—, —S—, —S(O)(O)—, and —N(X$_7$)—, wherein Y$_1$ and Y$_2$ together form benzo, naphtho, phenanthro, furo, thieno, benzofuro, benzothieno, and indolo; and X$_7$ is as set forth above;

(d) B is as set forth above;

(e) i is an integer chosen from 0 to 4, and each R$^2$ is independently chosen for each occurrence from the R$^2$ groups set forth above;

wherein lengthening agent L is independently chosen for each occurrence from a compound represented by Formula I.

Additionally, according to various non-limiting embodiments disclosed herein, the photochromic compound represented either of Formula X or XI comprises at least one lengthening agent (L) represented by Formula I above. As previously discussed, in Formula I, c, d, e, and f each can be independently chosen from an integer ranging from 1 to 20, inclusive; and d', e' and f' each can be independently chosen from 0, 1, 2, 3, and 4, provided that the sum of d'+e'+f' is at least 1. According to other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f' is at least 2. According to still other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f' is at least 3. According to still other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f' is at least 1.

Thus, for example, in either of Formula X or XI, "i" can be at least 1 and at least one of the R$^2$ groups can be a lengthening agent L. Additionally or alternatively, the photochromic compound can comprise at least one R$^2$ group that is substituted with a lengthening agent L. Moreover, although not limiting herein, according to various non-limiting embodiments disclosed herein, the lengthening agent (L) can be attached to a photochromic group at any available position such that L extends or lengthens the photochromic group in an activated state such that the absorption ratio of the extended photochromic group (i.e., the photochromic compound) is enhanced as compared to the unextended photochromic group. Thus, for example and without limitation, according to various non-limiting embodiments wherein the photochromic compound is represented by Formula X, L can be directly bonded to the pyran group, for example, wherein i is at least 1 and R$^2$ is L, or it can be indirectly bonded to the pyran group, for example, as a substituent on an R$^2$ or B group such that L extends the pyran group in an activated state such that the absorption ratio of the photochromic compound is enhanced as compared to the unextended pyran group. Further, for example and without limitation, according to various non-limiting embodiments wherein the photochromic compound is represented by Formula XI, L can be directly bonded to the pyran group, for example, wherein i is at least 1 and R$^2$ is L, or it can be indirectly bonded to the pyran group, for example, as a substituent on an R$^2$ or the AA group such that L extends the pyran group in an activated state such that the absorption ratio of the photochromic compound is enhanced as compared to the unextended pyran group.

For example, although not limiting herein, a general reaction sequence for forming a non-thermally reversible photochromic compound represented by Formula X above (wherein A is benzo) is as follows:

Reaction Sequence W

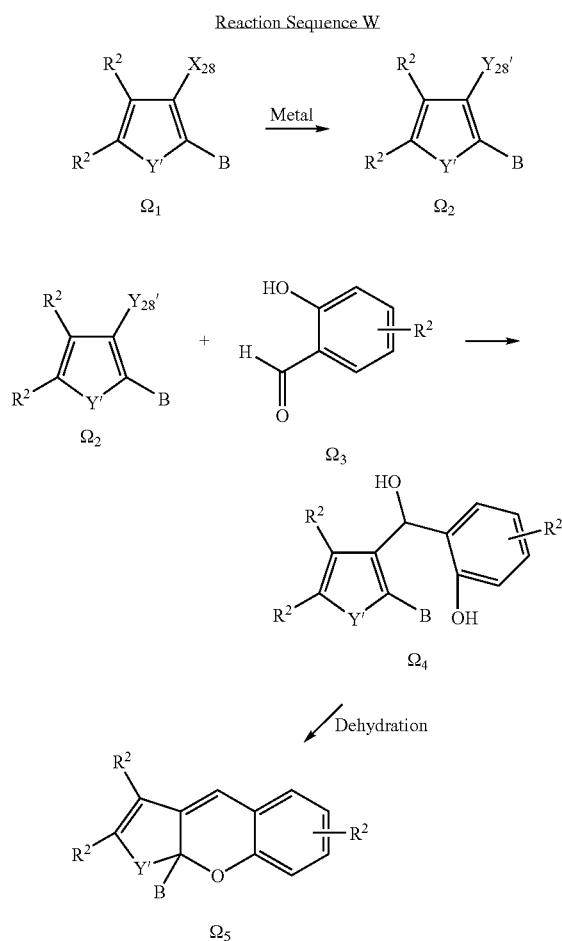

In Part 1 of Reaction Sequence W, $X_{28}$ is a halogen such as Br, I, and Cl; and the metal is chosen from Li, Mg, Zn, and Sn; and $X_{28}'$ is a metal salt, such as: $LiX_{28}$, $MgX_{28}$, $ZnX_{28}$, and $SnX_{28}$. Further, in Part A of Reaction Sequence W, the B and halogen substituted compound represented by Formula $\Omega_1$ is reacted with a metal in a halogen metal exchange reaction in an ether-like solvent such as, but not limited to, tetrahydrofuran to produce the metallated compound represented by Formula $\Omega_2$.

In Part 2 of Reaction Sequence W, the metallated compound represented by Formula $\Omega_2$ is reacted with an $R^2$ substituted salicylaldehyde derivative (represented by Formula $\Omega_3$) in an ether-like solvent (such as but not limited to tetrahydrofuran) to produce the diol compound represented by Formula $\Omega_4$. Thereafter, the diol compound represented by Formula $\Omega_4$ is dehydrated with dehydration agents, such as but not limited to, magnesium sulfate, sodium sulfate, $P_2O_5$, molecular sieves, p-toluene sulfonic acids to produce the non-thermally reversible photochromic compound according to one non-limiting embodiment disclosed herein and represented by Formula $\Omega_5$. Further, as discussed above with respect to Formula X, at least one $R^2$ group in the photochromic compound represented by Formula $\Omega_5$, can be a lengthening agent L, or at least one $R^2$ group, B or Y' can comprise a group that is substituted with a lengthening agent L.

For example, although not limiting herein, a general reaction sequence for forming a non-thermally reversible photochromic compound represented by Formula XI above is as follows:

Reaction Sequence X

Part 1

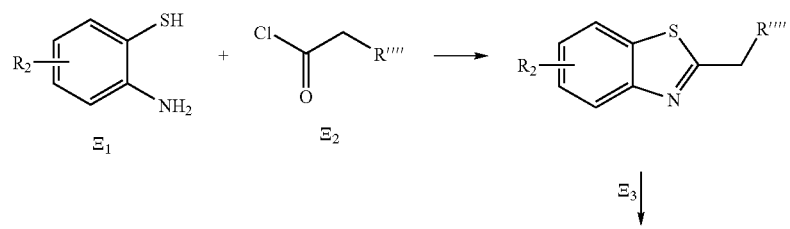

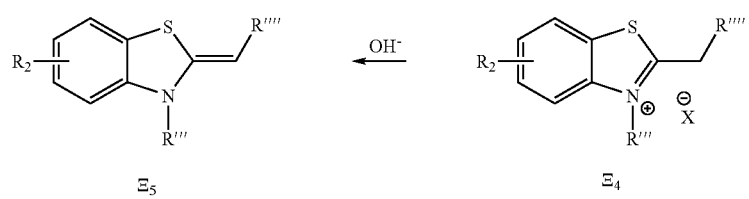

Part 2

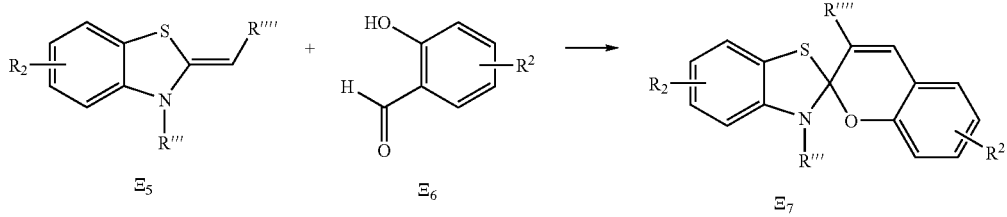

In Part 1 of Reaction Sequence X, an orthoaminothiophenol represented by Formula $\Xi_1$ is condensed with an acid chloride represented by Formula $\Xi_2$, wherein R"" is chosen from hydrogen, a substituted or unsubstituted alkyl, cycloalkyl, and arylalkyl, in a solvent such as, but not limited to, chloroform to form the benzothiazole derivative represented by Formula $\Xi_3$. The benzothiazole derivative represented by Formula $\Xi_3$ is reacted with an alkyl halide, tosylate, or methylsulfonate, with or without solvents, to form the benzothiazolium quaternary salt represented by Formula $\Xi_4$. The benzothiazolium quaternary salt represented by Formula $\Xi_4$ is then reacted with a base, such as amine or hydroxide (which is shown) to give the benzothiozoline derivative represented by Formula $\Xi_5$.

In Part 2 of Reaction Sequence X, the benzothiozoline derivative represented by Formula $\Xi_5$ is condensed with an $R^2$ substituted salicylaldehyde derivative (represented by Formula $\Xi_6$) to produce the non-thermally reversible photochromic compound according to one non-limiting embodiment disclosed herein and represented by Formula $\Xi_7$. As previously discussed with respect to Formula XI above, in the photochromic compound represented by Formula $\Xi_7$, at least one $R^2$ group can be a lengthening agent L (represented by Formula I above) or can be a group substituted with a lengthening agent L.

Another non-limiting embodiment provides a photochromic compound represented by Formula XII:

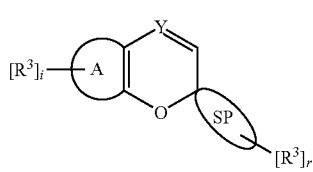

XII wherein:

(a) A is chosen from naphthol benzo, phenanthro, fluorantheno, antheno, quinolino, thieno, furo, indolo, indolino, indeno, benzofuro, benzothieno, thiopheno, indeno-fused naphthol heterocyclic-fused naphthol and heterocyclic-fused benzo;

(b) Y is C or N;

(c) SP is a spiro-group chosen from indolino and benzindoline; and (d) i is an integer chosen from 0 to the total number of available positions on A, r is an integer chosen from 0 to the total number available positions on SP, provided that the sum of i+r is at least one, and each $R^3$ is independently chosen for each occurrence from:

(i) a lengthening agent L represented by Formula I above;

(ii) hydrogen, $C_1$-$C_{12}$ alkyl, $C_2$-$C_{12}$ alkylidene, $C_2$-$C_{12}$ alkylidyne, vinyl, $C_3$-$C_7$ cycloalkyl, $C_1$-$C_{12}$ haloalkyl, allyl, halogen, and benzyl that is unsubstituted or mono-substituted with at least one of $C_1$-$C_{12}$ alkyl and $C_1$-$C_{12}$ alkoxy;

(iii) phenyl that is mono-substituted at the para position with at least one substituent chosen from: $C_1$-$C_7$ alkoxy, linear or branched chain $C_1$-$C_{20}$ alkylene, linear or branched chain $C_1$-$C_4$ polyoxyalkylene, cyclic $C_3$-$C_{20}$ alkylene, phenylene, naphthylene, $C_1$-$C_4$ alkyl substituted phenylene, mono- or poly-urethane($C_1$-$C_{20}$)alkylene, mono- or poly-ester($C_1$-$C_{20}$)alkylene, mono- or poly-carbonate($C_1$-$C_{20}$)alkylene, polysilanylene, polysiloxanylene and mixtures thereof, wherein the at least one substituent is connected to an aryl group of a photochromic material;

(iv) —$CH(CN)_2$ and —$CH(COOX_1)_2$, wherein $X_1$ is as set forth above;

(v) —$CH(X_2)(X_3)$, wherein $X_2$ and $X_3$ are as set forth above;

(vi) an unsubstituted, mono-, di-, or tri-substituted aryl group, such as phenyl, naphthyl, phenanthryl, or pyrenyl; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl; wherein each substituent is independently chosen for each occurrence from:

(A) a lengthening agent L represented by Formula I above; and (B) —$C(O)X_6$, wherein $X_6$ is as set forth above;

(C) aryl, haloaryl, $C_3$-$C_7$ cycloalkylaryl, and an aryl group that is mono- or di-substituted with $C_1$-$C_{12}$ alkyl or $C_1$-$C_{12}$ alkoxy;

(D) $C_1$-$C_{12}$ alkyl, $C_3$-$C_7$ cycloalkyl, $C_3$-$C_7$ cycloalkyloxy ($C_1$-$C_{12}$)alkyl, aryl($C_1$-$C_{12}$)alkyl, aryloxy($C_1$-$C_{12}$)alkyl, mono- or di-($C_1$-$C_{12}$)alkylaryl($C_1$-$C_{12}$)alkyl, mono- or di-($C_1$-$C_{12}$)alkoxyaryl($C_1$-$C_{12}$)alkyl, haloalkyl, and mono($C_1$-$C_{12}$)alkoxy($C_1$-$C_{12}$)alkyl;

(E) $C_1$-$C_{12}$ alkoxy, $C_3$-$C_7$ cycloalkoxy, cycloalkyloxy($C_1$-$C_{12}$)alkoxy, aryl($C_1$-$C_{12}$)alkoxy, aryloxy($C_1$-$C_{12}$)alkoxy, mono- or di-($C_1$-$C_{12}$)alkylaryl($C_1$-$C_{12}$)alkoxy, and mono- or di-($C_1$-$C_{12}$)alkoxyaryl($C_1$-$C_{12}$)alkoxy;

(F) amido, amino, mono- or di-alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidyl, hydroxy, acryloxy, methacryloxy, and halogen;
(G) —OX$_7$ and —N(X$_7$)$_2$, wherein X$_7$ is as set forth above;
(H) —SX$_{11}$, wherein X$_{11}$ is as set forth above;
(I) a nitrogen containing ring represented by Formula i, which is set forth above; and
(J) a group represented by one of Formula ii or iii, which are set forth above;
(vi) an unsubstituted or mono-substituted group chosen from pyrazolyl, imidazolyl, pyrazolinyl, imidazolinyl, pyrrodlinyl, phenothiazinyl, phenoxazinyl, phenazinyl, or acridinyl, wherein each substituent is independently chosen from a lengthening agent L, C$_1$-C$_{12}$ alkyl, C$_1$-C$_{12}$ alkoxy, phenyl, hydroxy, amino or halogen;
(viii) a group represented by one of Formula iv or v, which are set forth above;
(ix) a group represented by Formula vi, which is set forth above;
(x) —C(O)X$_{24}$, wherein X$_{24}$ is as set forth above;
(xi) —OX$_7$ and —N(X$_7$)$_2$, wherein X$_7$ is as set forth above;
(xii) —SX$_{11}$, wherein X$_{11}$ is as set forth above;
(xiii) a nitrogen containing ring represented by Formula i, which is set forth above;
(xiv) a group represented by one of Formula ii or iii, which are set forth above; and
(xv) immediately adjacent R$^3$ groups together form at a group represented by one of Formula vii, viii, or ix, which are set forth above.

Additionally, according to various non-limiting embodiments disclosed herein, the photochromic compound represented by Formula XII comprises at least one lengthening agent (L) represented by Formula I above. As previously discussed, in Formula I, c, d, e, and f each can be independently chosen from an integer ranging from 1 to 20, inclusive; and d', e' and f' each can be independently chosen from 0, 1, 2, 3, and 4, provided that the sum of d'+e'+f' is at least 1. According to other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f' is at least 2. According to still other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f' is at least 3. According to still other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f' is at least 1.

As discussed above with respect to the photochromic compounds generally represented by Formula II disclosed herein, the photochromic compounds generally represented by Formula XII can be extended at any available position by substitution with L or an R$^3$ group substituted with L, and/or in any desired direction by numerous combinations of substitutions of available positions with L or R$^3$ groups substituted with L. Thus, for example, although not limiting herein, the photochromic compounds generally represented by Formula XII can be extended by substituting the SP group with L or an R$^3$ group substituted with L, and/or by substituting the A group with L or an R$^3$ group substituted with L so as to provided a desired average absorption ratio of the photochromic compound.

As discussed above with reference to Formula XII, according to various non-limiting embodiments disclosed herein, the SP group can be indolino. More specifically, according to various non-limiting embodiments disclosed herein, the photochromic compound can be represented by Formula XIII:

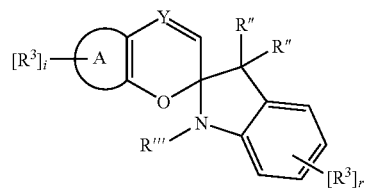

XIII wherein each R" is independently chosen for each occurrence from hydrogen, a substituted or unsubstituted alkyl, cycloalkyl, arylalkyl, or together form cycloalkyl that is substituted or unsubstituted; R'" is chosen from an alkyl, aryl, or arylalkyl group that is unsubstituted or substituted with at least one of: (i) —CH(CN)$_2$ or —CH(COOX$_1$)$_2$; (ii) —CH(X$_2$)(X$_3$); and (iii) —C(O)X$_{24}$ (wherein X$_1$, X$_2$, X$_3$, and X$_{24}$ are as set forth above); and (iv) halogen, hydroxy, ester, or amine; and wherein at least one of i and r is at least 1, and at least one R$^3$ comprises L.

For example, although not limiting herein, according to certain non-limiting embodiments disclosed herein wherein the SP group is indolino, the photochromic compound can be represented by at least one of Formula XIV and Formula XV:

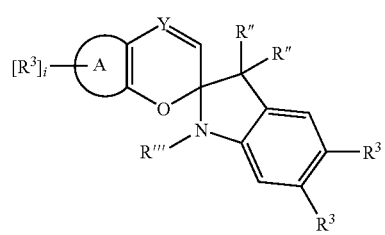

XIV

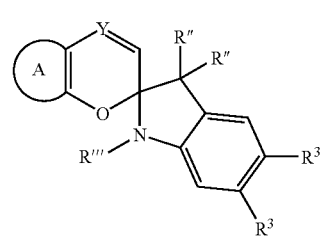

XV wherein, for each formula, at least one R$^3$ comprises L. Further, according to one non-limiting embodiment, at least one R$^3$ is L. As discussed above with respect to Formula XII, Y in Formulae XIV and XV can be chosen from C or N. For example, according to various non-limiting embodiments, Y can be C, and the photochromic compound can be a spiro(indolino)pyran. According to other non-limiting embodiments, Y can be N, and the photochromic compound can be a spiro(indolino)oxazine.

Referring again to Formula XII above, according to various non-limiting embodiments, A can be naphtho, Y can be N, and the photochromic compound can be a spiro-naphthoxazine represented by one of Formula XVI or Formula XVII:

XVI

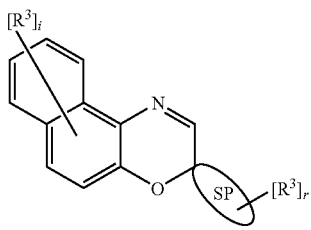

XVII

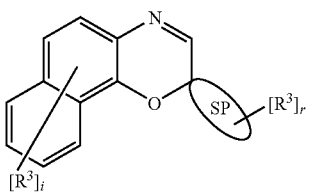

wherein, for each formula, at least one $R^3$ comprises a lengthening agent L. Thus, the spiro-naphthoxazine according to these non-limiting embodiments disclosed can be extended by substituting the I group with a lengthening agent L or an $R^3$ group substituted with a lengthening agent L, and/or by substituting the one or more of the available positions on the naphtho group with a lengthening agent L or an $R^3$ group substituted with L so as to provide a desired average absorption ratio.

For example, although not limiting herein, according to various non-limiting embodiments, the photochromic compound can be represented by Formula XVIII:

XVIII

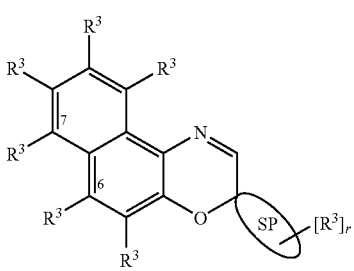

wherein at least one of: the $R^3$ in the 6-position or the $R^3$ in the 7-position comprises a lengthening agent L. Further, according to one specific non-limiting embodiment, at least one of the $R^3$ group in the 6-position or the $R^3$ group 7-position of Formula XVIII is a lengthening agent L.

According other non-limiting embodiments, the photochromic compound can be represented by Formula XIX:

XIX

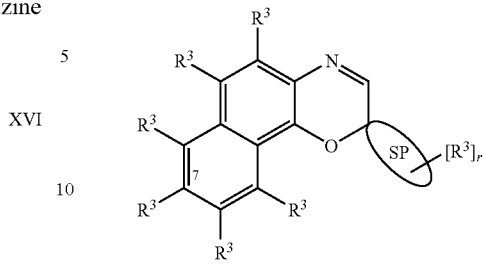

wherein at least the $R^3$ in the 7-position comprises a lengthening agent L. Further, according to one specific non-limiting embodiment, the $R^3$ group in the 7-position is a lengthening agent L.

Referring again to Formula XII above, according to other non-limiting embodiments disclosed herein, A can be benzo, Y can be N, and the photochromic compound can be represented by Formula XX:

XX

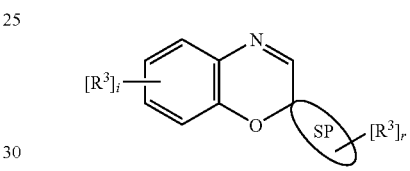

wherein at least one $R^3$ comprises a lengthening agent L. More specifically, according to one non-limiting embodiment the photochromic compound can comprise Formula XXI:

XXI

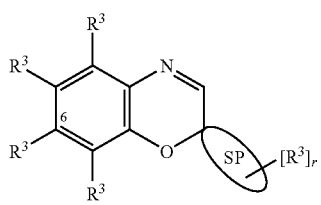

wherein at least the $R^3$ group in the 6-position comprises a lengthening agent L. Further, according to various non-limiting embodiments, the $R^3$ group in the 6-position is a lengthening agent L.

Further, the photochromic compound according to various non-limiting embodiments disclosed herein and generally represented by Formula XII can have an average absorption ratio greater than 2.3 in an activated state as determined according to CELL METHOD. According to other non-limiting embodiments, the photochromic compound disclosed herein and generally represented by Formula XII can have an average absorption ratio ranging from 4 to 20, from 3 to 30, or from 2.5 to 50 in an activated state as determined according to CELL METHOD.

A general reaction sequence for synthesizing photochromic compounds according to various non-limiting embodiments disclosed herein and generally represented by Formula XII, and more specifically represented by Formula XIII, wherein Y is N and SP is indolino is depicted below in Reaction Sequence G.

Reaction Sequence G

Part 1: General Nitrosation Process

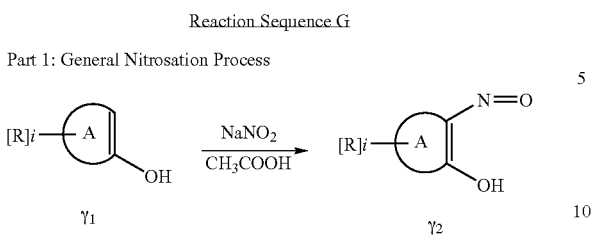

Reaction Sequence G, Part 1 depicts a general nitrosation process in which the hydroxylated A group represented by of Formula $\gamma_1$ is reacted with sodium nitrite in the presence of an acid, such as but not limited to acetic acid, to produce the nitroso-substituted A group represented by Formula $\gamma_2$. Suitable non-limiting examples of A groups include naphthol benzo, phenanthro, fluorantheno, antheno, quinolino, indeno-fused naphthol heterocyclic-fused naphthol and heterocyclic-fused benzo. Optionally, the A group can be substituted with one or more $R^3$ groups, each of which may comprise a lengthening agent L that is the same or different from the remaining Ls. Non-limiting examples of $R^3$ substituent groups that are suitable for use in conjunction with various non-limiting embodiments disclosed herein are set forth above in detail with respect to Formula XII.

Part 2: General Coupling Reaction

In Part 2 of Reaction Sequence G, the nitroso-substituted A group represented by Formula $\gamma_2$ is coupled with a Fischer's base represented by Formula $\gamma_3$. The coupling is conducted in a solvent, such as but not limited to absolute ethanol, and heated under reflux conditions to produce the photochromic oxazine represented by Formula $\gamma_4$ according to various non-limiting embodiments disclosed herein.

As discussed above with respect to Formula XVIII, in Formula $\gamma_3$ each R" is independently chosen for each occurrence from hydrogen, a substituted or unsubstituted alkyl, cycloalkyl, arylalkyl, or together form cycloalkyl that is substituted or unsubstituted; R'" is chosen from an alkyl, aryl, or arylalkyl group that is unsubstituted or substituted with at least one of: (i) —CH(CN)$_2$ or —CH(COOX$_1$)$_2$; (ii) —CH(X$_2$)(X$_3$); and (iii) —C(O)X$_{24}$ (wherein X$_1$, X$_2$, X$_3$, and X$_{24}$ are as set forth above); and (iv) halogen, hydroxy, ester, or amine. Possible $R^3$ substituents are discussed above in detail with respect to Formula XII.

The general nitrosation process shown in Part 1 of Reaction Sequence G is more specifically set forth in the following two sequences (Reaction Sequences H and I), which generally depict two nitroso phenol synthesis processes for producing nitroso-substituted A groups, which can optionally be substituted with at least one $R^3$, that can be used in coupling reactions to produce the oxazine products of the present invention. As illustrated in Path (2) of Sequences H and I, prior to reacting with NaNO$_2$, the intermediate compound can be further reacted with one or more other reactants to form a suitable lengthening agent L on the A group.

Reaction Sequence H

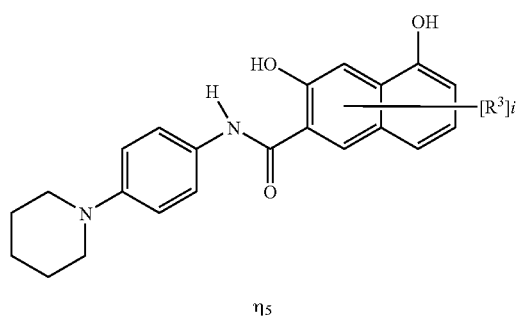

η₅

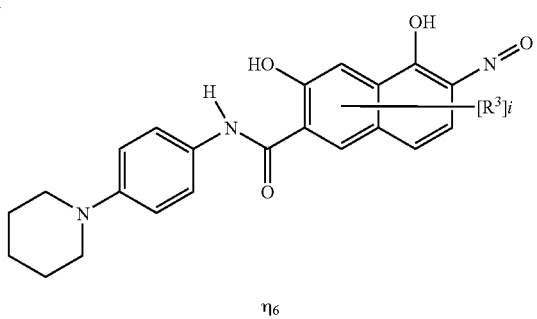

η₆

More specifically, in Reaction Sequence H, the carboxylic acid of the hydroxylated A group represented by Formula η₁ is converted into ester of hydroxylated A group represented by Formula η₂. Ester of the hydroxylated A group represented by Formula η₂ can then be reacted with sodium nitrite in the presence of an acid, such as but not limited to acetic acid, to produce the nitroso-substituted A group of Formula η₃. Alternatively, as shown in Path (2), ester of hydroxylated A group represented by Formula η₂ can be reacted with 4-piperidinoaniline (represented by Formula η₄) under basic conditions to produce the L substituted compound represented by Formula η₅. The L substituted compound represented by Formula η₅ is then subjected to the nitrosation reaction to produce the L and nitroso substituted A group represented Formula η₆. Further, the L and nitroso substituted A group optionally can be substituted with one or more R³ groups, each of which can comprise a lengthening agent L which is the same or different from the remaining Ls.

As discussed above with respect to Reaction Sequence H, in Reaction Sequence I (below) the carboxylic acid of the hydroxylated A group represented by Formula ι₁, is converted into ester of hydroxylated the A group represented by Formula ι₂. Ester of the hydroxylated A group represented by Formula ι₂ can then be reacted with sodium nitrite in the presence of an acid, such as but not limited to acetic acid, to produce the nitroso-substituted A group of Formula ι₃. Alternatively, as shown in Path (2), ester of the hydroxylated the A group represented by Formula ι2 can be reacted with 4-phenyl aniline (represented by Formula ι₄) under basic conditions to produce the L substituted 4-phenyl aniline represented by Formula ι₅. The L substituted 4-phenyl aniline represented by Formula ι₅ is then subjected to the nitrosation reaction to produce the L and nitroso substituted A group represented Formula ι₆. As discussed above, the (L substituted (nitroso substituted A groups)), optionally can be substituted with one or more R³ groups, each of which can comprise a lengthening agent L which is the same or different from the remaining Ls.

Reaction Sequence I

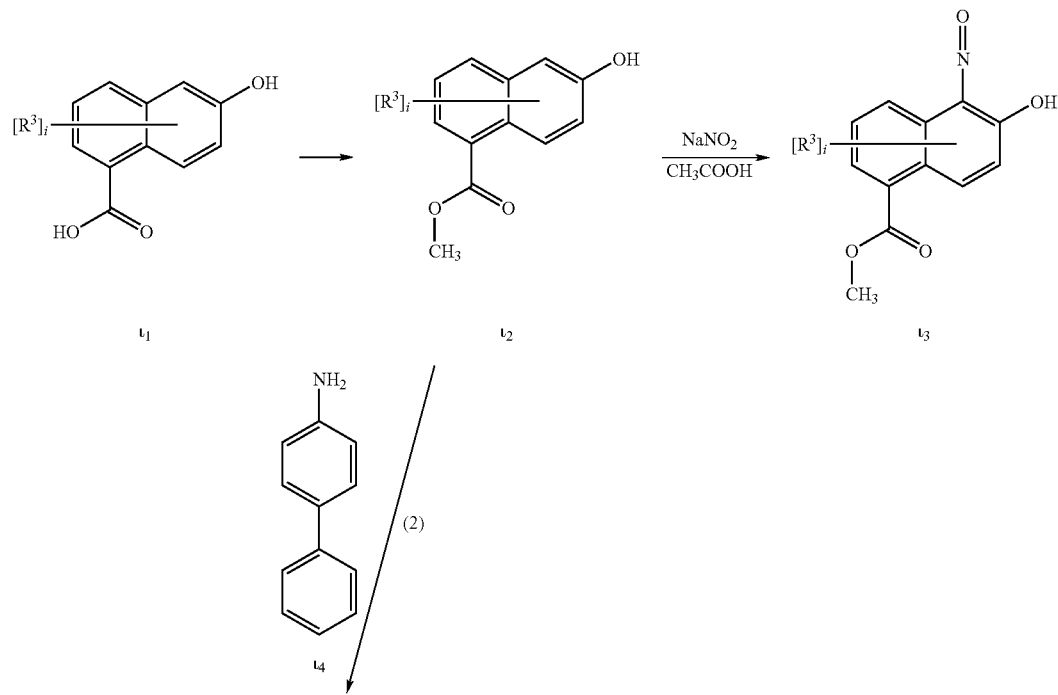

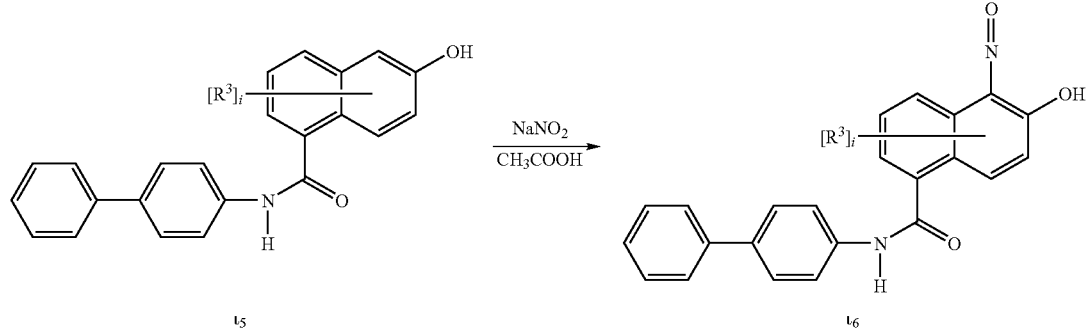

More specific reaction sequences for synthesizing the photochromic compounds according to various non-limiting embodiments disclosed herein and generally represented by Formula XII above, and more specifically represented by Formula XIII above, wherein Y is N and SP is indolino are depicted below in Reaction Sequences J and K.

In Reaction Sequence J (below), a nitrosophenol represented by Formula $\Phi_1$ is reacted in methanol with a lengthening agent L, which is piperazino phenol (represented by Formula $\Phi_2$), to form the L substituted nitrosonaphthol represented by Formula $\Phi_3$. As depicted in Reaction Sequence J, the L substituted nitrosonaphthol can be further substituted with one or more R groups, each of which may comprise a lengthening agent L that is the same or different from the remaining L substituents. The L substituted nitrosonaphthol represented by Formula $\Phi_3$ is then coupled by heating with the Fischer's base represented by Formula $\Phi_4$ to produce the L substituted naphthoxazine represented by Formula $\Phi_5$.

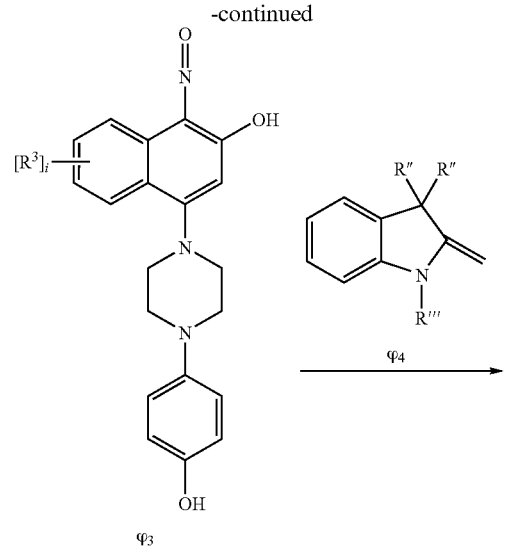

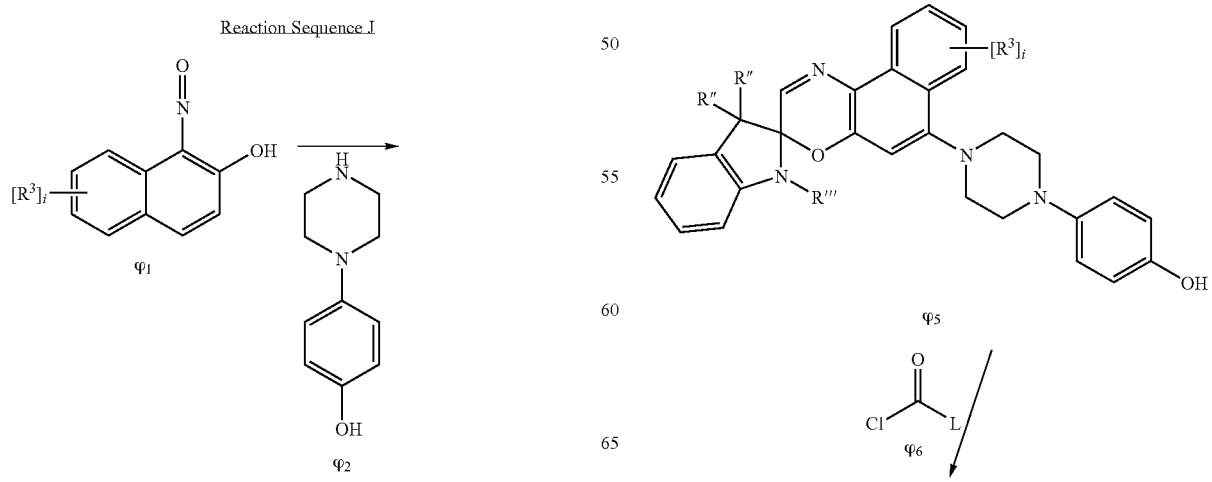

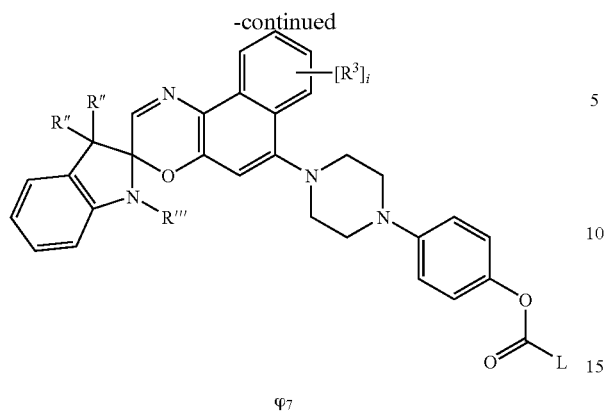

φ7

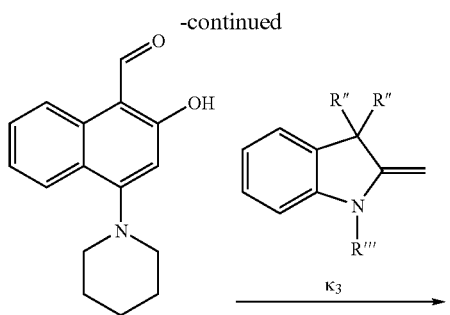

κ2

With continued reference to Reaction Sequence J, the L substituted naphthoxazine represented by Formula $\Phi_5$ can be further extended by reacting the L substituted naphthoxazine with another L substituted compound represented by Formula $\Phi_6$ to produce a naphthoxazine represented by Formula $\Phi_7$ according to various non-limiting embodiments disclosed herein. Further, as previously discussed and as depicted in Reaction Sequence J, naphthoxazine represented by Formula $\Phi_7$ optionally can be substituted with one or more $R^3$ groups, each of which may comprise a lengthening agent L that is the same or different from the remaining Ls.

As illustrated above in Reaction Sequence J, generally after coupling the nitrosophenol with the Fischer's base, the resultant naphthoxazine can be further reacted with one or more other reactants to extend the naphthoxazine with lengthening agent L. However, those skilled in the art will appreciate that, additionally or alternatively, prior to coupling the nitrosophenol with the Fischer's base, the nitrosophenol can be reacted to substitute the nitrosophenol with one or more lengthening agents L (for example as shown above in Reaction Sequences H and I). Further, such L substituted nitrosophenols can be coupled with a Fischer's base to form an L-substituted naphthoxazine as generally depicted in Reaction Sequence K, below.

Reaction Sequence K

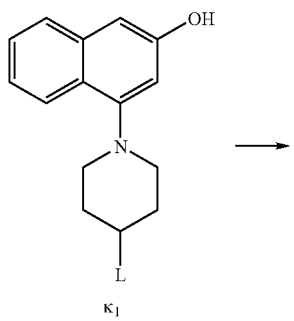

κ1

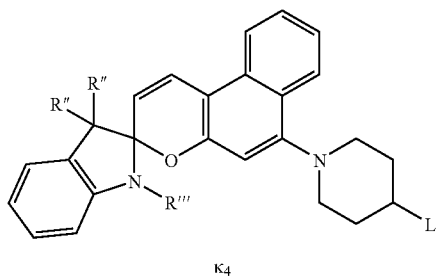

κ4

More specifically, in Reaction Sequence K, an L substituted piperidinylnaphthol represented by Formula $\kappa_1$ is reacted with trialkoxymethane and heated to form the L and formyl substituted naphthol represented by Formula $\kappa_2$. The compound represented by Formula $\kappa_2$ is then reacted with the Fischer's base (represented by Formula $\kappa_3$) to produce the L substituted spironaphthopyran represented by Formula $\kappa_4$ according to various non-limiting embodiments disclosed herein.

As previously discussed, generally after coupling the nitrosophenol with the Fischer's base (for example as shown in Reaction Sequence J), the resultant naphthoxazine can be further reacted with one or more other reactants to extend the naphthoxazine with lengthening agent L. Several non-limiting examples of such extension are provided in the generalized Reaction Sequence M below.

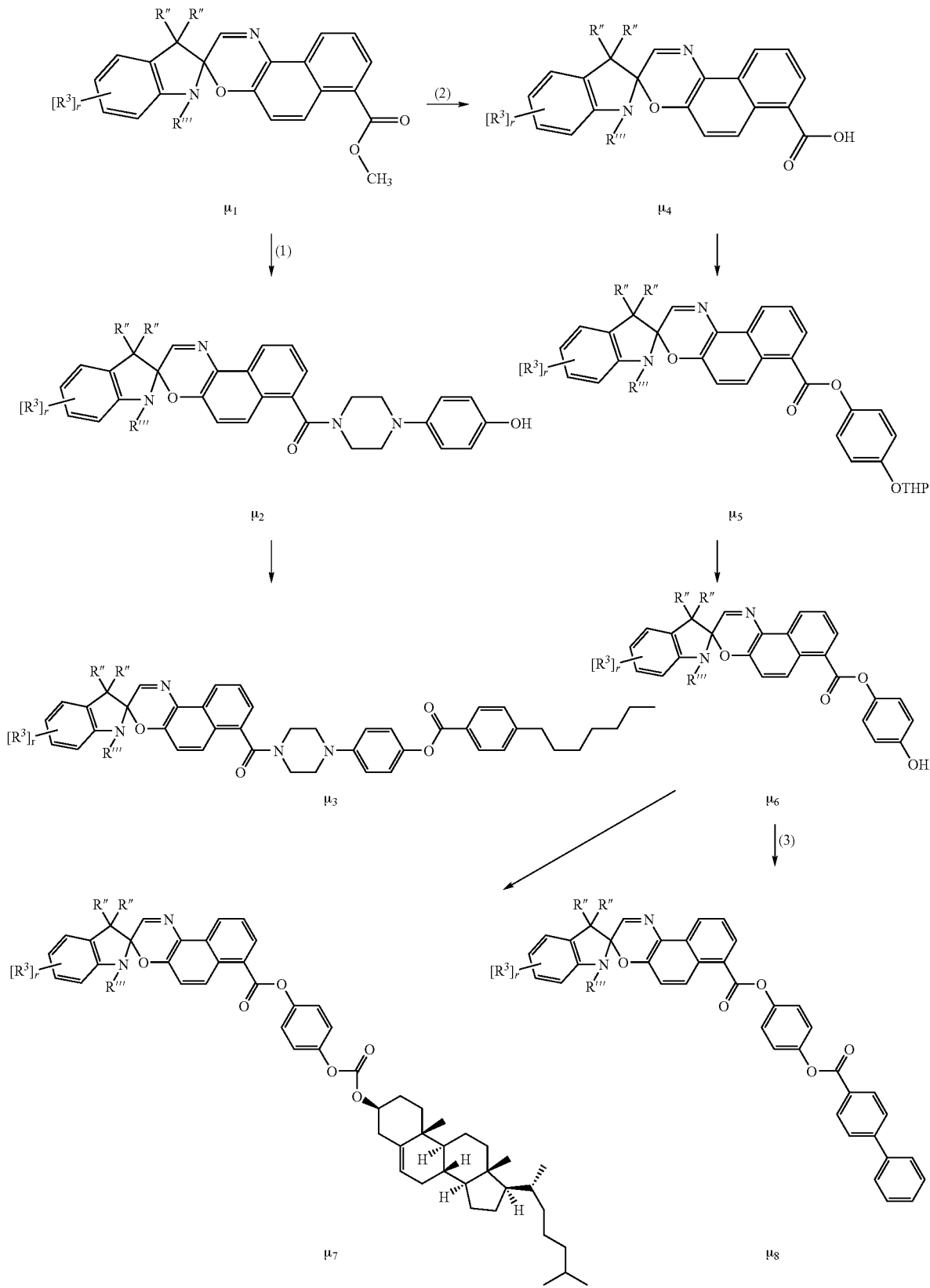
Reaction Sequence M

More specifically, Reaction Sequence M depicts three paths for adding a lengthening agent L to a naphthoxazine to produce the photochromic oxazines according to various non-limiting embodiments disclosed herein. In the first path (1), the naphthoxazine represented by Formula $\mu_1$ is reacted with hydroxyphenylpiperazine to produce the material represented by Formula $\mu_2$. The material represented by Formula $\mu_2$ is benzoylated with hexylbenzoyl chloride to produce the material represented by Formula $\mu_3$.

In the second path (2), the material represented by Formula $\mu_1$ undergoes hydrolysis and is converted into the material of Formula $\mu_4$. In an esterification reaction with a phenol-like material in the presence of dicyclohexylcarbodiimide in methylene chloride the material represented by Formula $\mu_4$ is converted into the material represented by Formula $\mu_5$ having the tetrahydropyran protecting group. The material represented by Formula $\mu_5$ is deprotected by a dilute solution of hydrochloric acid in an alcoholic solvent, such as but not limited to ethanol, to form the material represented by Formula $\mu_6$. The material represented by Formula $\mu_6$ is reacted with a cholesterol chloroformate to form the material represented by Formula $\mu_7$.

In the third path (3), the material represented by Formula $\mu_6$ is benzoylated with 4-phenylbenzoyl chloride to form the material represented by Formula $\mu_8$.

Another non-limiting embodiment provides a photochromic compound represented by Formula XXII:

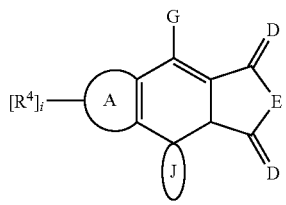

XXII wherein
(a) A is chosen from naphthol benzo, phenanthro, fluorantheno, antheno, quinolino, thieno, furo, indolo, indolino, indeno, benzofuro, benzothieno, thiopheno, indeno-fused naphthol heterocyclic-fused naphthol and heterocyclic-fused benzo;
(b) J is a spiro-alicyclic ring;
(c) each D is independently chosen from O, N(Z), C(X$_4$), C(CN)$_2$ wherein Z is independently chosen for each occurrence from hydrogen, $C_1$-$C_6$ alkyl, cycloalkyl and aryl;
(d) G is group chosen from alkyl, cycloalkyl, and aryl, which can be unsubstituted or substituted with at least one substituent $R^4$;
(e) E is —O— or is —N($R^5$)—, wherein $R^5$ is chosen from:
  (i) hydrogen, $C_1$-$C_{12}$ alkyl, $C_2$-$C_{12}$ alkene, $C_2$-$C_{12}$ alkyne, vinyl, $C_3$-$C_7$ cycloalkyl, $C_1$-$C_{12}$ haloalkyl, allyl, halogen, and benzyl that is unsubstituted or mono-substituted with at least one of $C_1$-$C_{12}$ alkyl and $C_1$-$C_{12}$ alkoxy;
  (ii) phenyl that is mono-substituted at the para position with at least one substituent chosen from: $C_1$-$C_7$ alkoxy, linear or branched chain $C_1$-$C_{20}$ alkylene, linear or branched chain $C_1$-$C_4$ polyoxyalkylene, cyclic $C_3$-$C_{20}$ alkylene, phenylene, naphthylene, $C_1$-$C_4$ alkyl substituted phenylene, mono- or poly-urethane($C_1$-$C_{20}$)alkylene, mono- or poly-ester($C_1$-$C_{20}$)alkylene, mono- or poly-carbonate($C_1$-$C_{20}$)alkylene, polysilanylene, polysiloxanylene and mixtures thereof, wherein the at least one substituent is connected to an aryl group of a photochromic material;
  (iii) —CH(CN)$_2$ and —CH(COOX$_1$)$_2$, wherein X$_1$ is as set forth above;
  (iv) —CH(X$_2$)(X$_3$), wherein X$_2$ and X$_3$ are as set forth above;
  (v) an unsubstituted, mono-, di-, or tri-substituted aryl group, such as phenyl, naphthyl, phenanthryl, or pyrenyl; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl; wherein the substituents are independently chosen for each occurrence from:
    (A) a lengthening agent L represented by Formula I above;
    (B) —C(O)X$_6$, wherein X$_6$ is as set forth above;
    (C) aryl, haloaryl, $C_3$-$C_7$ cycloalkylaryl, and an aryl group that is mono- or di-substituted with $C_1$-$C_{12}$ alkyl or $C_1$-$C_{12}$ alkoxy;
    (D) $C_1$-$C_{12}$ alkyl, $C_3$-$C_7$ cycloalkyl, $C_3$-$C_7$ cycloalkyoxy ($C_1$-$C_{12}$)alkyl, aryl($C_1$-$C_{12}$)alkyl, aryloxy($C_1$-$C_{12}$)alkyl, mono- or di-($C_1$-$C_{12}$)alkylaryl($C_1$-$C_{12}$)alkyl, mono- or di-($C_1$-$C_{12}$)alkoxyaryl($C_1$-$C_{12}$)alkyl, haloalkyl, and mono($C_1$-$C_{12}$)alkoxy($C_1$-$C_{12}$)alkyl;
    (E) $C_1$-$C_{12}$ alkoxy, $C_3$-$C_7$ cycloalkoxy, cycloalkyloxy($C_1$-$C_{12}$)alkoxy, aryl($C_1$-$C_{12}$)alkoxy, aryloxy($C_1$-$C_{12}$) alkoxy, mono- or di-($C_1$-$C_{12}$)alkylaryl($C_1$-$C_{12}$)alkoxy, and mono- or di-($C_1$-$C_{12}$)alkoxyaryl($C_1$-$C_{12}$)alkoxy;
    (F) amido, amino, mono- or di-alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidyl, hydroxy, acryloxy, methacryloxy, and halogen;
    (G) —OX$_7$ and —N(X$_7$)$_2$, wherein X$_7$ is as set forth above;
    (H) —SX$_{11}$, wherein X$_{11}$ is as set forth above;
    (I) a nitrogen containing ring represented by Formula i, which is set forth above; and
    (J) a group represented by one of Formula ii or iii, which are set forth above;
  (vi) an unsubstituted or mono-substituted group chosen from pyrazolyl, imidazolyl, pyrazolinyl, imidazolinyl, pyrrodlinyl, phenothiazinyl, phenoxazinyl, phenazinyl, or acridinyl, wherein each substituent is independently chosen from a lengthening agent L, $C_1$-$C_{12}$ alkyl, $C_1$-$C_{12}$ alkoxy, phenyl, hydroxy, amino or halogen;
  (vii) a group represented by one of Formula iv or v, which are set forth above;
  (viii) a group represented by Formula vi, which is set forth above; and
  (ix) a lengthening agent L represented by Formula I (above); and
(f) i is an integer chosen from 0 to the total available positions on A, and each $R^4$ is independently chosen for each occurrence from:
  (i) a group represented by $R^5$;
  (ii) —C(O)X$_{24}$, wherein X$_{24}$ is as set forth above;
  (iii) —OX$_7$ and —N(X$_7$)$_2$, wherein X$_7$ is as set forth above;
  (iv) —SX$_{11}$, wherein X$_{11}$ is as set forth above;
  (v) a nitrogen containing ring represented by Formula i, which is set forth above;
  (vi) a group represented by one of Formula ii or iii, which are set forth above; and
  (vii) immediately adjacent $R^4$ groups together form at a group represented by one of Formula vii, viii, or ix, which are set forth above.

Additionally, according to various non-limiting embodiments disclosed herein, the photochromic compound represented by Formula XXII comprises at least one lengthening agent (L) represented by Formula I above. As previously discussed, in Formula I, c, d, e, and f each can be independently chosen from an integer ranging from 1 to 20, inclusive; and d', e' and f' each can be independently chosen from 0, 1, 2, 3, and 4, provided that the sum of d'+e'+f' is at least 1. According to other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f' is at least 2. According to still other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f' is at least 3. According to still other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f' is at least 1.

As discussed with respect to the photochromic compounds set forth above, the photochromic compounds generally represented by Formula XXII can be extended at any available position by substitution with L or an $R^4$ group substituted with L, and/or in any desired direction by numerous combinations of substitutions of available positions with L or $R^4$ groups substituted with L. Thus, for example, although not limiting herein, the fulgides disclosed herein can be extended by selecting at least one of D, G, and at least one $R^4$ to be L or a group substituted with L, so as to enhance the average absorption ratio of the fulgide in at least the activated state. Further, although not limiting herein, as discussed in more detail below, when E is —N($R^5$)—, $R^5$ can be L or can be a group substituted with L.

For example, although not limiting herein, according to one non-limiting embodiment, the A can be thiophene, E can be —N($R^5$)—, each D can be O, and the photochromic compound can be represented by Formula XXIII:

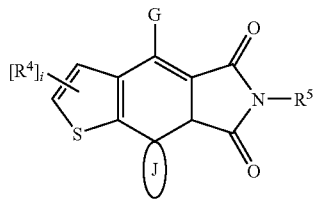

XXIII wherein at least one of: $R^5$, G, or at least one $R^4$ comprises a lengthening agent L.

Thus, according to the above-mentioned non-limiting embodiment, the photochromic compound can be extended by selecting at least one of $R^5$, G, or at least one $R^4$ to be L, or a group substituted with L so as to enhance the average absorption ratio of the fulgide in at least the activated state. For example and without limitation, according to this non-limiting embodiment, the photochromic compound can be represented by Formula XXIV:

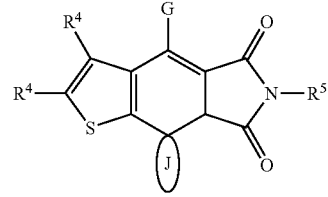

XXIV wherein at least one of: $R^5$, G or $R^4$ is a lengthening agent L.

Further, the photochromic compounds according to various non-limiting embodiments disclosed herein and generally represented by Formula XXII above can have an average absorption ratio at least 1.5 in an activated state as determined according to CELL METHOD. According to other non-limiting embodiments, the photochromic fulgides can have an average absorption ratio ranging from 4 to 20, 3 to 30, or 2.5 to 50 in an activated state as determined according to CELL METHOD. According to still other non-limiting embodiments, the photochromic fulgides can have an average absorption ratio ranging from 1.5 to 50 in an activated state as determined according to CELL METHOD.

A general reaction sequence for synthesizing the photochromic compounds according to various non-limiting embodiments disclosed herein and generally represented by Formula XXII above, and more specifically represented by Formula XXIII above, wherein E is —N($R^5$)— and D is O is depicted below in Reaction Sequence N.

Reaction Sequence N

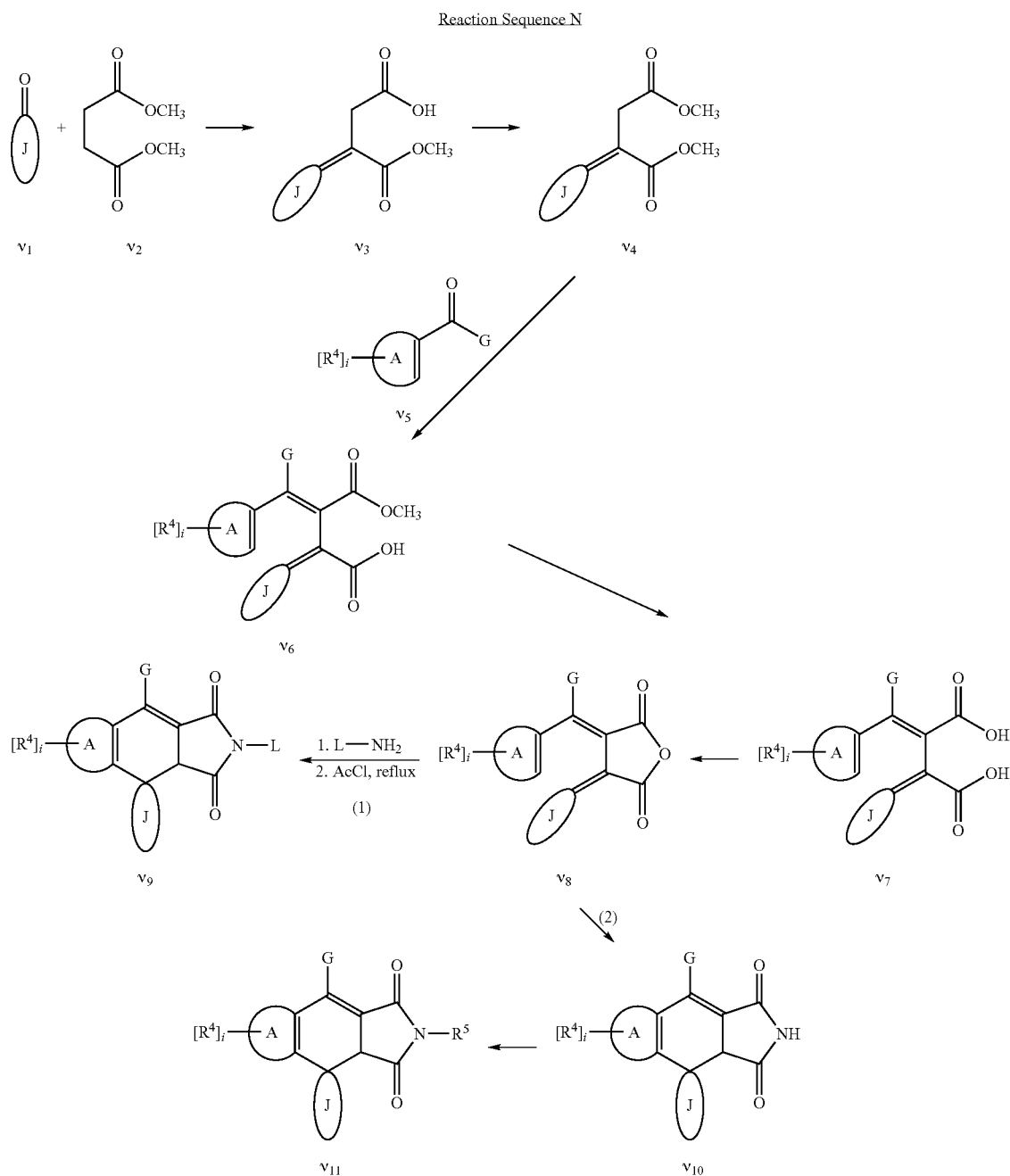

In Reaction Sequence N, an alicyclic ketone represented by Formula $v_1$ is reacted with dimethyl succinate represented by Formula $v_2$ in a Stobbe Condensation to produce the half-ester product represented by Formula $v_3$. The half-ester product represented by Formula $v_3$ is esterified to form the diester product represented by Formula $v_4$. The diester of Formula $v_4$ is reacted with a carbonyl-substituted A group represented by Formula $v_5$ in the Stobbe Condensation to produce the half-ester material represented by Formula $v_6$. As indicated Formula $v_5$, the carbonyl-substituted A group can also be substituted with one or more $R^4$ groups, each of which can comprise a lengthening agent L which is the same or different from the remaining L substituents. The half-ester material represented by Formula $v_7$ is hydrolyzed to produce the diacid material represented by Formula $v_7$. The diacid of Formula $v_7$ is reacted with acetyl chloride in an ether and/or tetrahydrofuran solvent to form the anhydride represented by Formula $v_8$.

As shown in Path (1), the anhydride of Formula $v_8$ can be reacted with an amino substituted lengthening agent L and subsequently reacted with acetyl chloride under reflux conditions to produce the photochromic fulgimide compound represented by Formula $v_9$ according to one non-limiting embodiment disclosed herein. Alternatively, as shown in Path (2), the anhydride of Formula $v_8$ can be reacted with ammonia followed by acetyl chloride to produce the photochromic fulgide compound according to various non-limiting embodiments disclosed herein and represented by Formula $v_{10}$. Further, the photochromic fulgide compound of Formula $v_{10}$ can be further reacted with an appropriate reactant to form the photochromic fulgide compound of Formula $v_{11}$ according to various non-limiting embodiments disclosed herein, wherein the nitrogen is substituted with an $R^5$ group. Further, according to various non-limiting embodiments, the $R^5$ group can be a lengthening agent L, or can comprise a substituent group that is substituted with a lengthening agent L.

Reaction Sequences P, Q and T illustrate three general reaction schemes for substituting a lengthening agent L at various locations on a fulgide.

Reaction Sequence P

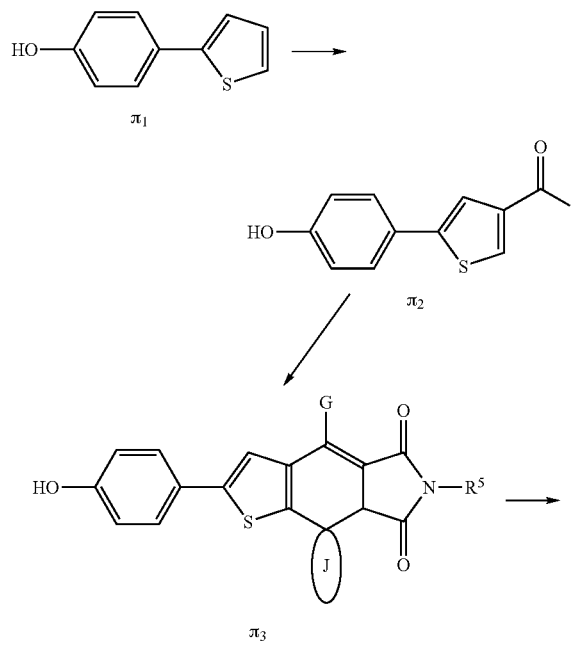

-continued

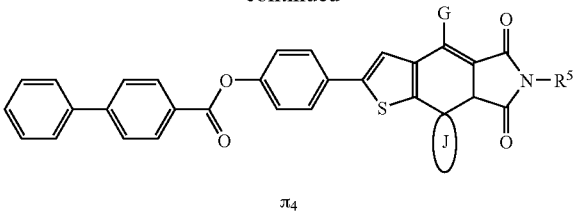

$\pi_4$

In Reaction Sequence P, the hydroxylated compound represented by Formula $\pi_1$ undergoes the Friedel-Crafts reaction to form the carbonyl-substituted group represented by Formula $\pi_2$. The material represented by Formula $\pi_2$ is reacted as described above for the material represented by Formula $v_5$ in Reaction Sequence N to form the hydroxyphenyl substituted thiophenofused fulgide represented by Formula $\pi_3$ in Reaction Sequence P. The fulgide represented by Formula $\pi_3$ is benzoylated with 4-phenylbenzoyl chloride to form the thermally reversible, photochromic compound according to one non-limiting embodiment disclosed herein and represented by Formula $\pi_4$. With additional reference to Formula XXII above, as shown in Formula $\pi_4$, the A group is thiopheno that is substituted with a lengthening agent L. As previously discussed, according to various non-limiting embodiments (and as shown below in Reaction Sequence Q), the $R^5$ group in Formula $\pi_4$ can be a lengthening agent L, or can comprise another substituent group that is substituted with a lengthening agent L. Further, group G can also be a lengthening agent L or can be another substituent group that is substituted with a lengthening agent L (for example, as shown below in Reaction Sequence T).

Reaction Sequence Q

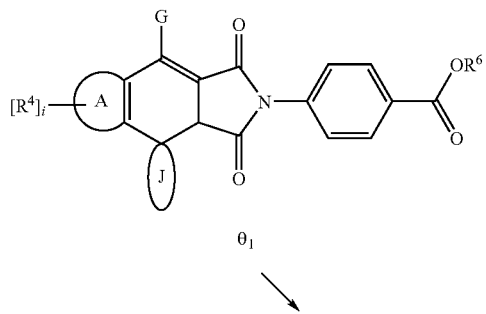

$\theta_1$

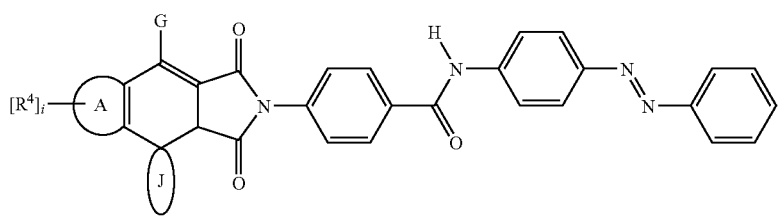

$\theta_2$

In Reaction Sequence Q, the fulgide represented by Formula $\theta_1$ can be made in accordance with Reaction Sequence N with appropriate modifications that will be recognized by those skilled in the art. With additional reference to Formula XXIII above, in Formula $\theta_1$, the $R^5$ group attached to the nitrogen atom is a methyl ester of para-amino benzoic acid. The methyl ester of para-amino benzoic acid is then reacted with 4-aminodiazobenzene, to form the thermally reversible, photochromic compound represented by Formula $\theta_2$ according to one non-limiting embodiment disclosed herein. As previously discussed with reference to Formula XXIII (above), $R^5$ group can be a lengthening agent L or can be another substituent group that is substituted with L. Further, as previously discussed (and as depicted in Reaction Sequence P above) the A group of the thermally reversible, photochromic compound represented by Formula $\theta_2$, optionally can be substituted with one or more $R^4$ groups, each of which may comprise a lengthening agent L that is the same or different from the remaining L substituents. Further, as shown below in Reaction Sequence T (below), the G group in Formula $\theta_2$ can also be a lengthening agent L or can be another substituent group that is substituted with a lengthening agent L.

Reaction Sequence T

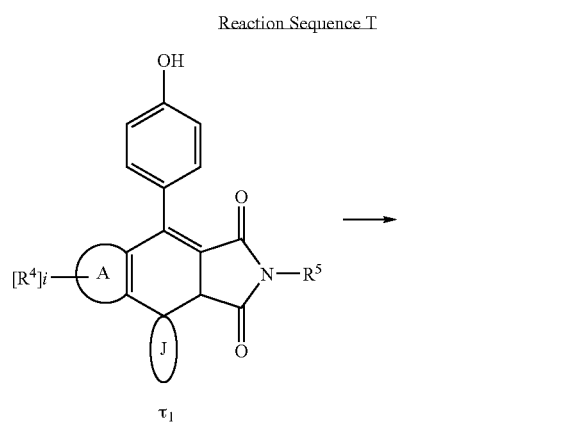

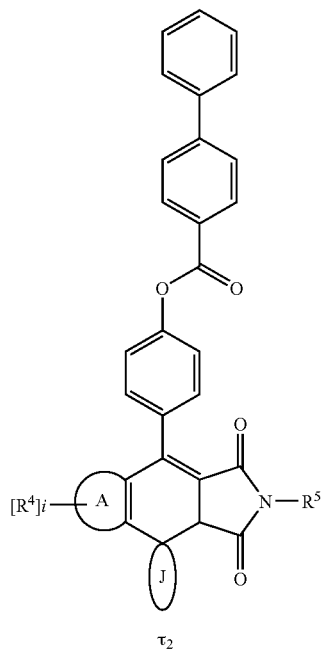

In Reaction Sequence T, the fulgide represented by Formula $\tau_1$ can be made in accordance Reaction Sequence N with appropriate modifications that will be recognized by those skilled in the art. The fulgide represented by formula $\tau_1$ can then be reacted with para-amino benzoylchloride to form the thermally reversible, photochromic compound according to one non-limiting embodiment disclosed herein and represented by Formula $\tau_2$. As previously discussed (and as depicted in Reaction Sequence Q above), the $R^5$ group of the thermally reversible, photochromic compound represented by Formula $\tau_2$ can be a lengthening agent L or can be another substituent group that is substituted with L. Further, as previously discussed (and as depicted in Reaction Sequence P above) the A group of the thermally reversible, photochromic compound represented by Formula $\tau_2$, optionally can be substituted with one or more $R^4$ groups, each of which may comprise a lengthening agent L that is the same or different from the remaining Ls.

As previously discussed, according to various non-limiting embodiments disclosed herein, the photochromic groups (PC) can be non-thermally reversible photochromic groups. For example, according to one non-limiting embodiment, the photochromic group can be non-thermally reversible fulgide represented by Formula XXV:

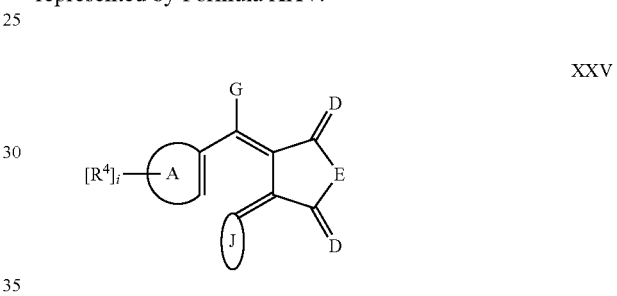

XXV

According to this non-limiting embodiment, A, $R^4$, i, J, G, D, and E are as set forth above with respect to Formula XXII, and provided that the non-thermally reversible photochromic compound comprises at least one lengthening agent L represented by Formula I above. Further, as previously discussed, in Formula I, c, d, e, and f each can be independently chosen from an integer ranging from 1 to 20, inclusive; and d', e' and f' each can be independently chosen from 0, 1, 2, 3, and 4, provided that the sum of d'+e'+f' is at least 1. According to other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f' is at least 2. According to still other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f' is at least 3. According to still other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f' is at least 1.

For example, although not limiting herein, a general reaction sequence for forming a non-thermally reversible photochromic compound represented by Formula XXV follows that of Reaction Sequence N set forth above, except (as shown below in Reaction Sequence Y) the anhydride of Formula $v_8$ can be reacted with an amino substituted lengthening agent L and subsequently reacted with acetyl chloride under reflux conditions to produce the non-thermally reversible photochromic fulgimide compound represented by Formula Ψ₁ according to one non-limiting embodiment disclosed herein.

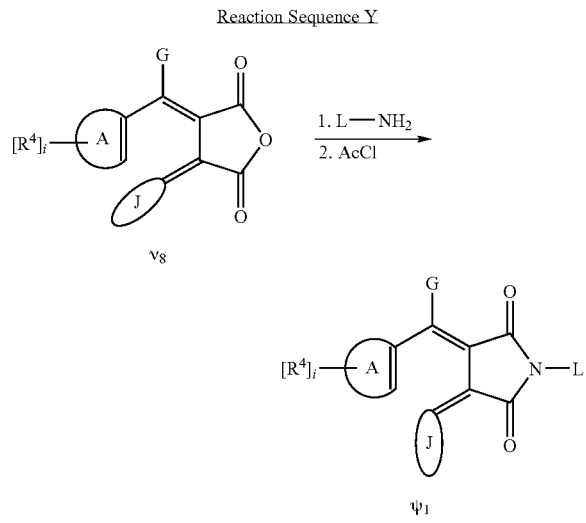

Further, the non-thermally reversible photochromic fulgimide compound represented by Formula Ψ₁ can be substituted with a lengthening agent L in reaction sequences similar to Reaction Sequences P, Q and T (above) with appropriate modifications of the starting materials based upon the above-disclosure, which will be apparent to those skilled in the art.

Another non-limiting embodiment provides a photochromic compound comprising (a) at least one photochromic group (PC) chosen from pyrans, oxazines, and fulgides; and (b) at least one lengthening agent L² attached to the at least one photochromic group, wherein L² is represented by Formula XXVI:

 —[S]ₛ—P'  XXVI wherein:
(i) P' is a group chosen from steroid radicals, terpenoid radicals, alkaloid radicals, and liquid crystal mesogen that is either directly linked to PC or indirectly linked to PC through one or more spacer units ("S") (described below); and
(ii) s' is chosen from 0 to 20 and each S is independently chosen for each occurrence from a spacer unit chosen from:
(A) —(CH₂)ɡ—, —(CF₂)ₕ—, —Si(CH₂)ɡ—, —(Si[(CH₃)₂]O)ₕ—, wherein g is independently chosen for each occurrence from 1 to 20; h is chosen from 1 to 16;
(B) —N(Z)-, —C(Z)═C(Z)-, —C(Z)═N—, —C(Z')-C(Z')-, wherein Z is independently chosen for each occurrence from hydrogen, C₁-C₆ alkyl, cycloalkyl and aryl, and Z' is independently chosen for each occurrence from C₁-C₆ alkyl, cycloalkyl and aryl; and
(C) —O—, —C(O)—, —C≡C—, —N═N—, —S—, —S(O)—, —S(O)(O)—, straight-chain or branched C₁-C₂₄ alkylene residue, said C₁-C₂₄ alkylene residue being unsubstituted, mono-substituted by cyano or halo, or poly-substituted by halo;
provided that when two spacer units comprising heteroatoms are linked together the spacer units are linked so that heteroatoms are not directly linked to each other.

Non-limiting examples of photochromic groups (PC) that are suitable for use in conjunction with the photochromic compounds according to this non-limiting embodiment are set forth above in detail. Further, according to one non-limiting embodiment, the photochromic group PC is a thermally reversible photochromic group.

A non-limiting examples of a steroid radicals from which P' can be chosen is a cholesterolic compound.

Further, in addition to at least one lengthening agent L², the photochromic compound according to various non-limiting embodiments disclosed herein can further comprise one or more R¹ groups substituted on an available position on PC. Suitable R¹ groups are set forth above in detail.

Another non-limiting embodiment provides a photochromic compound chosen from:
(a) 3-phenyl-3-(4-(4-piperidinopiperidino)phenyl)-13,13-dimethyl-indeno[2',3':3,4]naphtho[1,2-b]pyran;
(b) 3-phenyl-3-(4-(4-benzylpiperidino)phenyl)-13,13-dimethyl-indeno[2',3':3,4]naphtho[1,2-b]pyran;
(c) 3-phenyl-3-(4-(4-(3-piperidin-4-yl-propyl)piperidino)phenyl)-13,13-dimethyl-indeno[2',3':3,4]-naphtho[1,2-b]pyran;
(d) 3-phenyl-3-(4-(4-(3-(1-(2-hydroxyethyl)piperidin-4-yl)propyl)piperidino)phenyl)-13,13-dimethyl-indeno[2',3':3,4]naphtho[1,2-b]pyran;
(e) 3-phenyl-3-(4-(4-phenylpiperazine)phenyl)-13,13-dimethyl-indeno[2',3':3,4]naphtho[1,2-b]pyran;
(f) 3-phenyl-3-(4-(4-benzylpiperazine)phenyl)-13,13-dimethyl-indeno[2',3':3,4]naphtho[1,2-b]pyran;
(g) 3-phenyl-3-(4-(4-hexyloxymethyl)piperidino)phenyl)-13,13-dimethyl-indeno[2',3':3,4]naphtho[1,2-b]pyran;
(h) 3-phenyl-3-(4-(4-(4-butyl-phenylcarbamoyl)-piperidin-1-yl)phenyl)-13,13-dimethyl-6-methoxy-7-(4-phenyl-piperazin-1-yl)indeno[2',3':3,4]naphtho[1,2-b]pyran;
(i) 3-phenyl-3-(4-pyrrolidin-1-yl-phenyl)-13,13-dimethyl-6-methoxy-7-(4-phenyl-piperazin-1-yl)indeno[2',3':3,4]naphtho[1,2-b]pyran;
(j) 3-phenyl-3-(4-pyrrolidin-1-yl-phenyl)-13,13-dimethyl-6-methoxy-7-([1,4']bipiperidinyl-1''-yl)indeno[2',3':3,4]naphtho[1,2-b]pyran;
(k) 3-phenyl-3-(4-([1,4']bipiperidinyl-1'-yl)phenyl)-13,13-dimethyl-6-methoxy-7-([1,4']bipiperidinyl-1'-yl)indeno[2',3':3,4]naphtho[1,2-b]pyran;
(l) 3-phenyl-3-(4-([1,4']bipiperidinyl-1'-yl)phenyl)-13,13-dimethyl-6-methoxy-7-(4-benzylpiperidin-1-yl)indeno[2',3':3,4]naphtho[1,2-b]pyran;
(m) 3-phenyl-3-(4-([1,4']bipiperidinyl-1'-yl)phenyl)-13,13-dimethyl-6-methoxy-7-(piperadin-1-yl)indeno[2',3':3,4]naphtho[1,2-b]pyran;
(n) 3-phenyl-3-(4-(4-phenyl-piperazin-1-yl)phenyl)-13,13-dimethyl-6-methoxy-7-(4-phenyl-piperazin-1-yl)indeno[2',3':3,4]naphtho[1,2-b]pyran;
(o) 3-phenyl-3-(4-(4-phenyl-piperazin-1-yl)phenyl)-13,13-dimethyl-6-methoxy-7-(4-(biphenyl-4-carbonyloxy)-piperidin-1-yl)indeno[2',3':3,4]naphtho[1,2-b]pyran;
(p) 3-phenyl-3-(4-(4-phenyl-piperazin-1-yl)phenyl)-13,13-dimethyl-6-methoxy-7-(4-(4-hexyloxy-benzoyloxy)-piperidin-1-yl)indeno[2',3':3,4]naphtho[1,2-b]pyran;
(q) 3-phenyl-3-(4-(4-phenyl-piperazin-1-yl)phenyl)-13,13-dimethyl-6-methoxy-7-(4-(4-hexylbenzoyloxy)-piperidin-1-yl)indeno[2',3':3,4]naphtho[1,2-b]pyran;
(r) 3-phenyl-3-(4-(4-phenyl-piperazin-1-yl)phenyl)-13,13-dimethyl-6-methoxy-7-(4-(4'-octyloxy-biphenyl-4-carbonyloxy)-piperidin-1-yl)indeno[2',3':3,4]naphtho[1,2-b]pyran;
(s) 3-phenyl-3-(4-(4-phenyl-piperazin-1-yl)phenyl)-13,13-dimethyl-6-methoxy-7-{4-[17-(1,5-dimethyl-hexyl)-10, (t) 3-phenyl-3-(4-(4-pyrrolidinylphenyl)-13,13-dimethyl-6-methoxy-7-(-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl}indeno[2',3':3,4]naphtho[1,2-b]pyran;

(u) 3-phenyl-3-(4-(1-hydroxypiperidin-1-yl)-phenyl)-13,13-dimethyl-6-methoxy-7-(4-phenyl-piperazin-1-yl)indeno[2',3':3,4]naphtho[1,2-b]pyran;

(v) 3-phenyl-3-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl}-phenyl)-13,13-dimethyl-6-methoxy-7-(4-phenyl-piperazin-1-yl)indeno[2',3':3,4]naphtho[1,2-b]pyran;

(w) 3-phenyl-3-(4-(4-hexylbenzoyloxy)-piperidin-1-yl)phenyl)-13,13-dimethyl-6-methoxy-7-(4-(4-hexylbenzoyloxy)-piperidin-1-yl)indeno[2',3':3,4]naphtho[1,2-b]pyran;

(x) 3-phenyl-3-(4-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl}-phenyl)-13,13-dimethyl-6-methoxy-7-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl}-)indeno[2',3':3,4]naphtho[1,2-b]pyran;

(y) 3-phenyl-3-(4-{4-(biphenyl-4-carbonyloxy]-piperidin-1-yl}-phenyl)-13,13-dimethyl-6-methoxy-7-4-(4-(biphenyl-4-carbonyloxy)-piperidin-1-yl}-)indeno[2',3':3,4]naphtho[1,2-b]pyran;

(z) 3-phenyl-3-(4-(4-phenyl-piperazin-1-yl)phenyl)-13,13-dimethyl-6-methoxy-7-(4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyl]-piperazin-1-yl)indeno[2',3':3,4]naphtho[1,2-b]pyran;

(aa) 3-phenyl-3-(4-(4-hexylbenzoyloxy)-piperadin-1-yl)phenyl)-13-hydroxy-13-ethyl-6-methoxy-7-(4-phenyl-piperazin-1-yl)-indeno[2',3':3,4]naphtho[1,2-b]pyran;

(bb) 3-phenyl-3-(4-(4-fluorobenzoyloxy)-piperadin-1-yl)phenyl)-13-hydroxy-13-ethyl-6-methoxy-7-(4-phenyl-piperazin-1-yl)-indeno[2',3':3,4]naphtho[1,2-b]pyran;

(cc) 3-phenyl-3-(4-(pyrrolidin-1-yl)phenyl)-3-hydroxy-13-ethyl-6-methoxy-7-(4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperadin-1-yl)indeno[2',3':3,4]naphtho[1,2-b]pyran;

(dd) 3-phenyl-3-(4-(pyrrolidin-1-yl)phenyl)-13-hydroxy-13-ethyl-6-methoxy-7-(4-hexylbenzoyloxy-piperadin-1-yl)-indeno[2',3':3,4]naphtho[1,2-b]pyran;

(ee) 3-phenyl-3-(4-(4-phenyl-piperazin-1-yl)phenyl)-13,13-dimethyl-6-methoxy-7-(4-(4-(4-hexylbenzoyloxy)phenyl)piperazin-1-yl)indeno[2',3':3,4]naphtho[1,2-b]pyran;

(ff) 3-phenyl-3-(4-(pyrrolidin-1-yl)phenyl)-13-hydroxy-13-ethyl-6-methoxy-7-(4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyl]-piperazin-1-yl)-indeno[2',3':3,4]naphtho[1,2-b]pyran;

(gg) 3-phenyl-3-(4-(4-phenylpiperazin-1-yl)phenyl)-13,13-dimethyl-6-methoxy-7-(4-(4-(4-phenyl-piperazin-1-yl)-4-oxo-butanoyl)-piperazine-1-yl)-indeno[2',3':3,4]naphtho[1,2-b]pyran;

(hh) 3-phenyl-3-(4-(4-phenylpiperazin-1-yl)phenyl)-13,13-dimethyl-6-methoxy-7-(4-(4-(4-fluorobenzoyloxy)phenyl)piperazin-1-yl)indeno[2',3':3,4]naphtho[1,2-b]pyran;

(ii) 3-phenyl-3-(4-(4-phenylpiperazin-1-yl)phenyl)-13,13-dimethyl-6-methoxy-7-(4-(4-(4-biphenylcarbonyloxy)phenyl)piperazin-1-yl)indeno[2',3':3,4]naphtho[1,2-b]pyran;

(jj) 3-phenyl-3-(4-(4-phenylpiperazin-1-yl)phenyl)-13,13-dimethyl-6-methoxy-7-(4-(4-(4'-octyloxy-biphenyl-4-carbonyloxy)phenyl)piperazin-1-yl)indeno[2',3':3,4]naphtho[1,2-b]pyran;

(kk) 3-phenyl-3-(4-(4-phenyl-piperazin-1-yl)phenyl)-13,13-dimethyl-6-methoxy-7-(4-(4-(4-hexyloxyphenylcarbonyloxy)phenyl)piperazin–1-yl)indeno[2',3':3,4]naphtho[1,2-b]pyran;

(ll) 3-phenyl-3-(4-(4-phenyl-piperazin-1-yl)phenyl)-13,13-dimethyl-6-methoxy-7-{4-(4-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-phenyl)-piperidin-1-yl}-indeno[2',3':3,4]naphtho[1,2-b]pyran;

(mm) 3-phenyl-3-(4-(4-phenyl-piperazin-1-yl)phenyl)-13,13-dimethyl-6-methoxy-7-(4-(4-(4-hexylbenzoyloxy)benzoyloxy)-phenyl)-piperazin-1-yl)indeno[2',3':3,4]naphtho[1,2-b]pyran;

(nn) 3-phenyl-3-(4-(4-phenyl-piperazin-1-yl)phenyl)-13-hydroxy-13-ethyl-6-methoxy-7-(4-(4-(4-hexylbenzoyloxy)phenyl)piperazin-1-yl)indeno[2',3':3,4]naphtho[1,2-b]pyran;

(oo) 3-phenyl-3-(4-(4-phenyl-piperazin-1-yl)phenyl)-13,13-dimethyl-6-methoxy-7-(4-(4-(4-(2-fluorobenzoyloxy)benzoyloxy)phenyl)piperazin-1-yl)indeno[2',3':3,4]naphtho[1,2-b]pyran;

(pp) 3-phenyl-3-(4-(4-phenyl-piperazin-1-yl)phenyl)-13,13-dimethyl-6-methoxy-7-(4-(4-(4-(4-fluorobenzoyloxy)benzoyloxy)-phenyl)-piperazin-1-yl)indeno[2',3':3,4]naphtho[1,2-b]pyran;

(qq) 3-phenyl-3-(4-(pyrrolidin-1-yl)phenyl)-13-hydroxy-13-ethyl-6-methoxy-7-(4-(4-(4-hexylbenzoyloxy)phenyl)piperazin-1-yl)indeno[2',3':3,4]naphtho[1,2-b]pyran;

(rr) 3-phenyl-3-(4-(4-phenyl-piperazin-1-yl)phenyl)-13,13-dimethyl-6-methoxy-7-(4-(4-(4-(4-hexylbenzoyloxy)benzoyloxy)-benzoyloxy)phenyl)piperazin-1-yl)indeno[2',3':3,4]naphtho[1,2-b]pyran;

(ss) 3-phenyl-3-(4-(pyrrolidin-1-yl)phenyl)-13,13-dimethyl-6-methoxy-7-(4-hexylbenzoyloxy)-indeno[2',3':3,4]naphtho[1,2-b]pyran;

(tt) 3-phenyl-3-(4-(pyrrolidin-1-yl)phenyl)-13,13-dimethyl-6-methoxy-7-(4-(4-hexylbenzoyloxy)benzoyloxy)-indeno[2',3':3,4]naphtho[1,2-b]pyran;

(uu) 3-phenyl-3-(4-(pyrrolidin-1-yl)phenyl)-13,13-dimethyl-6-methoxy-7-(4-(4-(4-hexylbenzoyloxy)benzoyloxy)benzoyloxy)indeno[2',3':3,4]naphtho[1,2-b]pyran;

(vv) 3-phenyl-3-(4-(pyrrolidin-1-yl)phenyl)-13,13-dimethyl-6-methoxy-7-(4-(4-(4-(4-hexylbenzoyloxy)benzoyloxy)-benzoyloxy)benzoyloxy)-indeno[2',3':3,4]naphtho[1,2-b]pyran;

(ww) 3-phenyl-3-(4-(4-methoxyphenyl)-piperazin-1-yl))phenyl)-13,13-dimethyl-6-methoxy-7-(4-(4-(3-phenyl-prop-2-ynoyloxy)phenyl)piperazin-1-yl)-indeno[2',3':3,4]naphtho[1,2-b]pyran;

(xx) 3-phenyl-3-(4-(4-(4-hexylbenzoyloxy)phenyl)piperazin-1-yl)phenyl-13,13-dimethyl-6-methoxy-7-(4-phenylpiperazin-1-yl)-indeno[2',3':3,4]naphtho[1,2-b]pyran;

(yy) 3-phenyl-3-(4-(4'-octyloxybiphenyl-4-carbonyloxy)-piperazin-1-yl))phenyl)-13,13-dimethyl-6-methoxy-7-(4-(phenyl)-piperazin-1-yl)-indeno[2',3':3,4]naphtho[1,2-b]pyran;

(zz) 3-phenyl-3-(4-(4-methoxyphenyl)piperazin-1-yl))phenyl)-13,13-dimethyl-6-methoxy-7-(3-(4-hexylbenzoyloxyphenyl)piperazin-1-yl)-indeno[2',3':3,4]naphtho[1,2-b]pyran;

(aaa) 3-(4-methoxyphenyl)-3-(4-(4-methoxyphenyl)piperazin-1-yl)phenyl)-13-ethyl-13-hydroxy-6-methoxy-7-(4-(4-(4-hexylbenzoyloxy)phenyl)piperazin-1-yl)indeno[2',3':3,4]naphtho[1,2-b]pyran;

(bbb) 3-phenyl-3-{4-(pyrrolidin-1-yl)phenyl)-13-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxy]-13-ethyl-6-methoxy-7-(4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperadin-1-yl)-indeno[2',3':3,4]naphtho[1,2-b]pyran;

(ccc) 3-phenyl-3-(4-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl}-phenyl)-13-ethyl-13-hydroxy-6-methoxy-7-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy-piperidin-1-yl}-)indeno[2',3':3,4]naphtho[1,2-b]pyran;

(ddd) 3-phenyl-3-{4-(pyrrolidin-1-yl)phenyl)-13,13-dimethyl-6-methoxy-7-(4-(4-(3-phenyl-3-{4-(pyrrolidin-1-yl)phenyl}-13,13-dimethyl-6-methoxy-indeno[2',3':3,4]naphtho[1,2-b]pyran-7-yl)-piperadin-1-yl)oxycarbonyl)phenyl)phenyl)cabonyloxy)-indeno[2',3':3,4]naphtho[1,2-b]pyran;

(eee) 3-{4-[4-(4-methoxy-phenyl)-piperazin-1-yl]-phenyl}-3-phenyl-7-methoxycarbonyl-3H-naphtho[2,1-b]pyran;

(fff) 3-{4-[4-(4-methoxy-phenyl)-piperazin-1-yl]-phenyl}-3-phenyl-7-hydroxycarbonyl-3H-naphtho[2,1-b]pyran;

(ggg) 3-{4-[4-(4-methoxy-phenyl)-piperazin-1-yl]-phenyl}-3-phenyl-7-(4-phenyl-(phen-1-oxy)carbonyl)-3H-naphtho[2,1-b]pyran;

(hhh) 3-{4-[4-(4-methoxy-phenyl)-piperazin-1-yl]-phenyl}-3-phenyl-7-(N-(4-((4-dimethylamino)phenyl)diazenyl)phenyl)carbamoyl-3H-naphtho[2,1-b]pyran;

(iii) 2-phenyl-2-{4-[4-(4-methoxy-phenyl)-piperazin-1-yl]-phenyl}-benzofuro[3',2':7,8]benzo[b]pyran;

(jjj) 2-phenyl-2-{4-[4-(4-methoxy-phenyl)-piperazin-1-yl]-phenyl}-benzothieno[3',2':7,8]benzo[b]pyran;

(kkk) 7-{17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy}-2-phenyl-2-(4-pyrrolidin-1-yl-phenyl)-6-methoxycarbonyl-2H-benzo[b]pyran;

(lll) 2-phenyl-2-{4-[4-(4-methoxy-phenyl)-piperazin-1-yl]-phenyl}-9-hydroxy-8-methoxycarbonyl-2H-naphtho[1,2-b]pyran;

(mmm) 2-phenyl-2-{4-[4-(4-methoxy-phenyl)-piperazin-1-yl]-phenyl}-9-hydroxy-8-(N-(4-butyl-phenyl))carbamoyl-2H-naphtho[1,2-b]pyran;

(nnn) 2-phenyl-2-{4-[4-(4-methoxy-phenyl)-piperazin-1-yl]-phenyl}-9-hydroxy-8-(N-(4-phenyl)phenyl)carbamoyl-2H-naphtho[1,2-b]pyran;

(ooo) 1,3,3-trimethyl-6'-(4-ethoxycarbonyl)-piperidin-1-yl)-spiro[indoline-2,3'-3H-naphtho[2,1-b][1,4]oxazine];

(ppp) 1,3,3-trimethyl-6'-(4-[N-(4-butylphenyl)carbamoyl]-piperidin-1-yl)-spiro[indoline-2,3'-3H-naphtho[2,1-b][1,4]oxazine];

(qqq) 1,3,3-trimethyl-6'-(4-(4-methoxyphenyl)piperazin-1-yl)-spiro[indoline-2,3'-3H-naphtho[2,1-b][1,4]oxazine];

(rrr) 1,3,3-trimethyl-6'-(4-(4-hydroxyphenyl)piperazin-1-yl)-spiro[indoline-2,3'-3H-naphtho[2,1-b][1,4]oxazine];

(sss) 1,3,3,5,6-pentamethyl-7'-(4-(4-methoxyphenyl)piperazin-1-yl)-spiro[indoline-2,3'-3H-naphtho[2,1-b][1,4]oxazine];

(ttt) 1,3-diethyl-3-methyl-5-methoxy-6'-(4-(4'-Hexyloxy-biphenyl-4-carbonyloxy)-piperidin-1-yl)-spiro[indoline-2,3'-3H-naphtho[2,1-b][1,4]oxazine];

(uuu) 1,3-diethyl-3-methyl-5-[4-(4-pentadecafluoroheptyloxy-phenylcarbamoyl)-benzyloxy]-6'-(4-(4'-hexyloxy-biphenyl-4-carbonyloxy)-piperidin-1-yl)-spiro[indoline-2,3'-3H-naphtho[2,1-b][1,4]oxazine];

(vvv) 2-phenyl-2-{4-[4-(4-methoxy-phenyl)-piperazin-1-yl]-phenyl}-5-carbomethoxy-8-(N-(4-phenyl)phenyl)carbamoyl-2H-naphtho[1,2-b]pyran;

(www) 2-phenyl-2-{4-[4-(4-methoxy-phenyl)-piperazin-1-yl]-phenyl}-5-carbomethoxy-8-(N-(4-phenyl)phenyl)carbamoyl-2H-fluoantheno[1,2-b]pyran;

(xxx) 2-phenyl-2-{4-[4-(4-methoxy-phenyl)-piperazin-1-yl]-phenyl}-5-carbomethoxy-11-(4-{17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy}phenyl)-2H-fluoantheno[1,2-b]pyran;

(yyy) 1-(4-carboxybutyl)-6-(4-(4-propylphenyl)carbonyloxy)phenyl)-3,3-dimethyl-6'-(4-ethoxycarbonyl)-piperidin-1-yl)-spiro[(1,2-dihydro-9H-dioxolano[4',5':6,7]indoline-2,3'-3H-naphtho[2,1-b][1,4]oxazine];

(zzz) 1-(4-carboxybutyl)-6-(4-(4-propylphenyl)carbonyloxy)phenyl)-3,3-dimethyl-7'-(4-ethoxycarbonyl)-piperidin-1-yl)-spiro[(1,2-dihydro-9H-dioxolano[4',5':6,7]indoline-2,3'-3H-naphtho[1,2-b][1,4]oxazine];

(aaaa) 1,3-diethyl-3-methyl-5-(4-{17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy}phenyl)-6'-(4-(4'-hexyloxy-biphenyl-4-carbonyloxy)-piperidin-1-yl)-spiro[indoline-2,3'-3H-naphtho[2,1-b][1,4]oxazine];

(bbbb) 1-butyl-3-ethyl-3-methyl-5-methoxy-7'-(4-(4'-Hexyloxy-biphenyl-4-carbonyloxy)-piperidin-1-yl)-spiro[indoline-2,3'-3H-naphtho[1,2-b][1,4]oxazine];

(cccc) 2-phenyl-2-{4-[4-(4-methoxy-phenyl)-piperazin-1-yl]-phenyl}-5-methoxycarbonyl-6-methyl-2H-9-(4-(4-propylphenyl)carbonyloxy)phenyl)(1,2-dihydro-9H-dioxolano[4',5':6,7]naphtho[1,2-b]pyran;

(dddd) 3-(4-methoxyphenyl)-3-(4-(4-methoxyphenyl)piperazin-1-yl)phenyl)-13-ethyl-13-hydroxy-6-methoxy-7-(4-(4-propylphenyl)carbonyloxy)phenyl)-[1,2-dihydro-9H-dioxolano[4",5":6,7]][indeno[2',3':3,4]]naphtho[1,2-b]pyran;

(eeee) 3-phenyl-3-(4-(4-methoxyphenyl)piperazin-1-yl)phenyl)-13-ethyl-13-hydroxy-6-methoxy-7-(4-(4-hexylphenyl)carbonyloxy)phenyl)-[1,2-dihydro-9H-dioxolano[4",5":5,6]][indeno[2',3':3,4]]naphtho[1,2-b]pyran;

(ffff) 4-(4-((4-cyclohexylidene-1-ethyl-2,5-dioxopyrrolin-3-ylidene)ethyl)-2-thienyl)phenyl-(4-propyl)benzoate;

(gggg) 4-(4-((4-adamantan-2-ylidene-1-(4-(4-hexylphenyl)carbonyloxy)phenyl)-2,5-dioxopyrrolin-3-ylidene)ethyl)-2-thienyl)phenyl-(4-propyl)benzoate;

(hhhh) 4-(4-((4-adamantan-2-ylidene-2,5-dioxo-1-(4-(4-(4-propylphenyl)piperazinyl)phenyl)pyrrolin-3-ylidene)ethyl)-2-thienyl)phenyl (4-propyl)benzoate;

(iiii) 4-(4-((4-adamantan-2-ylidene-2,5-dioxo-1-(4-(4-(4-propylphenyl)piperazinyl)phenyl)pyrrolin-3-ylidene)ethyl)-1-methylpyrrol-2-yl)phenyl (4-propyl)benzoate;

(jjjj) 4-(4-((4-adamantan-2-ylidene-2,5-dioxo-1-(4-{17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy}phenyl)pyrrolin-3-ylidene)ethyl)-1-methylpyrrol-2-yl)phenyl (4-propyl)benzoate;

(kkkk) 4-(4-methyl-5,7-dioxo-6-(4-(4-(4-propylphenyl)piperazinyl)phenyl)spiro[8,7a-dihydrothiapheno[4,5-f]isoindole-8,2'-adamantane]-2-yl)phenyl (4-propyl)phenyl benzoate;

(llll) N-(4-{17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy}phenyl-6,7-dihydro-4-methyl-2-phenylspiro(5,6-benzo[b]thiophenedicarboxylmide-7,2-tricyclo[3.3.1.1]decane);

(mmmm) N-cyanomethyl-6,7-dihydro-2-(4-(4-(4-propylphenyl)piperazinyl)phenyl)-4-methylspiro(5,6-benzo[b]thiophenedicarboxylmide-7,2-tricyclo[3.3.1.1]decane);

(nnnn) N-phenylethyl-6,7-dihydro-2-(4-(4-(4-hexylbenzoyloxy)phenyl)piperazin–1-yl)phenyl-4-methylspiro(5,6-benzo[b]thiophenedicarboxylmide-7,2-tricyclo[3.3.1.1]decane);

(oooo) N-phenylethyl-6,7-dihydro-2-(4-(4-(4-hexylbenzoyloxy)phenyl)piperazin–1-yl)phenyl-4-cyclopropyl spiro (5,6-benzo[b]thiophenedicarboxylmide-7,2-tricyclo[3.3.1.1]decane);

(pppp) N-phenylethyl-6,7-dihydro-2-(4-(4-(4-hexylbenzoyloxy)phenyl)piperazin–1-yl)phenyl-4-cyclopropyl spiro (5,6-benzo[b]furodicarboxylmide-7,2-tricyclo[3.3.1.1]decane);

(qqqq) N-cyanomethyl-6,7-dihydro-4-(4-(4-(4-hexylbenzoyloxy)phenyl)piperazin-1-yl)phenyl-2-phenylspiro(5,6-benzo[b]thiophenedicarboxylmide-7,2-tricyclo[3.3.1.1]decane);

(rrrr) N-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyl-6,7-dihydro-2-(4-methoxyphenyl)phenyl-4-methylspiro(5,6-benzo[b]thiophenedicarboxylmide-7,2-tricyclo[3.3.1.1]decane);

(ssss) N-cyanomethyl-2-(4-(6-(4-butylphenyl)carbonyloxy-(4,8-dioxabicyclo[3.3.0]oct-2-yl))oxycarbonyl)phenyl-6,7-dihydro-4-cyclopropylspiro(5,6-benzo[b]thiophenedicarboxylmide-7,2-tricyclo[3.3.1.1]decane);

(tttt) 6,7-dihydro-N-methoxycarbonylmethyl-4-(4-(6-(4-butylphenyl)carbonyloxy-(4,8-dioxabicyclo[3.3.0]oct-2-yl))oxycarbonyl)phenyl-2-phenylspiro(5,6-benzo[b]thiophenedicarboxylmide-7,2-tricyclo[3.3.1.1]decane);

(uuuu) 3-phenyl-3-(4-(4-phenyl-piperazin-1-yl)phenyl)-13,13-dimethyl-6-methoxy-7-(4-(4-(4-(4-(6-(4-(4-(4-(4-nonylphenylcabonyloxy)phenyl)oxycarbonyl)phenoxy)hexyloxy)benzoyloxy)phenyl)piperazin-1-yl)indeno[2',3':3,4]naphtho[1,2-b]pyran;

(vvvv) 3-phenyl-3-(4-(4-phenyl-piperazin-1-yl)phenyl)-13-hydroxy-13-ethyl-6-methoxy-7-(4-(4-(4-(4-(6-(4-(4-(4-(4-nonylphenylcabonyloxy)phenyl)oxycarbonyl)phenoxy)hexyloxy)benzoyloxy)phenyl)piperazin-1-yl)indeno[2',3':3,4]naphtho[1,2-b]pyran; and (wwww) 3-phenyl-3-(4-pyrrolidinylphenyl)-13,13-dimethyl-6-methoxy-7-(4-(4-(4-(4-(6-(4-(4-(4-nonylphenylcabonyloxy)phenyl)oxycarbonyl)phenoxy)hexyloxy)phenyl)piperazin-1-yl)indeno[2',3':3,4]naphtho[1,2-b]pyran.

The thermally reversible photochromic compounds according to various non-limiting embodiments disclosed herein can be used in a variety of applications to provide photochromic and/or dichroic properties.

One non-limiting embodiment provides a photochromic article comprising an organic host material and a photochromic amount of the photochromic compound comprising at least one photochromic group chosen from pyrans, oxazines, and fulgides; and (b) at least one lengthening agent L represented by Formula I and attached to the at least one photochromic group, connected to at least a portion of the organic host material. As used herein the term "connected to" means in direct contact with an object or indirect contact with an object through one or more other structures or materials, at least one of which is in direct contact with the object. Further, according to this non-limiting embodiment, the photochromic compound can be connected to at least a portion of the host by incorporation into the host material or by application onto the host material, for example, as part of a coating or layer.

Non-limiting examples of organic host materials that may be used in conjunction with various non-limiting embodiments disclosed herein include polymeric materials, for example, homopolymers and copolymers, prepared from the monomers and mixtures of monomers disclosed in U.S. Pat. No. 5,962,617 and in U.S. Pat. No. 5,658,501 from column 15, line 28 to column 16, line 17, the disclosures of which U.S. patents are specifically incorporated herein by reference. For example, such polymeric materials can be thermoplastic or thermoset polymeric materials, can be transparent or optically clear, and can have any refractive index required. Non-limiting examples of such disclosed monomers and polymers include: polyol(allyl carbonate) monomers, e.g., allyl diglycol carbonates such as diethylene glycol bis(allyl carbonate), which monomer is sold under the trademark CR-39 by PPG Industries, Inc.; polyurea-polyurethane (polyurea-urethane) polymers, which are prepared, for example, by the reaction of a polyurethane prepolymer and a diamine curing agent, a composition for one such polymer being sold under the trademark TRIVEX by PPG Industries, Inc.; polyol(meth)acryloyl terminated carbonate monomer; diethylene glycol dimethacrylate monomers; ethoxylated phenol methacrylate monomers; diisopropenyl benzene monomers; ethoxylated trimethylol propane triacrylate monomers; ethylene glycol bismethacrylate monomers; poly(ethylene glycol) bismethacrylate monomers; urethane acrylate monomers; poly (ethoxylated bisphenol A dimethacrylate); poly(vinyl acetate); poly(vinyl alcohol); poly(vinyl chloride); poly(vinylidene chloride); polyethylene; polypropylene; polyurethanes; polythiourethanes; thermoplastic polycarbonates, such as the carbonate-linked resin derived from bisphenol A and phosgene, one such material being sold under the trademark LEXAN; polyesters, such as the material sold under the trademark MYLAR; poly(ethylene terephthalate); polyvinyl butyral; poly(methyl methacrylate), such as the material sold under the trademark PLEXIGLAS, and polymers prepared by reacting polyfunctional isocyanates with polythiols or polyepisulfide monomers, either homopolymerized or co- and/or terpolymerized with polythiols, polyisocyanates, polyisothiocyanates and optionally ethylenically unsaturated monomers or halogenated aromatic-containing vinyl monomers. Also contemplated are copolymers of such monomers and blends of the described polymers and copolymers with other polymers, for example, to form block copolymers or interpenetrating network products.

According to one specific non-limiting embodiment, the organic host material is chosen from polyacrylates, poly-methacrylates, poly($C_1$-$C_{12}$)alkyl methacrylates, polyoxy(alkylene methacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), poly(vinylpyrrolidone), poly((meth)acrylamide), poly(dimethyl acrylamide), poly(hydroxyethyl methacrylate), poly((meth)acrylic acid), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate)monomers, mono-functional acrylate monomers, mono-functional methacrylate monomers, polyfunctional acrylate monomers, polyfunctional methacrylate monomers, diethylene glycol dimethacrylate monomers, diisopropenyl benzene monomers, alkoxylated polyhydric alcohol monomers and diallylidene pentaerythritol monomers.

According to another specific non-limiting embodiment, the organic host material is a homopolymer or copolymer of monomer(s) chosen from acrylates, methacrylates, methyl methacrylate, ethylene glycol bis methacrylate, ethoxylated bisphenol A dimethacrylate, vinyl acetate, vinylbutyral, urethane, thiourethane, diethylene glycol bis(allyl carbonate), diethylene glycol dimethacrylate, diisopropenyl benzene, and ethoxylated trimethylol propane triacrylate.

Further, according to various non-limiting embodiments disclosed herein, the organic host material can form an optical element or portion thereof. Non-limiting examples of optical elements include ophthalmic elements, display elements, windows, and mirrors. As used herein the term "optical" means pertaining to or associated with light and/or vision. For example, although not limiting herein, according to various non-limiting embodiments, the optical element or device can be chosen from ophthalmic elements and devices, display elements and devices, windows, mirrors, and active and passive liquid crystal cell elements and devices.

As used herein the term "ophthalmic" means pertaining to or associated with the eye and vision. Non-limiting examples of ophthalmic elements include corrective and non-corrective lenses, including single vision or multi-vision lenses, which may be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intraocular lenses, magnifying lenses, and protective lenses or visors. As used herein the term "display" means the visible or machine-readable representation of information in words, numbers, symbols, designs or drawings. Non-limiting examples of display elements and devices include screens, monitors, and security elements, including without limitation, security marks and authentication marks. As used herein the term "window" means an aperture adapted to permit the transmission of radiation therethrough. Non-limiting examples of windows include automotive and aircraft transparencies, filters, shutters, and optical switches. As used herein the term "mirror" means a surface that specularly reflects a large fraction of incident light.

For example, in one non-limiting embodiment, the organic host material is an ophthalmic element, and more particularly, is an ophthalmic lens.

Further, it is contemplated that the photochromic compounds disclosed herein can be used alone or in conjunction with at least one other complementary organic photochromic compound having at least one activated absorption maxima within the range of 300 nm to 1000 nm, inclusive (or substances containing the same). For example, the photochromic compound disclosed herein can be combined with at least one other conventional organic photochromic compound such that the combination of photochromic compound, when activated, exhibits a desired hue. Non-limiting examples of suitable conventional organic photochromic compounds include those photochromic pyrans, oxazines, fulgides, and fulgimides set forth above. Other complementary photochromic compounds include, for example, photochromic metal-dithizonates, for example mercury dithizonate, which are described in U.S. Pat. No. 3,361,706.

For example, it is contemplated that the photochromic compounds disclosed herein can be used alone or in conjunction with another conventional organic photochromic compound (as discussed above), in amounts or ratios such that the organic host material into which the photochromic compounds are incorporated, or onto which the organic host materials are applied, can exhibit a desired color or colors, either in an activated or a "bleached" state. Thus the amount of the photochromic compounds used is not critical provided that a sufficient amount is present to produce a desired photochromic effect. As used herein, the term "photochromic amount" refers to the amount of the photochromic compound necessary to produce the desired photochromic effect.

Another non-limiting embodiment provides a photochromic article comprising a substrate, and an at least partial coating of a coating composition having a photochromic amount of a photochromic compound comprising (a) at least one photochromic group chosen from pyrans, oxazines, and fulgides; and (b) at least one lengthening agent L represented by Formula I and attached to the at least one photochromic group, connected to at least a portion of at least one surface thereof of the substrate. Further, although not limiting herein, at least a portion of the at least partial coating can be at least partially set. As used herein the term "set" means to fix in a desired orientation.

For example, according to the above-mentioned non-limiting embodiment, the coating composition can be chosen from, without limitation, polymeric coating compositions, paints, and inks. Further, in addition to the photochromic compounds disclosed herein, the coating compositions according to various non-limiting embodiments can further comprise at least one other conventional organic photochromic compounds having at least one activated absorption maxima within the range of 300 nm to 1000 nm, inclusive.

Non-limiting examples of suitable substrates to which the coating composition comprising the photochromic amount of the photochromic compounds can be applied include glass, masonry, textiles, ceramics, metals, wood, paper and polymeric organic materials. Non-limiting examples of suitable polymeric organic materials are set forth above.

Still other non-limiting embodiments provide optical elements comprising a substrate and an at least partial coating comprising at least one photochromic compound comprising (a) at least one photochromic group chosen from pyrans, oxazines, and fulgides; and (b) at least one lengthening agent L represented by Formula I and attached to the at least one photochromic group, connected to at least a portion of the substrate. Non-limiting examples of optical elements include, ophthalmic elements, display elements, windows, and mirrors. For example, according to one non-limiting embodiment, the optical element is an ophthalmic element, and the substrate is an ophthalmic substrate chosen from corrective and non-corrective lenses, partially formed lenses, and lens blanks.

Although not limiting herein, the optical elements according to various non-limiting embodiments disclosed herein can comprise any amount of the photochromic compound necessary to achieve the desired optical properties, such as but not limited to, photochromic properties and dichroic properties.

Other non-limiting examples of substrates that are suitable for use in conjunction with the foregoing non-limiting embodiment include untinted substrates, tinted substrates, photochromic substrates, tinted-photochromic substrates, linearly polarizing substrates, circularly polarizing substrates, elliptically polarizing substrates, and reflective substrates. As used herein with reference to substrates the term "untinted" means substrates that are essentially free of coloring agent additions (such as, but not limited to, conventional dyes) and have an absorption spectrum for visible radiation that does not vary significantly in response to actinic radiation. Further, with reference to substrates the term "tinted" means substrates that have a coloring agent addition (such as, but not limited to, conventional dyes) and an absorption spectrum for visible radiation that does not vary significantly in response to actinic radiation.

As used herein the term "linearly polarizing" with reference to substrates refers to substrates that are adapted to linearly polarize radiation (i.e., confine the vibrations of the electric vector of light waves to one direction). As used herein the term "circularly polarizing" with reference to substrates refers to substrates that are adapted to circularly polarize radiation. As used herein the term "elliptically polarizing" with reference to substrates refers to substrates that are adapted to elliptically polarize radiation. As used herein with the term "photochromic" with reference to substrates refers to substrates having an absorption spectrum for visible radiation that varies in response to at least actinic radiation and is thermally reversible. Further, as used herein with reference to substrates, the term "tinted-photochromic" means substrates containing a coloring agent addition as well as a photochromic compound, and having an absorption spectrum for visible radiation that varies in response to at least actinic radiation and is thermally reversible. Thus for example, in one non-limiting embodiment, the tinted-photochromic substrate can have a first color characteristic of the coloring agent and a second color characteristic of the combination of the coloring agent and the photochromic compound when exposed to actinic radiation.

One specific non-limiting embodiment provides an optical element comprising a substrate and an at least partial coating comprising at least one photochromic compound comprising (a) at least one photochromic group chosen from pyrans, oxazines, and fulgides; and (b) at least one lengthening agent L represented by Formula I and attached to the at least one photochromic group connected to at least a portion of the substrate. Further, according to this non-limiting embodiment, the at least one thermally reversible photochromic compound can be a photochromic-dichroic compound having an average absorption ratio greater than 2.3 in an activated state as determined according to CELL METHOD.

As discussed above, the optical elements according to various non-limiting embodiments disclosed herein can be display elements, such as, but not limited to screens, monitors, and security elements. For example, one non-limiting embodiment provides a display element comprising a first substrate having a first surface, a second substrate having a second surface, wherein the second surface of the second substrate is opposite and spaced apart from the first surface of the first substrate so as to define a gap; and a fluid material comprising at least one photochromic compound comprising (a) at least one photochromic group chosen from pyrans, oxazines, and fulgides; and (b) at least one lengthening agent L represented by Formula I and attached to the at least one photochromic group positioned within the gap defined by the first surface of the first substrate and the second surface of the second substrate. Further, the at least one photochromic compound can be a photochromic-dichroic compound having an average absorption ratio greater than 2.3 in an activated state as determined according to CELL METHOD.

Further, according to this non-limiting embodiment, the first and second substrates can be independently chosen from untinted substrates, tinted substrates, photochromic substrates, tinted-photochromic substrates, linearly polarizing substrates, circularly polarizing substrates, elliptically polarizing substrates and reflective substrates.

Another non-limiting embodiment provides a security element comprising a substrate and at least one photochromic compound comprising (a) at least one photochromic group chosen from pyrans, oxazines, and fulgides; and (b) at least one lengthening agent L represented by Formula I and attached to the at least one photochromic group connected to at least a portion of the substrate. Non-limiting examples of security elements include security marks and authentication marks that are connected to at least a portion of a substrate, such as and without limitation: access cards and passes, e.g., tickets, badges, identification or membership cards, debit cards etc.; negotiable instruments and non-negotiable instruments e.g., drafts, checks, bonds, notes, certificates of deposit, stock certificates, etc.; government documents, e.g., currency, licenses, identification cards, benefit cards, visas, passports, official certificates, deeds etc.; consumer goods, e.g., software, compact discs ("CDs"), digital-video discs ("DVDs"), appliances, consumer electronics, sporting goods, cars, etc.; credit cards; and merchandise tags, labels and packaging.

Although not limiting herein, according to this non-limiting embodiment, the security element can be connected to at least a portion of a substrate chosen from a transparent substrate and a reflective substrate. Alternatively, according to certain non-limiting embodiments wherein a reflective substrate is required, if the substrate is not reflective or sufficiently reflective for the intended application, a reflective material can be first applied to at least a portion of the substrate before the security mark is applied thereto. For example, a reflective aluminum coating can be applied to the at least a portion of the substrate prior to forming the security element thereon. Still further, security element can be connected to at least a portion of a substrate chosen from untinted substrates, tinted substrates, photochromic substrates, tinted-photochromic substrates, linearly polarizing, circularly polarizing substrates, and elliptically polarizing substrates.

Additionally, according to the aforementioned non-limiting embodiment the at least one photochromic compound can be a thermally reversible photochromic-dichroic compound having an average absorption ratio greater than 2.3 in the activated state as determined according to CELL METHOD.

Furthermore, security element according to the aforementioned non-limiting embodiment can further comprise one or more other coatings or sheets to form a multi-layer reflective security element with viewing angle dependent characteristics as described in U.S. Pat. No. 6,641,874, which is hereby specifically incorporated by reference herein.

The photochromic articles and optical elements described above can be formed by methods known in the art. Although not limiting herein, it is contemplated that the photochromic compounds disclosed herein can be connected to a substrate or host by incorporation into the host material or application onto the host or substrate, such as in the form of a coating.

For example, the photochromic-dichroic compound can be incorporated into an organic host material by dissolving or dispersing the photochromic compound within the host material, e.g., casting it in place by adding the photochromic compound to the monomeric host material prior to polymerization, imbibition of the photochromic compound into the host material by immersion of the host material in a hot solution of the photochromic compound or by thermal transfer. As used herein the term "imbibition" includes permeation of the photochromic compound alone into the host material, solvent assisted transfer of the photochromic compound into a porous polymer, vapor phase transfer, and other such transfer methods.

Additionally, the photochromic compound disclosed herein can be applied to the organic host material or other substrate as part of a coating composition (as discussed above) or a sheet comprising the photochromic compound. As used herein the term "coating" means a supported film derived from a flowable composition, which may or may not have a uniform thickness. As used herein the term "sheet" means a pre-formed film having a generally uniform thickness and capable of self-support.

Non-limiting methods of applying coating compositions comprising the photochromic compounds disclosed herein include those methods known in the art for applying coatings, such as, spin coating, spray coating, spray and spin coating, curtain coating, flow coating, dip coating, injection molding, casting, roll coating, wire coating, and overmolding. According to one non-limiting embodiment, a coating comprising the photochromic compound is applied to a mold and the substrate is formed on top of the coating (i.e., overmolding). Additionally or alternatively, a coating composition without the photochromic compound can be first applied to the substrate or organic host material using any of the aforementioned techniques and thereafter imbibed with the photochromic compound as described above.

Non-limiting methods of applying sheets comprising the photochromic compound disclosed herein to a substrate include, for example, at least one of: laminating, fusing, in-mold casting, and adhesively bonding the polymeric sheet to the at least a portion of the substrate. As used herein, the in-mold casting includes a variety of casting techniques, such as but not limited to: overmolding, wherein the sheet is placed in a mold and the substrate is formed (for example by casting) over at least a portion of the substrate; and injection molding, wherein the substrate is formed around the sheet. Further, it is contemplated that the photochromic compound can be applied to the sheet as a coating, incorporated into the sheet by imbibition or by other suitable methods, either prior to applying the sheet to the substrate or thereafter.

Moreover, as discussed above, the photochromic compounds disclosed herein can be incorporated or applied alone, or in combination with at least one other conventional organic photochromic compound, which can also be applied or incorporated into the host materials and substrates as described above.

EXAMPLES

Various embodiments disclosed herein will now be illustrated in the following non-limiting examples.

Example 1

Step 1

4-Fluorobenzophenone (64.5 g) and anhydrous dimethyl sulfoxide (DMSO) (200 ml) were added to a reaction flask under nitrogen. 1-phenylpiperazine (36.2 g) was added, and the suspension was heated to 180° C. After 2 hours, heat was removed, and the mixture was poured into 4 liters of water. The precipitate was collected by vacuum filtration, washed with water, dried in vacuum and recrystallized from acetone/methanol. GC/MS data showed that the resulting product (55 g, 89% yield), recovered as off-white crystals, has a structure consistent with 4-(4-phenylpiperazin-1-yl)benzophenone.

Step 2

4-(4-phenylpiperazin-1-yl)benzophenone (55 g) from Step 1 and dimethylformamide (DMF) (300 mL, saturated with acetylene) were added to a reaction flask. A sodium acetylide suspension (64 g of a 18 weight percent slurry in toluene, obtained from Aldrich) was added to the mixture with stirring. After 20 minutes, the reaction was poured into a stirred mixture of deionized water (3 L) and hexanes (500 ml). The solid formed was collected by vacuum filtration and dried in vacuum. An NMR spectrum showed that the final product (59 g, 99.7% yield), an off-white powder, had a structure consistent with 1-phenyl-1-(4-phenylpiperazin-1-yl)phenyl)-prop-2-yn-1-ol.

Step 3

N-Phenylpiperazine (31.3 g, 187 millimole (mmol)), 2,3-dimethoxy-7,7-dimethyl-7H-benzo[c]fluoren-5-ol (40 g, 125 mmol) and THF (200 mL) were added to a 2 liter round-bottomed flask equipped with a bubbler and magnetically stirred at room temperature. A solution of 1.6 M methyl lithium in ethyl ether (234 mL, 375 mmol) was added to the mixture slowly via a dropping funnel under a nitrogen atmosphere. Gas evolution and boiling of the solvent was observed and 200 mL of the solvent was removed from the flask by distillation. The remaining mixture was refluxed for 10 hours and then poured into 400 mL water. Hydrochloric acid (HCl) (3 N) was added to the mixture with stirring until a pH value of 4-6 was obtained. Ethyl acetate (300 mL) was then added to the mixture. The crystalline precipitate was collected by vacuum filtration. The organic layer was separated, dried and concentrated. The resulting oil was crystallized by the addition of ethyl acetate and collected by vacuum filtration. The recovered solids were combined and washed with acetone. White crystals (45.7 g) were obtained as the product. The product was characterized by NMR and MS to have a structure consistent with 7,7-dimethyl-2-(4-phenylpiperazin-1-yl)-3-methoxy-7H-benzo[c]fluoren-5-ol.

Step 4

1-phenyl-1-(4-phenylpiperazin-1-yl)phenyl)-prop-2-yn-1-ol (1.84 g, 5 mmol) from step 2,7,7-dimethyl-2-(4-phenylpiperazin-1-yl)-3-methoxy-7H-benzo[c]fluoren-5-ol from Step 3 (1.5 g, 3.33 mmol), 3 Å molecular sieves (2 g) and chloroform (80 mL) were added to a 250 mL flask equipped with a dropping funnel and stirred at room temperature. A chloroform solution of trifluoroacetic acid (0.3 M, 4 mL) was added dropwise to the reaction flask via the dropping funnel. A gray color was obtained. The resulting reaction mixture was refluxed for 8 hours. Molecular sieves were removed by filtration over a pad of Celite. The chloroform solution was washed with a saturated sodium bicarbonate water solution, dried over magnesium sulfate and concentrated. The recovered product was purified by flash chromatography on silica gel (eluent: 20/80 ethyl acetate/hexanes). The recovered solid was further purified by dissolution in CHCl$_3$ and precipitation from methanol to yield a gray solid (2.1 g). The final product was identified by NMR as having a structure consistent with 3-phenyl-3-(4-pyrrolidin-1-yl-phenyl)-13,13-dimethyl-6-methoxy-7-(4-phenyl-piperazin-1-yl)indeno[2',3':3,4]naphtho[1,2-b]pyran.

Example 2

The procedures of Step 1, Step 2 and Step 4 of Example 1 were followed except that in Step 1,4-piperidinopiperidine was used in place of 1-phenylpiperazine and in Step 4,7,7-dimethyl-7H-benzo[c]fluoren-5-ol was used in place of 7,7-dimethyl-2-(4-phenylpiperazin-1-yl)-3-methoxy-7H-benzo[c]fluoren-5-ol. The recovered final product was a blue solid. An NMR spectrum showed that the final product had a structure consistent with 3-phenyl-3-(4-(4-piperidinopiperidino)phenyl)-13,13-dimethyl-indeno[2',3':3,4]naphtho[1,2-b]pyran.

Example 3

Step 1

2,3-Dimethoxy-5-hydroxy-7H-benzo[C]fluoren-7-one, the product of Step 5 of Example 14 of U.S. Pat. No. 6,296,785 (50.13 g, 0.164 mol) and THF (500 ml) were added to a flask equipped with a bubbler under a nitrogen atmosphere and stirred at room temperature. A solution of 25 weight percent ethylmagnesium chloride in THF (124 ml, 0.36 mol) was added slowly and carefully causing the evolution of gas. The addition was completed in 30 minutes. The reaction was exothermic and caused the THF to boil. After 10 minutes, a water solution of 3 N HCl was added slowly with vigorous stirring until a slightly acidic mixture was obtained. A saturated sodium bicarbonate water solution was added. The organic layer was separated and the water layer was extracted with ethyl acetate. The recovered organic solutions were combined, dried over magnesium sulfate and concentrated. Crystals precipitated during the evaporation of the solvent. Chloroform was added to help with crystallization. The product was collected by vacuum filtration as white crystals (47.7 g). An NMR spectrum showed the product to have a structure consistent with 7-ethyl-2,3-dimethoxy-7H-benzo[c]fluorene-5,7-diol.

Step 2

N-Phenylpiperazine (7.23 g, 44.6 mmol), 7-ethyl-2,3-dimethoxy-7H-benzo[c]fluoren-5,7-diol (10 g, 30 mmol) from Step 1 and THF (200 mL) were added to a flask and magnetically stirred at room temperature under a nitrogen atmosphere. A solution of 1.6 M methyl lithium in ethyl ether (93 mL, 149 mmol) was added to the mixture slowly via a dropping funnel. A 100 mL amount of the solvents was distilled out of the flask. The remaining mixture was refluxed for 2 days. The resulting reaction mixture was poured into a flask containing water (200 mL), acidified to pH 4 by the addition of 3 N HCl. Ethyl acetate (100 mL) was added to the mixture and the resulting crystalline precipitate was collected by vacuum filtration, washed with water and acetone and air-dried. White crystals (6.77 g) were recovered as the product. An NMR spectrum showed that the resulting product had a structure consistent with 7-ethyl-3-methoxy-2-(4-phenyl-piperazin-1-yl)-7H-benzo[c]fluoren-5,7-diol.

Step 3

The procedure of Step 4 of Example 1 was followed except that 1-phenyl-1-(4-(4-hydroxypiperidin-1-yl)-phenyl)-prop-2-yn-1-ol from Example 6 was used in place of 1-phenyl-1-(4-phenylpiperazin-1-yl)phenyl)-prop-2-yn-1-ol and 7-ethyl-3-methoxy-2-(4-phenyl-piperazin-1-yl)-7H-benzo[c]fluorene-5,7-diol was used in place of 7,7-dimethyl-2-(4-phenylpiperazin-1-yl)-3-methoxy-7H-benzo[c]fluoren-5-ol. An NMR spectrum showed that the resulting product, a black solid, had a structure consistent with 3-phenyl-3-(4-(4-hydroxypiperadin-1-yl)phenyl)-13-hydroxy-13-ethyl-6-methoxy-7-(4-phenyl-piperazin-1-yl)-indeno[2',3':3,4]naphtho[1,2-b]pyran.

Step 4

The product of Step 3 (0.5 g, 0.66 mmol), 4-hexylbenzoyl-chloride (0.42 g, 1.9 mmol) and pyridine (10 mL) were added to a reaction flask and stirred at room temperature for 4 hours. The resulting mixture was poured into a beaker containing 100 mL of water. The resulting precipitate was dissolved in chloroform, dried over magnesium sulfate, concentrated and flash-chromatographed from silica gel using as an eluent: 2/8 (volume/volume) ethyl acetate/hexanes. The recovered solid was further purified by dissolution in CHCl$_3$ and precipitation from methanol to yield a black solid (0.44 g). An NMR spectrum showed that the final product had a structure consistent with 3-phenyl-3-(4-(4-(4-hexylbenzoyloxy)-piperadin-1-yl)phenyl)-13-hydroxy-13-ethyl-6-methoxy-7-(4-phenyl-piperazin-1-yl)-indeno[2',3':3,4]naphtho[1,2-b]pyran.

Example 4

Step 1

The procedure of Example 1 was followed except that in Step 1, pyrrolidine was used in place of 1-phenylpiperazine and in Step 3, 4-hydroxypiperidine was used in place of 1-phenylpiperazine. An NMR spectrum showed that the final product, recovered as purple crystals, had a structure consistent with 3-phenyl-3-(4-(pyrrolidin-1-yl)-phenyl)-13,13-dimethyl-6-methoxy-7-(4-hydroxypiperadin-1-yl)indeno[2',3':3,4]naphtho[1,2-b]pyran.

Step 2

3-phenyl-3-(4-(pyrrolidin-1-yl)-phenyl)-13,13-dimethyl-6-methoxy-7-(4-hydroxypiperadin-1-yl)indeno[2',3':3,4]naphtho[1,2-b]pyran from Step 1 (1.5 g, 2.3 mmol), 4,4'-biphenyldicarboxylic acid (0.27 g, 1.1 mmol), dicyclohexyl carbodiimide (0.48 g, 2.3 mmol), 4-(dimethylamino)-pyridine (0.03 g, 0.23 mmol) and dichloromethane (40 mL) were added to a flask and heated under reflux for 36 hours. The solid produced was removed by filtration and the remaining solution was concentrated. The resulting solid crude product was purified by flash chromatography (3/7 ethyl acetate/hexanes, volume ratio). The recovered solid was further purified by dissolution in CHCl$_3$ and precipitation from methanol. An NMR spectrum showed that the final product, a purple solid (0.47 g), had a structure consistent with Biphenyl-4,4'-dicarboxylic acid bis-{1-[6-methoxy-13,13-dimethyl-3-phenyl-3-(4-pyrrolidin-1-yl-phenyl)-3H,13H-indeno[2',3':3,4]naphtha[1,2-b]pyran-7-yl]-piperidin-4-yl}ester.

Example 5

Step 1

The procedure of Step 1, Step 2 and Step 3 of Example 7 was followed except that 4-hydroxypiperidine was used in place of N-phenylpiperazine in Step 2 and 1-phenyl-1-(4-pyrrolidin-1-yl-phenyl)-prop-2-yn-1-ol (one intermediate from Step 1 of Example 4) was used in place of 1-phenyl-1-(4-(4-hydroxypiperidin-1-yl)-phenyl)-prop-2-yn-1-ol in Step 3. An NMR spectrum showed that the final product, a purple solid, had a structure consistent with 3-phenyl-3-(4-pyrrolidinophenyl)-13-hydroxy-13-ethyl-6-methoxy-7-(4-hydroxypiperadin-1-yl)-indeno[2',3':3,4]naphtho[1,2-b]pyran.

Step 2

A mixture of 3-phenyl-3-(4-pyrrolidinophenyl)-13-hydroxy-13-ethyl-6-methoxy-7-(4-hydroxypiperadin-1-yl)-indeno[2',3':3,4]naphtho[1,2-b]pyran from Step 1 (4.0 g, 6 mmol) and tetrahydrofuran (THF) (200 mL) was added to a reaction flask and stirred at room temperature under a nitrogen atmosphere. A 2 M solution of lithium diisopropyl amide in a mixture of THF and hexanes solvents available from ACROS Organics (12 mL, 24 mmol) was added via a syringe. Cholesteryl chloroformate (2.7 g, 6 mmol) was added at −78° C. and the resulting mixture was warmed up to room temperature and stirred for half an hour at room temperature. The reaction mixture was poured into water (1500 mL), acidified with 3 N HCl followed by neutralization of the excess acid by saturated sodium bicarbonate water solution, extracted with ethyl acetate, dried over magnesium sulfate, concentrated and flash chromatographed using 3:7 (volume:volume) ethyl acetate:hexanes as the eluent. Two products were obtained, which correspond to mono-adduct and di-adduct respectively. An NMR showed that the di-adduct product (0.666 g) had a structure consistent with 3-phenyl-3-{4-(pyrrolidin-1-yl)phenyl)-13-{17-(1,5-dimethyl-hexyl)-10,13-dimethyl-2,3,4,7,8,9,10,11,12,13,14,15,16,17-tetradecahydro-1H-cyclopenta[a]phenanthren-3-yloxy}-13-ethyl-6-methoxy-7-(4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperadin-1-yl)-indeno[2',3':3,4]naphtho[1,2-b]pyran.

Example 6

The procedure of Example 3 was followed except that 4-hydroxypiperidine was used in place of N-phenylpiperazine in Step 2 and cholesteryl chloroformate was used in place of hexylbenzoylchloride in Step 4. An NMR spectrum showed that the resulting product, an off-white solid, had a structure consistent with 3-phenyl-3-(4-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl}-phenyl)-13-ethyl-13-hydroxy-6-methoxy-7-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl}-)indeno[2',3':3,4]naphtho[1,2-b]pyran.

Example 7

Step 1

4-Hydroxybenzoic acid (45 g, 0.326 mol), dodecylbenzenesulfonic acid (2 drops) and ethyl ether (500 mL) were added to a flask equipped with a dropping funnel and stirred at room temperature. Neat dihydropyran (DHP)(35 mL, 0.39 mol) was added dropwise via the dropping funnel within a 30 minute interval and a white crystalline precipitate formed. The resulting suspension was stirred overnight and the precipitate was collected by vacuum filtration. A white solid product (41 g) was recovered. An NMR spectrum showed that the resulting product had a structure consistent with 4-(2-tetrahydro-2H-pyranoxy)benzoic acid.

Step 2

4-Hydroxypiperidine (19.5 g, 0.193 mol), 2,3-dimethoxy-7,7-dimethyl-7H-benzo[c]fluoren-5-ol (41.17 g, 0.128 mol) and THF (300 mL) were added to a 2 liter round-bottomed flask equipped with a bubbler and stirred magnetically at room temperature. A solution of 3 M methyl Grignard in THF (171 mL, 0.514 mmol) was added to the mixture slowly via a dropping funnel under a nitrogen atmosphere. The resulting mixture was concentrated to a viscous oil. The viscous oil was maintained under reflux and stirred for 5 days. Thin layer chromatography showed that 2 products were present in the reaction. The resulting reaction mixture was poured into a beaker containing water (1000 mL), neutralized with HCl (3 N) to a pH value of 4-6, extracted with ethyl acetate and flash-chromatographed using 2:8 (volume:volume) ethyl acetate:hexanes as the eluent. Both products were collected and obtained as white solids. An NMR spectrum showed that the major product had a structure consistent with 7,7-dimethyl-3-methoxy-7H-benzo[c]fluorene-2,5-diol and the minor product had a structure consistent with 7,7-dimethyl-3-methoxy-3-(4-hydroxypiperadin-1-yl)-7H-benzo[c]fluorene-5-ol.

Step 3

7,7-Dimethyl-3-methoxy-7H-benzo[c]fluorene-2,5-diol from Step 1 (5.1 g), 1-phenyl-1-(4-pyrrolidin-1-yl-phenyl)-prop-2-yn-1-ol (5.1 g), pyridinium p-toluenesulfonate (0.2 g), trimethyl orthoformate (4 g) and chloroform (100 mL) were added to a reaction flask and stirred at room temperature over the weekend. The reaction mixture was then concentrated and flash-chromatographed using 2:8 (volume:volume) ethyl acetate:hexanes as the eluent. A grey solid was recovered (9.1 g). An NMR spectrum showed that the resulting product had a structure consistent with 3-phenyl-3-(4-(4-pyrrolidinylphenyl)-13,13-dimethyl-6-methoxy-7-hydroxy-indeno[2',3':3,4]naphtho[1,2-b]pyran.

Step 4

The procedure of Step 2 of Example 4 was used except that the reaction was conducted at room temperature, 4-(2-tetrahydro-2H-pyranoxy)benzoic acid from Step 1 was used in place of 4,4'-biphenyldicarboxylic acid, 3-phenyl-3-(4-(4-pyrrolidinylphenyl)-13,13-dimethyl-6-methoxy-7-hydroxy-indeno[2',3':3,4]naphtho[1,2-b]pyran from Step 3 was used in place of 3-phenyl-3-(4-(pyrrolidin-1-yl)-phenyl)-13,13-dimethyl-6-methoxy-7-(4-hydroxypiperadin-1-yl)indeno[2',3':3,4]naphtho[1,2-b]pyran and flash chromatography on silica gel was not used for the product purification. The product was purified by a technique of dissolution in chloroform followed by precipitation from methanol. An NMR spectrum showed that the resulting product, a blue solid, had a structure consistent with 3-phenyl-3-(4-(pyrrolidin-1-yl)phenyl)-13,13-dimethyl-6-methoxy-7-(4-(2-tetrahydro-2H-pyranoxy)benzoyloxy)-indeno[2',3':3,4]naphtho[1,2-b]pyran.

Step 5

3-phenyl-3-(4-(pyrrolidin-1-yl)phenyl)-13,13-dimethyl-6-methoxy-7-(4-(2-tetrahydro-2H-pyranoxy)benzoyloxy)-indeno[2',3':3,4]naphtho[1,2-b]pyran, product of Step 4 (5 g, 6.5 mmol), pyridinium p-toluenesulfonate (0.16 g, 0.65 mmol), ethyl acetate (100 mL) and methanol (20 mL) were added to a reaction flask and refluxed for 24 hours. The resulting reaction mixture was extracted with water, dried over magnesium sulfate, concentrated and flash-chromatographed using 3/7 (volume/volume) ethyl acetate/hexane as the eluent. An NMR spectrum showed that the resulting product, a blue solid (4.4 g), had a structure consistent with 3-phenyl-3-(4-(pyrrolidin-1-yl)phenyl)-13,13-dimethyl-6-methoxy-7-(4-hydroxybenzoyloxy)-indeno[2',3':3,4]naphtho[1,2-b]pyran.

Step 6

The procedure of Step 4 and Step 5 of this example was used except that the product from Step 5 of this Example, 3-phenyl-3-(4-(pyrrolidin-1-yl)phenyl)-13,13-dimethyl-6-methoxy-7-(4-hydroxybenzoyloxy)-indeno[2',3':3,4]naphtho[1,2-b]pyran, was used in place of 3-phenyl-3-(4-(4-pyrrolidinylphenyl)-13,13-dimethyl-6-methoxy-7-hydroxy-indeno[2',3':3,4]naphtho[1,2-b]pyran. An NMR spectrum showed that the resulting product, a blue solid, had a structure consistent with 3-phenyl-3-(4-(pyrrolidin-1-yl)phenyl)-13,13-dimethyl-6-methoxy-7-(4-(4-hydroxybenzoyloxy)benzoyloxy)-indeno[2',3':3,4]naphtho[1,2-b]pyran.

Step 7

The procedure of Step 4 and Step 5 of this Example was used except that the product from Step 6 of this Example, 3-phenyl-3-(4-(pyrrolidin-1-yl)phenyl)-13,13-dimethyl-6-methoxy-7-(4-(4-hydroxybenzoyloxy)benzoyloxy)-indeno[2',3':3,4]naphtho[1,2-b]pyran, was used in place of 3-phenyl-3-(4-(4-pyrrolidinylphenyl)-13,13-dimethyl-6-methoxy-7-hydroxy-indeno[2',3':3,4]naphtho[1,2-b]pyran. An NMR spectrum showed that the resulting product, a blue solid, had a structure consistent with 3-phenyl-3-(4-(pyrrolidin-1-yl)phenyl)-13,13-dimethyl-6-methoxy-7-(4-(4-(4-hydroxybenzoyloxy)benzoyloxy)benzoyloxy)-indeno[2',3':3,4]naphtho[1,2-b]pyran.

Step 8

The procedure of Step 4 of Example 3 was used except that the product from Step 7,3-phenyl-3-(4-(pyrrolidin-1-yl)phenyl)-13,13-dimethyl-6-methoxy-7-(4-(4-(4-hydroxybenzoyloxy)benzoyloxy)benzoyloxy)-indeno[2',3':3,4]naphtho[1,2-b]pyran, was used in place of 3-phenyl-3-(4-(4-hydroxypiperadin-1-yl)phenyl)-13-hydroxy-13-ethyl-6-methoxy-7-(4-phenyl-piperazin-1-yl)-indeno[2',3':3,4]naphtho[1,2-b]pyran. An NMR spectrum showed that the final product, a blue solid, had a structure consistent with 3-phenyl-3-(4-(pyrrolidin-1-yl)phenyl)-13,13-dimethyl-6-methoxy-7-(4-(4-(4-(4-hexylbenzoyloxy)benzoyloxy)benzoyloxy)benzoyloxy)-indeno[2',3':3,4]naphtho[1,2-b]pyran.

Example 8

The procedure of Step 3 of Example 7 was used except that methyl 6-methoxy-1-naphthoate was used in place of 7,7-Dimethyl-3-methoxy-7H-benzo[c]fluorene-2,5-diol and 1-phenyl-1-(4-(4-(4-methoxyphenyl)piperazino)phenyl)-2-propyn-1-ol was used in place of 1-phenyl-1-(4-pyrrolidin-1-yl-phenyl)-prop-2-yn-1-ol. Light yellow crystals (2.4 g) were recovered. An NMR spectrum showed that the resulting product had a structure consistent with 3-(4-(4-(4-methoxy-phenyl)-piperazin-1-yl)-phenyl)-3-phenyl-7-methoxycarbonyl-3H-naphtho[2,1-b]pyran.

Example 9

Step 1

The procedure of Example 8 was followed except that 6-hydroxy-1-naphthoic acid was used in place of methyl 6-methoxy-1-naphthoate. A light orange color powder was recovered. An NMR spectrum showed that the resulting product had a structure consistent with 3-(4-(4-(4-methoxy-phenyl)-piperazin-1-yl)-phenyl)-3-phenyl-7-hydroxycarbonyl-3H-naphtho[2,1-b]pyran.

Step 2

The procedure of Step 2 of Example 4 was used except that the reaction was conducted at room temperature, 3-{4-[4-(4-Methoxy-phenyl)-piperazin-1-yl]-phenyl}-3-phenyl-7-hydroxycarbonyl-3H-naphtho[2,1-b]pyran was used in place of 4,4'-biphenyldicarboxylic acid and 4-phenylphenol was used in place of 3-phenyl-3-(4-(pyrrolidin-1-yl)-phenyl)-13,13-dimethyl-6-methoxy-7-(4-hydroxypiperadin-1-yl)indeno[2',3':3,4]naphtho[1,2-b]pyran. An NMR spectrum showed that the white solid product had a structure consistent with 3-{4-[4-(4-Methoxy-phenyl)-piperazin-1-yl]-phenyl}-3-phenyl-7-(4-phenyl-(phen-1-oxy)carbonyl)-3H-naphtho[2,1-b]pyran.

Example 10

The procedure of Step 3 of Example 7 was used except that 4-hydroxy-dibenzofuran was used in place of 7,7-Dimethyl-3-methoxy-7H-benzo[c]fluorene-2,5-diol and 1-phenyl-1-(4-(4-(4-methoxyphenyl)piperazino)phenyl)-2-propyn-1-ol was used in place of 1-phenyl-1-(4-pyrrolidin-1-yl-phenyl)-prop-2-yn-1-ol. An NMR spectrum showed that the final product, an off-white solid, had a structure consistent with 2-phenyl-2-{4-[4-(4-methoxy-phenyl)-piperazin-1-yl]-phenyl}-benzofuro[3',2':7,8]benzo[b]pyran.

Example 11

Step 1

The procedure of Step 3 of Example 7 was used except that methyl 2,4-dihydroxybenzoate was used in place of 7,7-Dimethyl-3-methoxy-7H-benzo[c]fluorene-2,5-diol. An NMR spectrum showed that the final product, a yellow solid, had a structure consistent with 7-hydroxy-2-phenyl-2-(4-pyrrolidin-1-yl-phenyl)-6-methoxycarbonyl-2H-benzo[b]pyran.

Step 2

The procedure of Step 4 of Example 3 was followed except that the product from Step 1, 7-hydroxy-2-phenyl-2-(4-pyrrolidin-1-yl-phenyl)-6-methoxycarbonyl-2H-benzo[b]pyran was used in place of 3-phenyl-3-(4-(4-hydroxypiperadin-1-yl)phenyl)-13-hydroxy-13-ethyl-6-methoxy-7-(4-phenyl-piperazin-1-yl)-indeno[2',3':3,4]naphtho[1,2-b]pyran and cholesteryl chloroformate was used in place of 4-hexylbenzoylchloride. An NMR spectrum showed that the final product, an off-white solid, had a structure consistent with 7-{17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy}-2-phenyl-2-(4-pyrrolidin-1-yl-phenyl)-6-methoxycarbonyl-2H-benzo[b]pyran.

Example 12

The procedure of Step 3 of Example 7 was used except that methyl 3,5-dihydroxy-2-naphthoate was used in place of 7,7-Dimethyl-3-methoxy-7H-benzo[c]fluorene-2,5-diol and 1-phenyl-1-(4-(4-(4-methoxyphenyl)piperazino)phenyl)-2-propyn-1-ol was used in place of 1-phenyl-1-(4-pyrrolidin-1-yl-phenyl)-prop-2-yn-1-ol. An NMR spectrum showed that the final product, a grey solid, had a structure consistent with 2-phenyl-2-{4-[4-(4-methoxy-phenyl)-piperazin-1-yl]-phenyl}-9-hydroxy-8-methxycarbonyl-2H-naphtho[1,2-b]pyran.

Example 13

To a stirred mixture of 4-n-butylaniline (1.13 g, 7.6 mmol) and THF (20 ml) at room temperature, isopropylmagnesium bromide (2 M in ethyl ether, 3.8 ml) was added via a syringe. After 2 minutes, solid 2-phenyl-2-{4-[4-(4-Methoxy-phenyl)-piperazin-1-yl]-phenyl}-9-hydroxy-8-methxycarbonyl-2H-naphtho[1,2-b]pyran was added in one portion and the mixture obtained was kept stirring at room temperature for four more hours and then poured into water. The precipitate was collected, dissolved in chloroform, dried over magnesium sulfate and concentrated. The crude product was purified by flash chromatography. An NMR spectrum showed that the final product, a grey solid (0.71 g), had a structure consistent with 2-phenyl-2-{4-[4-(4-Methoxy-phenyl)-piperazin-1-yl]-phenyl}-9-hydroxy-8-(4-butyl-phenyl)carbamoyl-2H-naphtho[1,2-b]pyran.

Example 14

A mixture of 1-nitroso-2-naphthol (12.32 g, 71 mmol), ethyl isonipecotate (11.2 g, 71 mmol) and methanol (200 ml) was refluxed for 2 hours. Neat 1,3,3-trimethyl-2-methyl-eneindoline was added in one portion. The mixture was kept refluxing for 10 more minutes and then the solvent was removed by vacuum. Flash chromatography was used to separate the product. An NMR spectrum showed that the final product, a yellow solid (9 g, yield 25%). had a structure consistent with 1,3,3-trimethyl-6'-(4-ethoxycarbonyl)-piperidin-1-yl)-spiro[indoline-2,3'-3H-naphtho[2,1-b][1,4]oxazine].

Example 15

The procedure of Example 13 was used except that 1,3,3-trimethyl-6'-(4-ethoxycarbonyl)-piperidin-1-yl)-spiro[indoline-2,3'-3H-naphtho[2,1-b][1,4]oxazine] was used in place of 2-phenyl-2-{4-[4-(4-Methoxy-phenyl)-piperazin-1-yl]-phenyl}-9-hydroxy-8-methoxycarbonyl-2H-naphtho[1,2-b] pyran. An NMR spectrum showed that the final product, off-white crystals, had a structure consistent with 1,3,3-trimethyl-6'-(4-[N-(4-butylphenyl)carbamoyl]-piperidin-1-yl)-spiro[indoline-2,3'-3H-naphtho[2,1-b][1,4]oxazine].

Example 16

The procedure of Example 14 was used except that N-(4-methoxyphenyl)piperazine was used in place of ethyl isonipecotate. An NMR spectrum showed that the final product had a structure consistent with 1,3,3-trimethyl-6'-(4-(4-methoxyphenyl)piperazin-1-yl)-spiro[indoline-2,3'-3H-naphtho[2,1-b][1,4]oxazine].

Example 17

The procedure of Example 14 was used except that N-(4-hydroxyphenyl)piperazine was used in place of ethyl isonipecotate. An NMR spectrum showed that the final product had a structure consistent with 1,3,3-trimethyl-6'-(4-(4-hydroxyphenyl)piperazin-1-yl)-spiro[indoline-2,3'-3H-naphtho[2,1-b][1,4]oxazine].

Example 18

Part A
Testing was done with the photochromic compounds described in Examples 1-17 in the following manner. A quantity of photochromic compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis (2-methyl propionitrile) (AIBN). Each photochromic compound was dissolved into the monomer blend by stirring and gentle heating, if necessary. After a clear solution was obtained, it was poured into a flat sheet mold having an interior dimension of 2.2 mm+/−0.3 mm×6 inch (15.24 cm)×6 inch (15.24 cm). The mold was sealed and placed in a horizontal airflow, programmable oven to ramp from 40° C. to 95° C. over a 5 hour interval, hold the temperature at 95° C. for 3 hours, ramp down to 60° C. over a 2 hour interval and then hold at 60° C. for 16 hours. After curing, the mold was opened, and the polymer sheet was cut into 2 inch (5.1 cm) test squares using a diamond blade saw.

Part B
Prior to response testing on an optical bench, the photochromic samples from Part A were conditioned by exposing them to 365 nm ultraviolet light for 10 minutes at a distance of about 14 cm from the source in order to pre-activate the photochromic molecules. The UVA irradiance at the sample was measured with a Licor Model Li-1800 spectroradiometer and found to be 22.2 Watts per square meter. The samples were then placed under a halogen lamp (500 W, 120V) for about 10 minutes at a distance of about 36 cm from the lamp in order to bleach, or inactivate, the photochromic compound in the samples. The illuminance at the sample was measured with the Licor spectroradiometer and found to be 21.9 Klux. The samples were then kept in a dark environment for at least 1 hour prior to testing in order to cool and continue to fade back to a ground state.

The optical bench was fitted with an Oriel Model #66011 300-watt Xenon arc lamp, an Oriel Model 71445 computer controlled shutter, a Schott 3 mm KG-2 band-pass filter, which removed short wavelength radiation, neutral density filter(s) to attenuate light from the xenon lamp, a fused silica condensing lens for beam collimation, and a fused silica water cell/sample holder for maintaining sample temperature in which the test sample to be tested was inserted. The temperature in the water cell was controlled with a pumped water circulation system in which the water passed through copper coils that were placed in the reservoir of a chiller unit. The water cell used to hold test samples contained fused silica sheets on the front and back facings in order to eliminate spectral change of the activation or monitoring light beams. The filtered water passing through the water cell was maintained at 72° F.±2° for photochromic response testing. An Oriel Photofeedback unit, Model 68850 was used to control the intensity of the xenon arc lamp during activation of the sample.

An Ocean Optics LS-1 tungsten halogen light source was used as the monitoring light source for photochromic response measurement. Light, focused into a fiber optic cable was collimated and passed perpendicularly through the center of the sample, in the water cell. After passing through the sample, the light was refocused into a 2-inch integrating sphere and fed to an Ocean Optics S2000 spectrophotometer by fiber optic cables. Ocean Optics OOIBase 32 software and PPG proprietary software were used to measure response and control the operation of the optical bench.

Irradiance for response testing of the photochromic samples on the optical bench was established at the sample using an International Light Research Radiometer, Model IL-1700 with a detector system comprising a Model SED033 detector, B Filter and diffuser. The output display of the radiometer was corrected (factor values set) against a Licor 1800-02 Optical Calibration Calibrator in order to display values representing Watts per square meter UVA. The irradiance at the sample point for initial response testing was set at to 3.0 Watts per square meter UVA and approximately 8.6 Klux illuminance. During sample response testing, if a sample darkened beyond an acceptable detection capability limit, the irradiance was lowered to 1.0 Watts per square meter UVA or the sample was remade at a one-half concentration in the copolymer. Adjusting the output of the filtered xenon arc lamp was accomplished by increasing or decreasing the current to the lamp through the controller and/or by adding or removing neutral density filters in the light path. The test samples were exposed to the activation light at 30°-35° normal to its surface while being perpendicular to the monitoring light.

Samples were activated in the 72° F. controlled water cell for 30 minutes, then allowed to fade under room light conditions until the change in optical density of the activated sample faded to ¼ of its highest dark (saturated) state or for a maximum of 30 minutes of fade.

Change in optical density (ΔOD) from the bleached state to the darkened state was determined by establishing the initial transmittance, opening the shutter from the Xenon lamp to provide ultraviolet radiation to change the test lens from the bleached state to an activated (i.e., darkened) state. Data was collected at selected intervals of time, measuring the transmittance in the activated state, and calculating the change in optical density according to the formula: ΔOD=log(% Tb/% Ta), where % Tb is the percent transmittance in the bleached state, % Ta is the percent transmittance in the activated state and the logarithm is to the base 10.

The $\lambda_{max-vis}$ in the visible light range is the wavelength in the visible spectrum at which the maximum absorption of the activated form of the photochromic compound occurs. The $\lambda_{max-vis}$ was determined by testing the photochromic test square in a Varian Cary 3 UV-Visible spectrophotometer or comparable equipment.

Some of the compounds of the Examples exhibited dual absorption peaks in the visible spectrum in distinct color regions. For each $\lambda_{max-vis}$ the corresponding sensitivity (Δ OD/Min), saturation optical density (Δ OD at saturation) and fade half life (T ½) for the compounds of the Examples are tabulated in Table II for Band A representing the major (more intense) absorption peak and B and B representing the minor absorption peak.

The ΔOD/Min, which represents the sensitivity of the photochromic compound's response to UV light, was measured over the first five (5) seconds of UV exposure, then expressed on a per minute basis. The saturation optical density (ΔOD at saturation) was taken under identical conditions except UV exposure was continued for a total of 30 minutes. The fade half life is the time interval in seconds for the ΔOD of the activated form of the photochromic compound in the test squares to reach one half the ΔOD measured after fifteen minutes, or after saturation or near-saturation was achieved, at room temperature after removal of the source of activating light, e.g., by closing the shutter.

TABLE II

| Example | Band | $\lambda_{max-vis}$ (nm) | Sensitivity (ΔOD/min) | ΔOD @ Saturation | T ½ (seconds) |
|---|---|---|---|---|---|
| Example 1 | A | 502 | 0.51 | 1.62 | 701 |
| | B | 589 | 0.35 | 1.15 | 716 |
| Example 2 | A | — | — | — | — |
| | B | 592 | 0.68 | 1.32 | 219 |
| Example 3 | A | 507 | 0.46 | 0.71 | 154 |
| | B | 597 | 0.34 | 0.54 | 154 |
| Example 4 | A | 522 | 0.16 | 0.66 | 426 |
| | B | 620 | 0.16 | 0.66 | 430 |
| Example 5 | A | 528 | 0.1 | 0.22 | 219 |
| | B | 624 | 0.1 | 0.23 | 208 |
| Example 6 | A | 503 | 0.49 | 0.80 | 155 |
| | B | 601 | 0.36 | 0.58 | 159 |

TABLE II-continued

| Example | Band | $\lambda_{max-vis}$ (nm) | Sensitivity (ΔOD/min) | ΔOD @ Saturation | T ½ (seconds) |
|---|---|---|---|---|---|
| Example 7 | A | 498 | 0.19 | 0.39 | 221 |
| | B | 631 | 0.37 | 0.74 | 210 |
| Example 8* | | — | — | — | — |
| | | — | — | — | — |
| Example 9* | | — | — | — | — |
| | | — | — | — | — |
| Example 10 | A | 511 | 0.03 | 0.03 | >2000 |
| | B | 573 | 0.03 | 0.03 | >2000 |
| Example 11* | | — | — | — | — |
| | | — | — | — | — |
| Example 12 | A | 565 | 0.12 | 0.54 | 1022 |
| | B | | | | |
| Example 13 | A | 560 | 0.05 | 0.29 | 1329 |
| | B | | | | |
| Example 14 | A | 437 | 0.06 | 0.02 | 17 |
| | B | 585 | 0.41 | 0.17 | 19 |
| Example 15 | A | 437 | 0.05 | 0.02 | 17 |
| | B | 584 | 0.36 | 0.16 | 20 |
| Example 16 | A | 585 | 0.36 | 0.16 | 21 |
| | B | 432 | 0.02 | 0.02 | 26 |
| Example 17 | A | 579 | 0.35 | 0.16 | 22 |
| | B | | | | |

*Fade rate too fast to permit measurement.

Example 19

The average absorption ratio of each of the photochromic compounds of Examples 1-17, as well as the average absorption ratio of Photosol™ 0265 ("Comparative Example"), which is commercially available from PPG Industries, Inc. and reported to be 1,3,3,4,5 (or 1,3,3,5,6)-pentamethyl-spiro [indoline-2,3-[3H]naphth[2,1-b][1,4]oxazine, was determined according to the CELL METHOD.

A cell assembly having the following configuration was obtained from Design Concepts, Inc. Each of the cell assemblies was formed from two opposing glass substrates that are spaced apart with a glass bead spacer having a diameter of 20 microns+/−1 micron. The inner surfaces of each of the glass substrates had oriented polyimide coating thereon to provide for the alignment of a liquid crystal material as discussed below. Two opposing edges of the glass substrates were sealed with an epoxy sealant, leaving the remaining two edges open for filling.

The gap between the two glass substrates of the cell assembly was filled with a liquid crystal solution containing the one of the photochromic compounds of Examples 1-17 or the Comparative Example ("Test Material"). The liquid crystal solution was formed by mixing the following components in the weight percents listed in Table III with heating, if necessary, to dissolve the test material.

TABLE III

| Component | Weight Percent |
|---|---|
| Licristal ™ E7 | 97-99.5 |
| Test Material | 0.5-3 |

An optical bench was used to measure the optical properties of the cell and derive the absorption ratios for each of the Test Materials. The filled cell assembly was placed on the optical bench with an activating light source (an Oriel Model 66011 300-Watt Xenon arc lamp fitted with a Melles Griot 04 IES 211 high-speed computer controlled shutter that momentarily closed during data collection so that stray light would not interfere with the data collection process, a Schott 3 mm KG-1 band-pass filter, which removed short wavelength radiation, neutral density filter(s) for intensity attenuation and a condensing lens for beam collimation) positioned at a 30° to 35° angle of incidence a surface of the cell assembly.

A broadband light source for monitoring response measurements was positioned in a perpendicular manner to a surface of the cell assembly. Increased signal of shorter visible wavelengths was obtained by collecting and combining separately filtered light from a 100-Watt tungsten halogen lamp (controlled by a Lambda UP60-14 constant voltage powder supply) with a split-end, bifurcated fiber optical cable. Light from one side of the tungsten halogen lamp was filtered with a Schott KG1 filter to absorb heat and a Hoya B-440 filter to allow passage of the shorter wavelengths. The other side of the light was either filtered with a Schott KG1 filter or unfiltered. The light was collected by focusing light from each side of the lamp onto a separate end of the split-end, bifurcated fiber optic cable, and subsequently combined into one light source emerging from the single end of the cable. A 4" light pipe was attached to the single end of the cable to insure proper mixing.

Polarization of the light source was achieved by passing the light from the single end of the cable through a Moxtek, Proflux Polarizer held in a computer driven, motorized rotation stage (Model M-061-PD from Polytech, PI). The monitoring beam was set so that the one polarization plane (0°) was perpendicular to the plane of the optical bench table and the second polarization plane (90°) was parallel to the plane of the optical bench table. The samples were run in air, at room temperature (73° F.±5° F. or better) maintained by the lab air conditioning system or a temperature controlled air cell.

To conduct the measurements, the cell assembly was exposed to 6.7 W/m$^2$ of UVA from the activating light source for 5 to 15 minutes to activate the Test Material. An International Light Research Radiometer (Model IL-1700) with a detector system (Model SED033 detector, B Filter, and diffuser) was used to verify exposure prior to each test. Light from the monitoring source that was polarized to the 0° polarization plane was then passed through the coated sample and focused on a 2" integrating sphere, which was connected to an Ocean Optics 2000 spectrophotometer using a single function fiber optic cable. The spectral information, after passing through the sample, was collected using Ocean Optics OOI-Base32 and OOIColor software, and PPG propriety software. While the photochromic-dichroic material was activated, the position of the polarizing sheet was rotated back and forth to polarize the light from the monitoring light source to the 900 polarization plane and back. Data was collected for approximately 10 to 300 seconds at 3-second intervals during activation. For each test, rotation of the polarizers was adjusted to collect data in the following sequence of polarization planes: 0°, 90°, 90°, 0°, etc.

Absorption spectra were obtained and analyzed for each cell assembly using the Igor Pro software (available from WaveMetrics). The change in the absorbance in each polarization direction for each cell assembly was calculated by subtracting out the 0 time (i.e., unactivated) absorption measurement for the cell assembly at each wavelength tested. Average absorbance values were obtained in the region of the activation profile where the photochromic response of the Test Material was saturated or nearly saturated (i.e., the regions where the measured absorbance did not increase or did not increase significantly over time) for each cell assembly by averaging absorbance at each time interval in this region. The average absorbance values in a predetermined range of wavelengths corresponding $\lambda_{max-vis}$+/−5 nm were extracted for the 0° and 90° polarizations, and the absorption ratio for each wavelength in this range was calculated by dividing the larger average absorbance by the small average absorbance. For each wavelength extracted, 5 to 100 data points were averaged. The average absorption ratio for the Test Material was then calculated by averaging these individual absorption ratios.

For each Test Material, the above-described procedure was run at least twice. The tabled value for the Average Absorption Ratio represents an average of the results obtained from the runs. The results of these tests are present in Table IV below.

TABLE IV

| Example Number | Wavelength Range $\lambda_{max-vis}$ (nm) (+/−5 nm) | Average Absorption Ratio (AR) |
|---|---|---|
| Comparative Example | 623 +/− 5 nm | 2.3 |
| 1 | 500 +/− 5 nm | 3.9 |
| 2 | 601 +/− 5 nm | 2.2 |
| 3 | 505 +/− 5 nm | 3.7 |
| 4 | 628 +/− 5 nm | 4.8 |
| 5 | 529 +/− 5 nm | 3.3 |
| 6 | 507 +/− 5 nm | 6.0 |
| 7 | 640 +/− 5 nm | 6.6 |
| 8* | — | — |
| 9* | — | — |
| 10 | 584 +/− 5 nm | 3.9 |
| 11* | — | — |
| 12 | 571 +/− 5 nm | 2.7 |
| 13 | 590 +/− 5 nm | 4.0 |
| 14 | 590 +/− 5 nm | 6.0 |
| 15 | 590 +/− 5 nm | 7.8 |
| 16 | 586 +/− 5 nm | 8.3 |
| 17 | 587 +/− 5 nm | 7.0 |

*Too fast fading to measure

Example 20

The average absorption ratio for each of the named compounds in Table V was determined as set forth above in Example 19. It will be appreciated by those skilled in the art that the compounds listed in Table V may be made in accordance with the teachings and examples disclosed herein with appropriate modifications, which will be readily apparent to those skilled in the art. Further, those skilled in the art will recognize that various modifications to the disclosed methods, as well as other methods, can be used in making the named compounds set forth below in Table V.

TABLE V

| Compound Name | Wavelength Range $\lambda_{max}$ (nm) +/− 5 nm | Average Absorption Ratio (AR) |
|---|---|---|
| 3-phenyl-3-(4-(4-benzylpiperidino)phenyl)-13,13-dimethyl-indeno[2',3':3,4]naphtho[1,2-b]pyran | 610 | 2.2 |

TABLE V-continued

| Compound Name | Wavelength Range $\lambda_{max}$ (nm) +/− 5 nm | Average Absorption Ratio (AR) |
|---|---|---|
| 3-phenyl-3-(4-(3-piperidin-4-yl-propyl)piperidino)phenyl)-13,13-dimethyl-indeno[2',3':3,4]-naphtho[1,2-b]pyran | 590 | 2.0 |
| 3-phenyl-3-(4-(4-hexyloxymethyl piperidino)phenyl)-13,13-dimethyl-indeno[2',3':3,4]naphtho[1,2-b]pyran | 606 | 2.2 |
| 3-phenyl-3-(4-([1,4']bipiperidinyl-1'-yl)phenyl)-13,13-dimethyl-6-methoxy-7-(piperadin-1-yl)indeno[2',3':3,4] naphtho[1,2-b]pyran | 515 | 2.3 |
| 3-phenyl-3-(4-([1,4']bipiperidinyl-1'-yl)phenyl)-13,13-dimethyl-6-methoxy-7-([1,4']bipiperidinyl-1'-yl)indeno[2',3':3,4]naphtho[1,2-b]pyran | 513 | 3.4 |
| 3-phenyl-3-(4-pyrrolidin-1-yl-phenyl)-13,13-dimethyl-6-methoxy-7-([1,4']bipiperidinyl-1"-yl)indeno[2',3':3,4]naphtho[1,2-b]pyran | 630 | 2.8 |
| 3-phenyl-3-(4-([1,4']bipiperidinyl-1'-yl)phenyl)-13,13-dimethyl-6-methoxy-7-(4-benzylpiperidin-1-yl)indeno[2',3':3,4]naphtho[1,2-b]pyran | 515 | 2.7 |
| 3-phenyl-3-(4-(4-phenylpiperazine)phenyl)-13,13-dimethyl-indeno[2',3':3,4]naphtho[1,2-b]pyran | 592 | 2.2 |
| 3-phenyl-3-(4-(4-benzylpiperazine)phenyl)-13,13-dimethyl-indeno[2',3':3,4]naphtho[1,2-b]pyran | 598 | 2.1 |
| 3-phenyl-3-(4-pyrrolidin-1-yl-phenyl)-13,13-dimethyl-6-methoxy-7-(4-phenyl-piperazin-1-yl)indeno[2',3':3,4]naphtho[1,2-b]pyran | 632 | 4.5 |
| 3-phenyl-3-(4-(4-phenyl-piperazin-1-yl)phenyl)-13,13-dimethyl-6-methoxy-7-(4-(4-hexyloxy-benzoyloxy)-piperidin-1-yl)indeno[2',3':3,4] naphtho[1,2-b]pyran | 501 | 3.9 |
| 3-phenyl-3-(4-(4-phenyl-piperazin-1-yl)phenyl)-13,13-dimethyl-6-methoxy-7-(4-(4-hexylbenzoyloxy)-piperidin-1-yl)indeno[2',3':3,4] naphtho[1,2-b]pyran | 503 | 3.9 |
| 3-phenyl-3-(4-(4-phenyl-piperazin-1-yl)phenyl)-13,13-dimethyl-6-methoxy-7-(4-(biphenyl-4-carbonyloxy)-piperidin-1-yl]indeno[2',3':3,4]naphtho[1,2-b]pyran | 501 | 4.2 |
| 3-phenyl-3-(4-(4-phenyl-piperazin-1-yl)phenyl)-13,13-dimethyl-6-methoxy-7-(4-(4'-octyloxy-biphenyl-4-carbonyloxy)-piperidin-1-yl)indeno[2',3':3,4]naphtho[1,2-b]pyran | 499 | 4.1 |
| 3-phenyl-3-(4-(4-hexylbenzoyloxy)-piperidin-1-yl)phenyl)-13,13-dimethyl-6-methoxy-7-(4-(4-hexylbenzoyloxy)-piperidin-1-yl)indeno[2',3':3,4]naphtho[1,2-b]pyran | 505 | 4.3 |
| 3-phenyl-3-(4-(4-(4-butyl-phenylcarbamoyl)-piperidin-1-yl)phenyl)-13,13-dimethyl-6-methoxy-7-(4-phenyl-piperazin-1-yl)indeno[2',3':3,4] naphtho[1,2-b]pyran | 506 | 5.0 |
| 3-phenyl-3-(4-(1-hydroxypiperidin-1-yl)-phenyl)-13,13-dimethyl-6-methoxy-7-(4-phenyl-piperazin-1-yl)indeno[2',3':3,4]naphtho[1,2-b]pyran | 512 | 4.0 |
| 3-phenyl-3-{4-(4-fluorobenzoyloxy)-piperadin-1-yl)phenyl)-13-hydroxy-13-ethyl-6-methoxy-7-(4-phenyl-piperazin-1-yl)-indeno[2',3':3,4]naphtho[1,2-b]pyran | 507 | 3.5 |
| 3-phenyl-3-(4-(4-pyrrolidinylphenyl)-13,13-dimethyl-6-methoxy-7-(-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl}indeno[2',3':3,4] naphtho[1,2-b]pyran | 525 | 6.3 |
| 3-phenyl-3-(4-{4-(biphenyl-4-carbonyloxy]-piperidin-1-yl}-phenyl)-13,13-dimethyl-6-methoxy-7-{44-(biphenyl-4-carbonyloxy)-piperidin-1-yl}-)-indeno[2',3':3,4]naphtho[1,2-b]pyran | 503 | 4.6 |
| 3-phenyl-3-{4-(pyrrolidin-1-yl)phenyl)-13-hydroxy-13-ethyl-6-methoxy-7-(4-hexylbenzoyloxy-piperadin-1-yl)-indeno[2',3':3,4] naphtho[1,2-b]pyran | 635 | 3.4 |
| 3-phenyl-3-(4-(4-phenyl-piperazin-1-yl)phenyl)-13,13-dimethyl-6-methoxy-7-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl}-indeno[2',3':3,4]naphtho[1,2-b]pyran | 502 | 6.0 |
| 3-phenyl-3-{4-(pyrrolidin-1-yl)phenyl)-3-hydroxy-13- | 635 | 5.2 |

TABLE V-continued

| Compound Name | Wavelength Range $\lambda_{max}$ (nm) +/− 5 nm | Average Absorption Ratio (AR) |
|---|---|---|
| ethyl-6-methoxy-7-(4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperadin-1-yl)-indeno[2',3':3,4]naphtho[1,2-b]pyran | | |
| 3-phenyl-3-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl}-phenyl)-13,13-dimethyl-6-methoxy-7-(4-phenyl-piperazin-1-yl)indeno[2',3':3,4]naphtho[1,2-b]pyran | 505 | 4.4 |
| 3-phenyl-3-{4-(pyrrolidin-1-yl)phenyl)-13-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxy]-13-ethyl-6-methoxy-7-(4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperadin-1-yl)-indeno[2',3':3,4]naphtho[1,2-b]pyran | 529 | 3.3 |
| 3-phenyl-3-(4-(4-phenyl-piperazin-1-yl)phenyl)-13,13-dimethyl-6-methoxy-7-(4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyl]-piperazin-1-yl)indeno[2',3':3,4]naphtho[1,2-b]pyran | 503 | 7.1 |
| 3-phenyl-3-{4-(pyrrolidin-1-yl)phenyl)-13-hydroxy-13-ethyl-6-methoxy-7-(4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyl]-piperazin-1-yl)-indeno[2',3':3,4]naphtho[1,2-b]pyran | 637 | 5.3 |
| 3-phenyl-3-(4-(4-phenylpiperazin-1-yl)phenyl)-13,13-dimethyl-6-methoxy-7-(4-(4-phenyl-piperazin-1-yl)-4-oxo-butanoyl)-piperazine-1-yl)-indeno[2',3':3,4]naphtho[1,2-b]pyran | 499 | 4.6 |
| 3-phenyl-3-(4-(4-phenyl-piperazin-1-yl)phenyl)-13,13-dimethyl-6-methoxy-7-(4-(4-(4-hexylbenzoyloxy)phenyl)piperazin-1-yl)indeno[2',3':3,4]naphtho[1,2-b]pyran | 496 | 5.9 |
| 3-phenyl-3-(4-(4-phenylpiperazin-1-yl)phenyl)-13,13-dimethyl-6-methoxy-7-(4-(4-(4-fluorobenzoyloxy)phenyl)piperazin-1-yl)indeno[2',3':3,4]naphtho[1,2-b]pyran | 497 | 5.3 |
| 3-phenyl-3-(4-(4-phenylpiperazin-1-yl)phenyl)-13,13-dimethyl-6-methoxy-7-(4-(4-(4-biphenylcarbonyloxy)phenyl)piperazin-1-yl)indeno[2',3':3,4]naphtho[1,2-b]pyran | 497 | 5.8 |
| 3-phenyl-3-(4-(4-phenylpiperazin-1-yl)phenyl)-13,13-dimethyl-6-methoxy-7-(4-(4-(4'-octyloxy-biphenyl-4-carbonyloxy)phenyl)piperazin-1-yl)indeno[2',3':3,4]naphtho[1,2-b]pyran | 497 | 6.3 |
| 3-phenyl-3-(4-(4-phenyl-piperazin-1-yl)phenyl)-13,13-dimethyl-6-methoxy-7-(4-(4-(4-hexyloxyphenylcarbonyloxy)phenyl)piperazin-1-yl)indeno[2',3':3,4]naphtho[1,2-b]pyran | 496 | 5.8 |
| 3-phenyl-3-(4-(4-phenyl-piperazin-1-yl)phenyl)-13,13-dimethyl-6-methoxy-7-{4-(4-(4-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-phenyl)-piperidin-1-yl}-indeno[2',3':3,4]naphtho[1,2-b]pyran | 499 | 5.6 |
| 3-phenyl-3-(4-(4-hexylbenzoyloxy)phenyl)piperazin-1-yl)phenyl-13,13-dimethyl-6-methoxy-7-(4-phenylpiperazin-1-yl)-indeno[2',3':3,4]naphtho[1,2-b]pyran | 499 | 4.8 |
| 3-phenyl-3-(4-(4-phenyl-piperazin-1-yl)phenyl)-13,13-dimethyl-6-methoxy-7-(4-(4-(4-hexylbenzoyloxy)benzoyloxy)-phenyl)piperazin-1-yl)indeno[2',3':3,4]naphtho[1,2-b]pyran | 493 | 6.1 |
| 3-phenyl-3-(4-(4-phenyl-piperazin-1-yl)phenyl)-13-hydroxy-13-ethyl-6-methoxy-7-(4-(4-(4-hexylbenzoyloxy)phenyl)piperazin-1-yl)indeno[2',3':3,4]naphtho[1,2-b]pyran | 499 | 5.7 |

TABLE V-continued

| Compound Name | Wavelength Range $\lambda_{max}$ (nm) +/− 5 nm | Average Absorption Ratio (AR) |
|---|---|---|
| 3-phenyl-3-(4-(4-methoxyphenyl)-piperazin-1-yl))phenyl)-13,13-dimethyl-6-methoxy-7-(4-(4-(3-phenylprop-2-ynoyloxy)phenyl)piperazin-1-yl)-indeno[2',3':3,4]naphtho[1,2-b]pyran | 499 | 6.3 |
| 3-phenyl-3-(4-(4-phenyl-piperazin-1-yl)phenyl)-13,13-dimethyl-6-methoxy-7-(4-(4-(4-(2-fluorobenzoyloxy)benzoyloxy)phenyl)piperazin-1-yl)indeno[2',3':3,4]naphtho[1,2-b]pyran | 497 | 5.8 |
| 3-phenyl-3-(4-(4-phenyl-piperazin-1-yl)phenyl)-13,13-dimethyl-6-methoxy-7-(4-(4-(4-(4-fluorobenzoyloxy)benzoyloxy)-phenyl)piperazin-1-yl)indeno[2',3':3,4]naphtho[1,2-b]pyran | 498 | 6.1 |
| 3-phenyl-3-(4-(pyrrolidin-1-yl)phenyl)-13-hydroxy-13-ethyl-6-methoxy-7-(4-(4-(4-hexylbenzoyloxy)phenyl)piperazin-1-yl)indeno[2',3':3,4]naphtho[1,2-b]pyran | 629 | 6.3 |
| 3-phenyl-3-(4-(pyrrolidin-1-yl)phenyl)-13,13-dimethyl-6-methoxy-7-(4-hexylbenzoyloxy)-indeno[2',3':3,4]naphtho[1,2-b]pyran | 645 | 4.7 |
| 3-phenyl-3-(4-(pyrrolidin-1-yl)phenyl)-13,13-dimethyl-6-methoxy-7-(4-(4-hexylbenzoyloxy)benzoyloxy)-indeno[2',3':3,4]naphtho[1,2-b]pyran | 639 | 5.9 |
| 3-phenyl-3-(4-(4-methoxyphenyl)piperazin-1-yl))phenyl)-13,13-dimethyl-6-methoxy-7-(3-(4-hexylbenzoyloxyphenyl)piperazin-1-yl)-indeno[2',3':3,4]naphtho[1,2-b]pyran | 500 | 2.8 |
| 3-phenyl-3-(4-(pyrrolidin-1-yl)phenyl)-13,13-dimethyl-6-methoxy-7-(4-(4-(4-hexylbenzoyloxy)benzoyloxy)benzoyloxy)indeno[2',3':3,4]naphtho[1,2-b]pyran | 646 | 6.4 |
| 3-phenyl-3-(4-(4-phenyl-piperazin-1-yl)phenyl)-13,13-dimethyl-6-methoxy-7-(4-(4-(4-(4-hexylbenzoyloxy)benzoyloxy)-benzoyloxy)phenyl)piperazin-1-yl)indeno[2',3':3,4]naphtho[1,2-b]pyran | 497 | 7.1 |
| 3-(4-methoxyphenyl)-3-(4-(4-methoxyphenyl)piperazin-1-yl)phenyl)-13-ethyl-13-hydroxy-6-methoxy-7-(4-(4-(4-hexylbenzoyloxy)phenyl)piperazin-1-yl)indeno[2',3':3,4]naphtho[1,2-b]pyran | 499 | 5.4 |
| 2-phenyl-2-{4-[4-(4-Methoxy-phenyl)-piperazin-1-yl]-phenyl}-benzofuro[3',2':7,8]benzo[b]pyran | 583 | 4.2 |
| 2-phenyl-2-{4-[4-(4-Methoxy-phenyl)-piperazin-1-yl]-phenyl}-benzothieno[3',2':7,8]benzo[b]pyran | 510 | 4.1 |
| 3-phenyl-3-(4-(4-phenyl-piperazin-1-yl)phenyl)-13,13-dimethyl-6-methoxy-7-(4-(4-(4-(6-(4-(4-(4-nonylphenylcabonyloxy)phenyl)oxycarbonyl)-phenoxy)hexyloxy)benzoyioxy)phenyl)piperazin-1-yl)indeno[2',3':3,4] naphtho[1,2-b]pyran | 495 | 6.1 |
| 3-phenyl-3-(4-(4-phenyl-piperazin-1-yl)phenyl)-13-hydroxy-13-ethyl-6-methoxy-7-(4-(4-(4-(6-(4-(4-(4-nonylphenylcabonyloxy)phenyl)-oxycarbonyl)phenoxy)hexyloxy)benzoyloxy)phenyl)piperazin-1-yl)indeno[2',3':3,4] naphtho[1,2-b]pyran | 500 | 6.0 |
| 3-phenyl-3-(4-pyrrolidinylphenyl)-13,13-dimethyl-6-methoxy-7-(4-(4-(4-(6-(4-(4-(4-nonylphenylcabonyloxy)phenyl)oxycarbonyl)phenoxy)-hexyloxy)phenyl)piperazin-1-yl)indeno[2',3':3,4] naphtho[1,2-b]pyran | 627 | 6.5 |

It is to be understood that the present description illustrates aspects of the invention relevant to a clear understanding of the invention. Certain aspects of the invention that would be apparent to those of ordinary skill in the art and that, therefore, would not facilitate a better understanding of the invention have not been presented in order to simplify the present description. Although the present invention has been described in connection with certain embodiments, the present invention is not limited to the particular embodiments disclosed, but is intended to cover modifications that are within the spirit and scope of the invention, as defined by the appended claims.

We claim:

1. A photochromic compound having:
(a) at least one photochromic group represented by Formula II or XII:

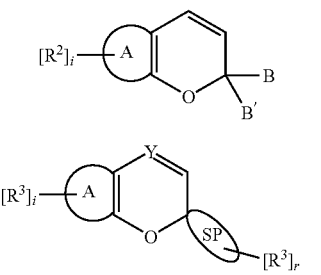

and
(b) at least one lengthening agent $L^2$ attached to the at least one photochromic group, the at least one lengthening agent $L^2$ represented by:

wherein:
(i) P' is a group chosen from steroid radicals, terpenoid radicals, alkaloid radicals, and liquid crystal mesogens; and
(ii) s' is chosen from 0 to 20, and each S is independently chosen for each occurrence from a spacer unit chosen from:
(A) —$(CH_2)_g$—, —$(CF_2)_h$—, —$Si(CH_2)_g$—, —$(Si[(CH_3)_2]O)_h$—, wherein g is independently chosen for each occurrence from 1 to 20; h is a whole number from 1 to 16 inclusive;
(B) —N(Z)-, —C(Z)=C(Z)-, —C(Z)=N—, —C(Z')-C(Z')-, wherein Z is independently chosen for each occurrence from hydrogen, $C_1$-$C_6$alkyl, cycloalkyl and aryl, and Z' is independently chosen for each occurrence from $C_1$-$C_6$alkyl, cycloalkyl and aryl; and
(C) —O—, —C(O)—, —C≡O—, —N=N—, —S—, —S(O)—, —S(O)(O)—, straight-chain or branched $C_1$-$C_{24}$ alkylene residue, said $C_1$-$C_{24}$ alkylene residue being unsubstituted, mono-substituted by cyano or halo, or poly-substituted by halo; provided that when two spacer units comprising heteroatoms are linked together the spacer units are linked so that heteroatoms are not directly linked to each other and wherein:
(c) A is chosen from naphtho, benzo, phenanthro, fluorantheno, antheno, quinolino, thieno, furo, indolo, indolino, indeno, benzofuro, benzothieno, thiopheno, indeno-fused naphtho, heterocyclic-fused naphtho, and heterocyclic-fused benzo;
(d) Y is C;
(e) SP is a spiro-group chosen from indolino and benzindolino;
(f) B and B' are each independently chosen from:
(i) hydrogen, $C_1$-$C_{12}$ alkyl, $C_2$-$C_{12}$ alkylidene, $C_2$-$C_{12}$ alkylidyne, vinyl, $C_3$-$C_7$ cycloalkyl, $C_1$-$C_{12}$ haloalkyl, allyl, halogen, and benzyl that is unsubstituted or mono-substituted with at least one of $C_1$-$C_{12}$ alkyl and $C_1$-$C_{12}$ alkoxy;
(ii) phenyl that is mono-substituted at the para position with at least one substituent chosen from: $C_1$-$C_7$ alkoxy, linear or branched chain $C_1$-$C_{20}$ alkylene, linear or branched chain $C_1$-$C_4$ polyoxyalkylene, cyclic $C_3$-$C_{20}$ alkylene, phenylene, naphthylene, $C_1$-$C_4$ alkyl substituted phenylene, mono- or poly-urethane ($C_1$-$C_{20}$)alkylene, mono- or poly-ester($C_1$-$C_{20}$)alkylene, mono- or poly-carbonate($C_1$-$C_{20}$)alkylene, polysilanylene, polysiloxanylene and mixtures thereof, wherein the at least one substituent is connected to an aryl group of a photochromic material;
(iii) —$CH(CN)_2$ and —$CH(COOX_1)_2$, wherein $X_1$ is chosen from at least one of a lengthening agent $L^2$, hydrogen, $C_1$-$C_{12}$ alkyl that is unsubstituted or mono-substituted with phenyl, phenyl($C_1$-$C_{12}$)alkyl that is mono-substituted with $C_1$-$C_{12}$ alkyl or $C_1$-$C_{12}$ alkoxy, and an aryl group that is unsubstituted, mono- or di-substituted, wherein each aryl substituent is independently chosen from $C_1$-$C_{12}$ alkyl and $C_1$-$C_{12}$ alkoxy;
(iv) —$CH(X_2)(X_3)$, wherein:
(A) $X_2$ is chosen from at least one of a lengthening agent $L^2$, hydrogen, $C_1$-$C_{12}$ alkyl, and an aryl group that is unsubstituted, mono- or di-substituted, wherein each aryl substituent is independently chosen from $C_1$-$C_{12}$ alkyl and $C_1$-$C_{12}$ alkoxy; and
(B) $X_3$ is chosen from at least one of —$COOX_1$, —$COX_1$, —$COX_4$, and —$CH_2OX_5$, wherein:
(1) $X_4$ is chosen from at least one of morpholino, piperidino, amino that is unsubstituted, mono- or di-substituted with $C_1$-$C_{12}$ alkyl, and an unsubstituted, mono or di-substituted group chosen from phenylamino and diphenylamino, wherein each substituent is independently chosen from $C_1$-$C_{12}$ alkyl or $C_1$-$C_{12}$ alkoxy; and
(2) $X_5$ is chosen from a lengthening agent $L^2$, hydrogen, —$C(O)X_2$, $C_1$-$C_{12}$ alkyl that is unsubstituted or mono-substituted with ($C_1$-$C_{12}$) alkoxy or phenyl, phenyl($C_1$-$C_{12}$)alkyl that is mono-substituted with ($C_1$-$C_{12}$)alkoxy, and an aryl group that is unsubstituted, mono- or di-substituted, wherein each aryl substituent is independently chosen from $C_1$-$C_{12}$ alkyl and $C_1C_{12}$ alkoxy;
(v) an unsubstituted, mono-, di-, or tri-substituted aryl group; 9-julolidinyl; or an unsubstituted mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, or fluorenyl;

wherein each substituent is independently chosen for each occurrence from:
(A) a lengthening agent $L^2$;
(B) —C(O)$X_6$, wherein $X_6$ is chosen from at least one of: a lengthening agent $L^2$, hydrogen, $C_1$-$C_{12}$ alkoxy, phenoxy that is unsubstituted, mono- or di-substituted with $C_1$-$C_{12}$ or $C_1$-$C_{12}$ alkoxy, an aryl group that is unsubstituted, mono- or di-substituted with $C_1$-$C_{12}$ alkyl or $C_1$-$C_{12}$ alkoxy, an amino group that is unsubstituted, mono- or di-substituted with $C_1$-$C_{12}$ alkyl, and a phenylamino group that is unsubstituted, mono- or di-substituted with $C_1$-$C_{12}$ alkyl or $C_1$-$C_{12}$ alkoxy;
(C) aryl, haloaryl, $C_3$-$C_7$ cycloalkylaryl, and an aryl group that is mono- or di-substituted with $C_1$-$C_{12}$ alkyl or $C_1$-$C_{12}$ alkoxy;
(D) $C_1$-$C_{12}$ alkyl, $C_3$-$C_7$ cycloalkyl, $C_3$-$C_7$ cycloalkyloxy($C_1$-$C_{12}$)alkyl, aryl($C_1$-$C_{12}$)alkyl, aryloxy($C_1$-$C_{12}$)alkyl, mono- or di-($C_1$-$C_{12}$)alkylaryl($C_1$-$C_{12}$)alkyl, mono- or di-($C_1$-$C_{12}$)alkoxyaryl($C_1$-$C_{12}$)alkyl, haloalkyl, and mono($C_1$-$C_{12}$)alkoxy($C_1$-$C_{12}$)alkyl;
(E) $C_1$-$C_{12}$ alkoxy, $C_3$-$C_7$ cycloalkoxy, cycloalkyloxy($C_1$-$C_{12}$)alkoxy, aryl($C_1$-$C_{12}$)alkoxy, aryloxy($C_1$-$C_{12}$)alkoxy, mono- or di-($C_1$-$C_{12}$)alkylaryl($C_1$-$C_{12}$)alkoxy, and mono- or di-($C_1$-$C_{12}$)alkoxyaryl($C_1$-$C_{12}$)alkoxy;
(F) amido, amino, mono- or di-alkylamino, diarylamino, piperazino, N-($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidyl, hydroxy, acryloxy, methacryloxy, and halogen;
(G) —O$X_7$ or —N($X_7$)$_2$, wherein $X_7$ is chosen from:
  (1) a lengthening agent $L^2$, hydrogen, $C_1$-$C_{12}$ alkyl, $C_1$-$C_{12}$acyl, phenyl($C_1$-$C_{12}$)alkyl, mono($C_1$-$C_{12}$) alkyl substituted phenyl($C_1$-$C_{12}$)alkyl, mono($C_1$-$C_{12}$)alkoxy substituted phenyl($C_1$-$C_{12}$)alkyl; $C_1$-$C_{12}$ alkoxy($C_1$-$C_{12}$)alkyl; $C_3$-$C_7$ cycloalkyl; mono($C_1$-$C_{12}$)alkyl substituted $C_3$-$C_7$ cycloalkyl, $C_1$-$C_{12}$ haloalkyl, allyl, benzoyl, mono-substituted benzoyl, naphthoyl or mono-substituted naphthoyl, wherein each of said benzoyl and naphthoyl substituents are independently chosen from $C_1$-$C_{12}$ alkyl, and $C_1$-$C_{12}$ alkoxy;
  (2) —CH($X_8$)$X_9$, wherein $X_8$ is chosen from a lengthening agent $L^2$, hydrogen or $C_1$-$C_{12}$ alkyl; and $X_9$ is chosen from a lengthening agent $L^2$, —CN, —$CF_3$, or —COO$X_{10}$, wherein $X_{10}$ is chosen from a lengthening agent $L^2$, hydrogen or $C_1$-$C_{12}$ alkyl;
  (3) —C(O)$X_6$; or
  (4) tri($C_1$-$C_{12}$)alkylsilyl, tri($C_1$-$C_{12}$)alkoxysilyl, di($C_1$-$C_{12}$)alkyl($C_1$-$C_{12}$alkoxy)silyl, or di($C_1$-$C_{12}$)alkoxy($C_1$-$C_{12}$ alkyl)silyl;
(H) —S$X_{11}$, wherein $X_{11}$ is chosen from a lengthening agent $L^2$, $C_1$-$C_{12}$ alkyl, an aryl group that is unsubstituted, or mono- or di- substituted with $C_1$-$C_{12}$ alkyl, $C_1$-$C_{12}$ alkoxy, or halogen;
(I) a nitrogen containing ring represented by Formula i:

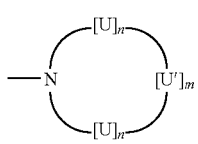

i wherein
  (1) n is an integer chosen from 0, 1, 2, and 3, provided that if n is 0, U' is U, and each U is independently chosen for each occurrence from —$CH_2$—, —CH($X_{12}$)—, —C($X_{12}$)$_2$—, —CH($X_{13}$)—, —C($X_{13}$)$_2$—, and —C($X_{12}$)($X_{13}$)—, wherein $X_{12}$ is chosen from a lengthening agent $L^2$, and $C_1$-$C_{12}$ alkyl, and $X_{13}$ is chosen from a lengthening agent $L^2$, phenyl and naphthyl, and
  (2) U' is chosen from U, —O—, —S—, —S(O)—, —NH—, —N($X_{12}$)— or —N($X_{13}$)—, and m is an integer chosen from 1, 2, and 3, and
(J) a group represented by Formula ii or iii:

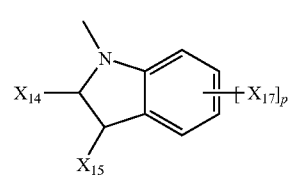

ii

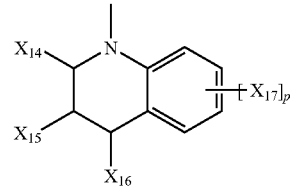

iii wherein $X_{14}$, $X_{15}$, and $X_{16}$ are independently chosen for each occurrence from a lengthening agent $L^2$, $C_1$-$C_{12}$ alkyl, phenyl or naphthyl, or $X_{14}$ and $X_{15}$ together form a ring of 5 to 8 carbon atoms; p is an integer chosen from 0, 1, or 2, and $X_{17}$ is independently chosen for each occurrence from a lengthening agent $L^2$, $C_1$-$C_{12}$ alkyl, $C_1$-$C_{12}$ alkoxy, or halogen;
(vi) an unsubstituted or mono-substituted group chosen from pyrazolyl, imidazolyl, pyrazolinyl, imidazolinyl, pyrrolidinyl, phenothiazinyl, phenoxazinyl, phenazinyl, or acridinyl, wherein each substituent is independently chosen from a lengthening agent $L^2$, $C_1$-$C_{12}$ alkyl, $C_1$-$C_{12}$ alkoxy, phenyl, hydroxy, amino or halogen;
(vii) a group represented by Formula iv or v:

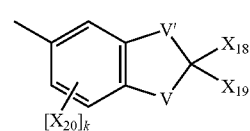

iv

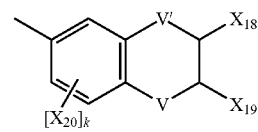

v wherein
(A) V' is independently chosen in each formula from —O—, —CH—, $C_1$-$C_6$ alkylene, and $C_3$-$C_7$ cycloalkylene,
(B) V is independently chosen in each formula from —O— or —N($X_{21}$)—, wherein $X_{21}$ is from a lengthening agent $L^2$, hydrogen, $C_1$-$C_{12}$ alkyl, and $C_2$-$C_{12}$ acyl, provided that if V is —N($X_{21}$)—, V' is —$CH_2$—, (C) $X_{18}$ and $X_{19}$ are each independently chosen from a lengthening agent $L^2$, hydrogen and $C_1$-$C_{12}$ alkyl, and (D) k is chosen from 0, 1, and 2, and each $X_{20}$ is independently chosen for each occurrence from a lengthening agent $L^2$, $C_1$-$C_{12}$ alkyl, $C_1$-$C_{12}$ alkoxy, hydroxy and halogen;

(viii) a group represented by Formula vi:

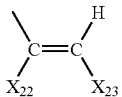

vi wherein (A) $X_{22}$ is chosen from a lengthening agent $L^2$, hydrogen and $C_1$-$C_{12}$ alkyl, and (B) $X_{23}$ is chosen from a lengthening agent $L^2$ and an unsubstituted, mono-, or di-substituted group chosen from naphthyl, phenyl, furanyl and thienyl, wherein each substituent is independently chosen for each occurrence from $C_1$-$C_{12}$ alkyl, $C_1$-$C_{12}$ alkoxy, and halogen; and (ix) B and B' together form fluoren-9-ylidene, mono- or di-substituted fluoren-9-ylidene, or a saturated $C_3$-$C_{12}$ spiro-monocyclic hydrocarbon ring, saturated $C_7$-$C_{12}$ spiro-bicyclic hydrocarbon rings, saturated $C_7$-$C_{12}$ spiro-tricyclic hydrocarbon rings; and (g) i is an integer chosen from 0 to the total number of available positions on A, r is an integer chosen from 0 to the total number available positions on SP, provided that the sum of i+r is at least one, and each $R^2$ and $R^3$ is independently chosen for each occurrence from:

(i) a group represented by B;

(ii) —C(O)$X_{24}$, wherein $X_{24}$ is chosen from a lengthening agent $L^2$, hydroxy, $C_1$-$C_{12}$ alkyl, $C_1$-$C_{12}$ alkoxy, phenyl that is unsubstituted or mono-substituted with $C_1$-$C_{12}$ alkyl or $C_1$-$C_{12}$ alkoxy, amino that is unsubstituted, mono- or di-substituted with at least one of $C_1$-$C_{12}$ alkyl, phenyl, benzyl, and naphthyl;

(iii) —O$X_7$ and —N($X_7$)$_2$;

(iv) —S$X_{11}$;

(v) the nitrogen containing ring represented by Formula i;

(vi) the group represented by Formula ii or iii;

(vii) immediately adjacent $R^2$ groups together form at a group represented by Formula vii, viii, or ix:

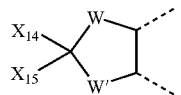

vii

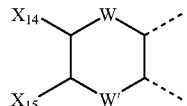

viii

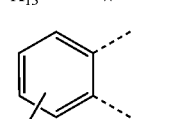

ix wherein (A) W and W' are independently chosen for each occurrence from —O—, —N($X_7$)—, —C($X_{14}$)—, —C($X_{17}$)—, (B) $X_{14}$, $X_{15}$ and $X_{17}$, and (C) q is an integer chosen from 0, 1, 2, 3, and 4.

2. The photochromic compound of claim 1 wherein the photochromic group is a thermally reversible photochromic group chosen from benzopyrans, naphthopyrans, spiro-9-fluoreno[1,2-b]pyrans, phenanthropyrans, quinopyrans, fluoroanthenopyrans, and spiropyrans.

3. The photochromic compound of claim 1 wherein the steroid radical is a cholesterolic compound.

* * * * *